(12) United States Patent
Ghatnekar

(10) Patent No.: US 11,524,049 B2
(45) Date of Patent: *Dec. 13, 2022

(54) FORMULATIONS AND METHODS OF USE FOR ALPHA CONNEXIN C-TERMINAL (ACT) PEPTIDES

(71) Applicant: XEQUEL BIO, INC., Mt. Pleasant, SC (US)

(72) Inventor: Gautam Ghatnekar, Mt. Pleasant, SC (US)

(73) Assignee: XEQUEL BIO, INC., Mt. Pleasant, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/859,075

(22) Filed: Apr. 27, 2020

(65) Prior Publication Data

US 2021/0128682 A1 May 6, 2021

Related U.S. Application Data

(63) Continuation of application No. 14/848,916, filed on Sep. 9, 2015, now Pat. No. 10,632,173, which is a continuation of application No. 14/341,406, filed on Jul. 25, 2014, now Pat. No. 9,161,984, which is a continuation of application No. 13/815,723, filed on Mar. 15, 2013, now Pat. No. 8,846,605, which is a continuation-in-part of application No. PCT/US2013/028727, filed on Mar. 1, 2013.

(60) Provisional application No. 61/605,528, filed on Mar. 1, 2012.

(51) Int. Cl.

| A61K 38/17 | (2006.01) |
| A61K 9/00 | (2006.01) |
| A61K 9/06 | (2006.01) |
| A61K 47/38 | (2006.01) |

(52) U.S. Cl.
CPC ........ *A61K 38/1709* (2013.01); *A61K 9/0014* (2013.01); *A61K 9/06* (2013.01); *A61K 38/1703* (2013.01); *A61K 38/177* (2013.01); *A61K 38/1767* (2013.01); *A61K 47/38* (2013.01)

(58) Field of Classification Search
None
See application file for complete search history.

(56) References Cited

U.S. PATENT DOCUMENTS

| 5,234,809 | A | 8/1993 | Boom et al. |
| 5,401,504 | A | 3/1995 | Das et al. |
| 6,685,971 | B2 | 2/2004 | Xu et al. |
| 6,991,813 | B2 | 1/2006 | Xu et al. |
| 7,098,190 | B1 | 8/2006 | Becker et al. |
| 7,415,306 | B2 | 8/2008 | Levin et al. |
| 7,615,540 | B2 | 11/2009 | Green |
| 7,786,074 | B2 * | 8/2010 | Gourdie ................. A61K 38/10 514/1.2 |
| 7,879,811 | B2 | 2/2011 | Green |
| 7,888,319 | B2 | 2/2011 | Gourdie et al. |
| 7,919,474 | B2 | 4/2011 | Green |
| 8,846,605 | B2 * | 9/2014 | Ghatnekar ......... A61K 38/1767 514/1.1 |
| 8,916,515 | B2 * | 12/2014 | Ghatnekar ........... A61K 38/177 514/1 |
| 9,161,984 | B2 * | 10/2015 | Ghatnekar ......... A61K 38/1709 |
| 10,632,173 | B2 * | 4/2020 | Ghatnekar ......... A61K 38/1767 |
| 2003/0108886 | A1 | 6/2003 | Finn et al. |
| 2003/0215424 | A1 | 11/2003 | Seul et al. |
| 2005/0053918 | A1 | 3/2005 | Barnea et al. |
| 2005/0075280 | A1 | 4/2005 | Larsen et al. |
| 2007/0072819 | A1 | 3/2007 | Becker |
| 2007/0072820 | A1 | 3/2007 | Green |
| 2007/0104665 | A1 | 5/2007 | Jones et al. |
| 2007/0244062 | A1 | 10/2007 | Laux |
| 2008/0095819 | A1 | 4/2008 | Gourdie et al. |
| 2008/0242631 | A1 | 10/2008 | Becker et al. |
| 2008/0249041 | A1 | 10/2008 | Becker |
| 2008/0299228 | A1 | 12/2008 | Harris et al. |
| 2009/0131313 | A1 | 5/2009 | Sosne et al. |
| 2009/0142295 | A1 | 6/2009 | Becker |

(Continued)

FOREIGN PATENT DOCUMENTS

| CA | 1295242 C | 2/1992 |
| CA | 2592285 A1 | 12/2008 |

(Continued)

OTHER PUBLICATIONS

Akbari et al., "Effects of vacuum-compression therapy on healing of diabetic foot ulcers: Randomized controlled trial," J. Rehab. Res. Devel. 44:631-636 (2007).

Alonso and Fuchs. "Stem cells of the skin epithelium", Proc Natl Acad Sci USA.(2003), 100 (Suppl 1): 11830-11835.

Angst et al. "Dissociated spatial patterning of gap junctions and cell adhesion junctions during postnatal differentiation of ventricular myocardium", Circulation Research (1997), 80: 88-94.

Barker and Gourdie. "Connexin Interacting Proteins. In: Heart Cell Coupling and Impulse Propagation in Health and Disease", Eds., De Mello W.C. and Janse M.J., Kluwer, Boston, pp. 25-50.

Barker and Gourdie. "JNK bond regulation: why do mammalian hearts invest in connexin43?" Circ Res. (2002), 91(7): 556-558.

(Continued)

*Primary Examiner* — Sergio Coffa
(74) *Attorney, Agent, or Firm* — Cooley LLP

(57) ABSTRACT

This invention relates to a topical gel drug product preparation containing a composition comprising an isolated polypeptide having a carboxy-terminal amino acid sequence of an alpha connexin (ACT peptide), peptide stabilizers, excipients, buffering agents, and the like. A formulation and preparation steps are disclosed for the manufacturing of a stable, elegant, and pourable topical gel. The resulting formulation possesses long term stability suitable for aesthetic as well as therapeutic applications including the prevention of scaring and accelerated healing of wounds. Methods for treatment of chronic wounds, including chronic ulcers, are also provided.

5 Claims, 18 Drawing Sheets

Specification includes a Sequence Listing.

(56) References Cited

U.S. PATENT DOCUMENTS

| | | |
|---|---|---|
| 2009/0215665 A1 | 8/2009 | Gourdie et al. |
| 2009/0220450 A1 | 9/2009 | Green et al. |
| 2010/0093691 A1 | 4/2010 | Beck et al. |
| 2010/0279921 A1 | 11/2010 | Duft |
| 2011/0038920 A1* | 2/2011 | Mori .................. C12N 15/1136 424/445 |
| 2011/0065770 A1 | 3/2011 | Becker |
| 2011/0092449 A1 | 4/2011 | Duft |
| 2011/0130345 A1 | 6/2011 | Rohrer et al. |
| 2011/0130710 A1 | 6/2011 | Becker et al. |
| 2011/0136890 A1 | 6/2011 | Becker et al. |
| 2011/0144182 A1 | 6/2011 | Becker et al. |
| 2011/0166653 A1 | 7/2011 | Becker et al. |
| 2011/0217313 A1 | 9/2011 | Becker et al. |
| 2011/0223204 A1 | 9/2011 | Duft |
| 2011/0243964 A1 | 10/2011 | Duft |
| 2011/0245184 A1 | 10/2011 | Duft |
| 2011/0300130 A1 | 12/2011 | Becker et al. |
| 2013/0267471 A1 | 10/2013 | Ghatnekar |
| 2015/0018284 A1 | 1/2015 | Ghatnekar |
| 2016/0058834 A1 | 3/2016 | Ghatnekar |

FOREIGN PATENT DOCUMENTS

| | | |
|---|---|---|
| EP | 0267015 A2 | 5/1988 |
| EP | 0539140 A1 | 4/1993 |
| JP | 2003-238441 A | 8/2003 |
| WO | WO 00/44409 A1 | 8/2000 |
| WO | WO 00/69896 A2 | 11/2000 |
| WO | WO 02/042422 A2 | 5/2002 |
| WO | WO 02/094981 A2 | 11/2002 |
| WO | WO 03/014303 A2 | 2/2003 |
| WO | WO 03/032964 A2 | 4/2003 |
| WO | WO2006/069181 * | 6/2006 |
| WO | WO 2006/069181 A2 | 6/2006 |
| WO | WO 2006/134494 A2 | 12/2006 |
| WO | WO 2009/075881 A2 | 6/2009 |
| WO | WO 2009/085272 A2 | 7/2009 |
| WO | WO 2009/085274 A2 | 10/2009 |
| WO | WO 2013/131040 A1 | 9/2013 |

OTHER PUBLICATIONS

Barker et al. "Increased association of ZO-1 with connexin43 during remodeling of cardiac gap junctions", Circ Res (2002), 90: 317-324.

Barker et al. "Increased co-localization of connexin43 and ZO-1 in dissociated adult myocytes", Cell Commun Adhes. (2001), 8(4-6): 205-8.

Bryant and Sternberg. "Comparison of protein structural profiles by interactive computer graphics", J. Mol. Graphics (1987), 5(1):4-7.

Bucci et al. "In vivo delivery of the caveolin-1 scaffolding domain inhibits nitric oxide synthesis and reduces inflammation", Nat. Med. (2000), 6: 1362-1367.

Bukauskas et al. "Clustering of connexin 43-enhanced green fluorescent protein gap junction channels and functional coupling in living cells",. Proc Natl Acad Sci USA (2000), 97:2556-2561.

Chen et al. "Molecular transporters for peptides: delivery of a cardioprotective epsilonPKC agonist peptide into cells and intact ischemic heart using a transport system, R(7)", Chem Biol (2001), 8: 1123-1129.

Chien, K.R. "Stem cells: lost in translation", Nature (2004), 428(6983): 607-608.

Chu et al. "Predictive Sensitivity of Human Cancer Cells in vivo Using Semipermeable Polysulfone Fibers", Pharmacology (1998) 56(6): 318-326.

Console et al., "Antennapedia and HIV Transactivator of Transcription (TAT) "Protein Transduction Domains" Promote Endocytosis of High Molecular Weight Cargo upon Binding to Cell Surface Glycosaminoglycans," J. Biol. Chem. 278(37):35109-35114 (2003).

CTRI/2011/09/002004. "To study safety and efficacy of GRANEXIN GEL plStandard of Care as cmopared to standard of care alone in reducing scar foiation in wounds following laparoscopic surgery", Registered on Sep. 14, 2011, 6 pages. http://www.ctri.nic.in/Clinicaltrials/pmaindet2.php?trialid=3482.

Dang et al. "The carboxy-tail of connexin-43 localizes to the nucleand inhibits cell growth", Mol Cell Biochem. (2003), 242(1-2): 35-38.

Defamie et al. "Disruption of gap junctional intercellular communication by lindane is associated with aberrant localization of connexin43 and zonula occludens-1 in 42GPA9 Sertoli cells", Carcinogenesis (2001), 22: 1537-1542.

Derossi et al. "The third helix of Antennapedia homeodomain translocates through biological membranes", J Biol. Chem. (1994), 269(14, Issue 8):10444-10450.

Dev, K.K. "Making protein interactions druggable: targeting PDZ domains", Nat Rev Drug Discov. (2004), 3(12): 1047-56.

Diegelmann and Evans. "Wound Healing: An Overview of Acute, Fibrotic and Delayed Healing",Frontiers Biosci. (2004), 9: 283-289.

Duffy et al. "Formation of the gap junction nexus: binding partners for connexins", J Physiol—Paris 96 (2002), pp. 243-249.

Duffy et al. "Regulation of connexin43 protein complexes by intracellular acidification", Circ. Res. (2004), 94: 215-222.

Dupont et al. "Altered connexin expression in human congestive heart failure", J. Mol Cell Cardiol (2002), 33: 359-371.

Elmquist et al. "VE-cadherin-derived cell-penetrating peptide, pVEC, with carrier functions", Exp. Cell Res. (2001), 269: 237-244.

Epstein, "Cutaneous Wound Healing", New. Engl. J. Med. (1999), 341(10): 738-746.

European Search Report, 7 pages, EP appl. No. 10185428.9 dated Dec. 27, 2011.

European Search Report, 9 pages, EP appl. No. 10185372.9 dated May 25, 2011.

European Search Report, 9 pages, EP appl. No. 10185398.4 dated Dec. 23, 2011.

European Search Report, 7 pages, EP application No. 13755720.3, dated Dec. 9, 2015.

Evans and Martin, "Gap junctions: structure and function", Mol Membr Biol (2002), 19: 121-136.

Fanning et al., "Isolation and functional characterization of the actin binding region in the tight junction protein ZO-1", Faseb J (2002), 16: 1835-1837.

Fawcett and Asher. "The glial scar and central nervosystem repair", Brain Res. Bull. (1999), 49:377-391.

Fischer et al. "Structure-activity relationship of truncated and substituted analogues of the intracellular delivery vector Penetratin", J. Pept. Res. (2000), 55: 163-172.

Fishman et al. "Expression of connexin43 in the developing rat heart", Circulation Research (1991), 68: 782-287.

Fonseca et al. "Upregulation in astrocytic connexin 43 gap junction levels may exacerbate generalized seizures in mesial temporal lobe epilepsy", Brain Research (2002), 1: 105-116.

FrankeL and Pabo. "Cellular uptake of the Tat protein from human immunodeficiency Virus", Cell (1988), 55: 1189-1193.

Fromaget et al. "Changes in the expression of connexin 43, a cardiac gap junctional protein, during mouse heart development", J Mol Cell Cardiol. (1990), 22: 1245-1258.

Fromaget et al. "Distribution pattern of connexin 43, a gap junctional protein, during the differentiation of mouse heart myocytes", Differentiation (1992), 51: 9-20.

Fu et al. "CCN3 (NOV) interacts with Connexin43 in C6 glioma cells: possible mechanism of Connexin-mediated growth suppression", J Biol Chem. (2004), 279(35): 36943-36950 (2004).

Fujii et al. "A selective irreversible inhibitor targeting a PDZ protein interaction domain", J Am Chem Soc. (2003), 125(40): 12074-12075.

Gaietta et al. "Multicolor and electron microscopic imaging of connexin trafficking", Science (2002), 296: 503-507.

Gao et al. "A cell-penetrating peptide from a novel pVII-pIX phage-displayed random peptide library", Bioorg. Med. Chem. (2002), 10: 4057-4065.

Ghatnekar et al. "Connexin43 carboxyl-terminal peptides reduce scar progenitor and promote regenerative healing following skin wounding", Regen. Med. (2009), 4(2): 205-223.

(56) References Cited

OTHER PUBLICATIONS

Ghatnekar. "Novel Therapeutics for Regenerative Healing", FirstString Research Presentation (2010), 11 pages http://www.charlestondigitalcorridor.com/uploads/presentations/FSR_Presentation.pdf.
Ghatnekar. "Technical Report", 7 pages (Jul. 17, 2012).
Giepmans and Moolenaar, "The gap junction protein connexin43 interacts with the second PDZ domain of the zona occludens-1 protein", Curr. Biol. (1998), 8(16): 931-934.
Giepmans et al. "Gap junction protein connexin-43 interacts directly with microtubules", Curr Biol (2001), 11: 1364-1368.
Giepmans, B.N. "Gap junctions and Connexin-interacting proteins", Cardiovasc Res. (2004), 62(2): 233-245.
Gil-Parrado et al. "Calpastatin exon 1 B-derived peptide, a selective inhibitor of calpain: enhancing cell permeability by conjugation with penetratin", Biol Chem (2003), 384: 395-402.
Gonzalez-Mariscal et al. "Tight junction proteins", Prog Biophys Mol Biol (2003), 81: 1-44.
Goodenough and Paul. "Beyond the gap: functions of unpaired connexon channels", Nat Rev Mol Cell Biol (2003), 4: 285-294.
Gourdie et al. "Gap junction distribution in adult mammalian myocardium revealed by an anti-peptide antibody and laser scanning confocal microscopy", Journal of Cell Science (1991), 99: 41-55.
Gourdie et al. NIH Grant 5R01HL056728 (2011), 87 pages.
Gourdie et al. "The unstoppable connexin43 carboxyl-terminus: new roles in gap junction organization and wound Healing", Ann NY Acad Sci. (2006), 1080: 49-62.
Green and Loewenstein. "Autonomofunctional domains of chemically synthesized human immunodeficiency virtat trans-activator protein", Cell (1988), 55: 1179-1188.
Green et al. "Validation of immunohistochemical quantification in confocal scanning laser microscopy: A comparative assessment of gap junction size with confocal and ultrastructural techniques", Journal of Histochemistry and Cytochemistry (1993), 41: 1339-1349.
Gros et al. "Connexins in mammalian heart function", BioEssays (1996), 18: 719-730.
Gros et al. "Formation and growth of gap junctions in mouse myocardium during ontogenesis: a freeze-cleave study", J Cell Sci (1978), 30: 45-61.
Hall and Gourdi. "Spatial organization of cardiac gap junctions can affect access resistance", Microsc Res Tech (1995), 31: 446-451.
Harris, A.L. "Emerging issues of connexin channels: biophysics fills the gap", Q Rev Biophys (2001), 34:325-472.
Hawat et al. "Connexin 43 mimetic peptide Gap26 confers protection to intact heart against myocardial ischemia injury", Pflugers Arch.—Eur. J. Physiol. (2010), 460(3): 583-592.
Hayashi et al. "Cooperative effects of v-myc and c-Ha-ras oncogenes on gap junctional intercellular communication and tumorigenicity in rat liver epithelial cells", Cancer Lett. (1998), 128: 145-154.
Hayashi et al. "Inhibition of gap junctional intercellular communication in rat liver epithelial cells with transforming RNA", FEBS Lett. (2001), 491: 200-206.
Hayashi et al. "Stimulation of cell proliferation and inhibition of gap junctional intercellular communication by linoleic acid", Cancer Lett. (1997), 112: 103-111.
Hilton et al., "Wound Dressings in Diabetic Foot Disease," Clinical Infectious Diseases, 2004;39:S100-103.
Hodgins, "Connecting wounds with Connexins", J. Invest. Derm. (2004), 122: ix-x.
Hong and Clayman. "Isolation of a peptide for targeted drug delivery into human head and neck solid tumors", Cancer Res. (2000), 60: 6551-6556.
Hunter et al. "Fusion of GFP to the carboxyl terminof connexin43 increases gap junction size in HeLa cells", Cell Commun Adhes. (2003), 10(4-6): 211-214.
Hunter et al. "Zonula occludens-1 alters connexin43 gap junction size and organization by influencing channel accretion", Mol Biol Cell. (2005), 16: 5686-98. Epub Sep. 29, 2005.

Hutchinson and Hayden. "The prediction of exons through an analysis of spliceable open reading frames", Nucl. Acids Res. (1992), 20(13): 3453-3462.
Hutnik et al., "The Protective Effect of Functional Connexin43 Channels on a Human Epithelial Cell Line Exposed to Oxidative Stress", Invest. Ophthalmol. Visual Sci. (2008), 49(2): 800-806.
International Search Report, 4 pages, PCT appl. No. PCT/US2005/046442 (dated Mar. 26, 2007).
International Search Report and Writen Opinion, PCT/US08/67944, dated Dec. 12, 2008.
International Search Report and Written Opinion, PCT/US2013/028727 dated May 30, 2013).
International Preliminary Reporton Patentability, PCT/US2013/028727 (dated Sep. 2, 2014).
Itoh et al., "Involvement of ZO-1 in cad herin-based cell adhesion through its direct binding to alpha catenin and actin filaments", J Cell Biol (1997), 138: 181-192.
Jin and Lau. "Identification of connexin-interacting proteins: application of the yeast two-hybrid screen", Methods (2000), 20: 219-231.
Johnson et al. "Gap junctions assemble in the presence of cytoskeletal inhibitors, but enhanced assembly requires microtubules", Experimental Cell Research (2002), 275: 67-80.
Jordan et al. "Trafficking, assembly, and function of a connexin43-green fluorescent protein chimera in live mammalian cells", Mol Biol Cell (1999), 10: 2033-2050.
Kajstura et al. "Bone marrow cells differentiate in cardiac cell lineages after infarction independently of cell fusion", Circ Res. (2005), 96(1):127-37.
Kanovsky et al. "Peptides from the amino terminal mdm-2-binding domain of p53, designed from conformational analysis, are selectively cytotoxic to transformed cells", Proc Natl Acad Sci USA (2001), 98: 12438-12443.
Kaprielian et al. "Downregulation of immunodetectable connexin43 and decreased gap junction size in the pathogenesis of chronic hibernation in the human left ventricle", Circulation (1998), 97: 651-660.
Kausalya et al. "Association of ARVCF with zonula occludens (ZO)-1 and ZO-2: binding to PDZ-domain proteins and cell-cell adhesion regulate plasma membrane and nuclear localization of ARVCF", Mol Biol Cell. (2004), 15(12): 5503-5515. Epub Sep. 29, 2004.
Kausalya et al. "Connexin45 directly binds to ZO-1 and localizes to the tight junction region in epithelial MDCK cells", FEBS Letters (2001), 505: 92-96.
Kumar and Gilula. "The gap junction communication channel", Cell (1996), 84: 381-388.
Kwak et al. "Inhibition of endothelial wound repair by dominant negative connexin inhibitors", Mol Biol Cell. (2001), 12(4): 831-845.
Laing et al., "Connexin45 interacts with zonula occludens-1 and connexin43 in osteoblastic cells", J Biol Chem (2001), 276: 23051-23055.
Laird et al., "Expression and imaging of connexin-GFP chimeras in live mammalian cells", Methods Mol Biol (2001), 154: 135-142.
Lampe and Lau. "Regulation of gap junctions by phosphorylation of connexins", Arch Biochem Biophys (2000), 384: 205-215.
Lauf et al. "Dynamic trafficking and delivery of connexons to the plasma membrane and accretion to gap junctions in living cells", Proc Natl Acad Sci USA (2002), 99: 10446-10451.
Lauf et al. "Expression of fluorescently tagged connexins: a novel approach to rescue function of oligomeric DsRed-tagged proteins", FEBS Lett (2001), 498: 11-15.
Legato, M.J. "Cellular Mechanisms of Normal Growth in the Mammalian Heart I. Qualitative and Quantitative Features of Ventricular Architecture in the Dog from Birth to Five Months of Age", Circulation Research (1979), 44: 250-262.
Li et al. "Neuronal connexin36 association with zonula occludens-1 protein (ZO-1) in mouse brain and interaction with the first PDZ domain of ZO-1", Eur J Neurosci. (2004), 19(8): 2132-2146.

(56) References Cited

OTHER PUBLICATIONS

Lin et al. "Inhibition of nuclear translocation of transcription factor NF-KB by a synthetic peptide containing a cell membranepermeable motif and nuclear localization sequence", J. Biol. Chem. (1995), 270: 14255-14258.
Liu et al. "A structural basis for the unequal sensitivity of the major cardiac and liver gap junctions to intracellular acidification: the carboxyl tail length", Biophys J (1993), 64: 1422-1433.
Lo, C.W. Role of gap junctions in cardiac conduction and development: insights from the connexin knockout mice. Circulation Research (2000), 87: 346-348.
Lundberg et al. "Cell membrane translocation of the N-terminal (1-28) part of the prion protein", Biochem. Biophys. Res. Commun. (2002), 299: 85-90.
Mambettsaeva et al. "Expression of Three Functional Domains of Connexin 32 as Thioredoxin Fusion Proteins in *Escherichia coli* and Generation of Antibodies", Prot. Express. Purif. (1997), 11: 26-34.
Martin, P. "Wound healing—aiming for perfect skin regeneration", Science (1997), 276(5309): 75-81.
Matsushita et al. "Photo-acceleration of protein release from endosome in the protein transduction system", FEBS Lett. (2004), 572: 221-226.
Merrifield et al. "Endocytic vesicles move at the tips of actin tails in cultured mast cells", Nat Cell Biol (1999), 1: 72-74.
Mitic and Anderson. "Molecular architecture of tight junctions", Annu Rev Physiol (1998), 60: 121-142.
Moorby, C.D. "A connexin 43 mutant lacking the carboxyl cytoplasmic domain inhibits both growth and motility of mouse 3T3 fibroblasts", Mol Carcinog. (2000), 28(1):23-30.
Morris et al. "A peptide carrier for the delivery of bioloically active proteins into mammalian cells", Nature Biotechnol. (2001), 19: 1173-1176.
Moyer et al. "Wound healing: the role of gap junctional communication in rat granulation tissue maturation", Exp. Mol. Pathol. (2002), 72: 10-16.
Murray et al. "Relationship of cytoskeletal filaments to annular gap junction expression in human adrenal cortical tumor cells in culture", Exp Cell Res (1997), 234: 398-404.
Musil and Goodenough. "Biochemical analysis of connexin43 intracellular transport, phosphorylation, and assembly into gap junctional plaques", J Cell Biol (1991), 115: 1357-1374.
Nielsen et al. "Lens connexins alpha3Cx46 and alpha8Cx50 interact with zonula occludens protein-1 (ZO-1)", Mol Biol Cell. (2003), 14(6):2470-2481. Epub Mar. 7, 2003.
Norenberg, M.D. "Astrocyte responses to CNS injury", J. Neuropathol. Exp. Neurol. (1994), 53:213-220.
Occleston et al., "New therapeutics for the prevention and reduction of scarring." Drug Discovery Today (2008); 13(21): 973-981.
Oehlke et al. "Cellular uptake of an α-helical amphipathic model peptide with the potential to deliver polar compounds into the cell interior non-endocytically", Biochim. Biophys. Acta. (1998), 1414: 127-139.
O'Quinn et al. "A peptide mimetic of the connexin43 carboxyl terminreduces gap junction remodeling and induced arrhythmia following ventricular injury", Circ. Res. (2011), 108(6): 704-715. Epub Jan. 27, 2011.
Orlandini and Margaria. "Evaluation of the efficiency of a new hollow fiber plasmapheresis filter", Int J Artif Organs (1983), 6(Suppl 1): 103-106.
Park et al. "Structure-activity analysis of buforin II, a histone H2A-derived antimicrobial peptide: the proline hinge is responsible for the cell-penetrating ability of buforin II", Proc. Natl Acad. Sci. USA (2000), 97: 8245-8250.
Partial European Search Report, 5 pages, EP appl. No. 10185428.9 (dated Sep. 6, 2011).
Partial European Search Report, 6 pages, EP appl. No. 10185372.9 (dated Jan. 21, 2011).
Partial European Search Report, 7 pages, EP appl. No. 10185398.4 (dated Sep. 6, 2011).
Pich et al. "Prognostic relevance of cell proliferation in head and neck tumors", Annals of Oncology (2004), 15(9): 1319-1329.
Pooga et al. "Cell penetration by transportan", FASEB J. (1998), 12: 67-77 (1998).
Poss et al. "Heart regeneration in zebrafish", Science (2002), 298(5601): 2188-2190 (2002).
Prochiantz, A. "Homeodomain-derived peptides. In and out of the cells", Ann NY Acad Sci (1999), 886: 172-179.
Qiu et al. "Targeting connexin43 expression accelerates the rate of wound repair", Curr Biol. (2003), 13(19): 1697-703.
Rhett et al., "Novel therapies for scar reduction and regenerative healing of skin wounds." Trends in Biotechnology (2008); 26(4): 173-180.
Rousselle et al. "New advances in the transport of doxorubicin through the bloodbrain barrier by a peptide vector-mediated strategy", Mol. Pharmacol. (2000), 57(4): 679-686.
Saitongdee et al. "Increased connexin43 gap junction protein in hamster cardiomyocytes during cold acclimatization and hibernation", Cardiovasc Res (2000), 47: 108-115.
Sawada et al. "Cytoprote.ctive membrane-permeable peptides designed from the Bax-binding domain of Ku70", Nature Cell Biol. (2003), 5: 352-357.
Segretain and Falk. "Regulation of connexin biosynthesis, assembly, gap junction formation, and removal", Bioch. Bioph. Acta (2004), 1662: 3-21.
Segretain et al. "A proposed role for ZO-1 in targeting connexin 43 gap junctions to the endocytic pathway", Biochimie. (2004), 86: 241-244.
Sepp et al. "Altered patterns of cardiac intercellular junction distribution in hypertrophic cardiomyopathy", Heart (1996), 76: 412-417.
Severs et al. "Remodelling of gap junctions and connexin expression in heart disease", Biochim Biophys Acta. (2004), 1662: 138-148.
Shibata et al. "Ultrastructual changes during development of gap junctions in rabbit left ventricular myocardial cells", Journal of Ultrastructure Research (1980), 71: 258-271.
Silver and Miller. "Regeneration beyond the glial scar", Nat Rev Neurosci. (2004), 5(2): 146-156.
Simpson et al. "Modulation of cardiac myocyte phenotype in vitro by the composition and orientation of the extracellular matrix", Journal of Cellular Physiology (1994), 161: 89-105.
Singapore Application No. 11201405359Y, Search Report dated Sep. 10, 2015, 3 pages.
Singapore Application No. 11201405359Y, Written Opinion dated Sep. 10, 2015, 7 pages.
Singapore Application No. 11201405359Y, Written Opinion dated Apr. 11, 2016, 4 pages.
Smith et al. "Altered patterns of gap junction distribution in ischemic heart disease. An immunohistochemical study of human myocardium using laser scanning confocal microscopy", American Journal of Pathology (1991), 139: 801-821.
Songyang et al. "Recognition of unique carboxyl-terminal motifs by distinct PDZ domains", Science (1997), 275: 73-77.
Spach et al. "Electrophysiological effects of remodeling cardiac gap junctions and cell size: experimental and model studies of normal cardiac growth", Circulation Research (2000), 86: 302-311.
Spach, M.S. "Transition from a continuous to discontinuous understanding of cardiac conduction", Circ Res. (2003), 92(2): 125-126.
Stergiopoulos et al. "Hetero-Domain Interactions as a Mechanism for the Regulation of Connexin Channels", Circ. Res. (1999), 84:1144-1155.
Stevenson et al. "Identification of ZO-1: a high molecular weight polypeptide associated with the tight junction (zonula occludens) in a variety of epithelia", J Cell Biol (1986), 103: 755-766.
Sullivan and Lo. "Expression of a connexin 43/beta-galactosidase fusion protein inhibits gap junctional communication in NIH3T3 cells", J Cell Biol. (1995), 130(2): 419-429.
Supplementary European Search Report, 9 pages, EP appl. No. 08771766.6 (dated Jul. 4, 2012).
Thomas et al. "Role of cytoskeletal elements in the recruitment of Cx43-GFP and Cx26-YFP into gap junctions", Cell Commun Adhes (2001), 8: 231-236.

(56) References Cited

OTHER PUBLICATIONS

Toyofuku et al. "c-Src regulates the interaction between connexin-43 and ZO-1 in cardiac myocytes", J Biol Chem. (2001), 276(3): 1780-1788. Epub Oct. 16, 2000.
Toyofuku et al. "Direct association of the gap junction protein connexin-43 with ZO-1 in cardiac myocytes", J Biol Chem. (1998), 273(21): 12725-12731.
Traub et al. "Characterization of the gap junction protein connexin37 in murine endothelium, respiratory epithelium, and after transfection in human HeLa cells", Eur. J. Cell Biol. (1998), 77:313-322.
Tsao et al. "A diploid epithelial cell line from normal adult rat liver with phenotypic properties of 'oval' cells", Exp. Cell Res. (1984), 154:38-52.
UniProtKB/Swiss-Prot P17302, downloaded Mar. 11, 2010, 16 pages. http://www.uniprot.org/uniprot/P17302.html.
Vigneron et al. "Guanidinium-cholesterol cationic lipids: Efficient vectors for the transfection of eukaryotic cells", Proc. Natl. Acad. Sci. USA. (1998), 93: 9682-9686.
Wadia et al. "Transducible TAT-HA fusogenic peptide enhances escape of TAT-fusion proteins after lipid raft macropinocytosis", Nat Med. (2004), 10(3): 310-315.
Wender et al. "The design, synthesis, and evaluation of molecules that enable or enhance cellular uptake: Peptoid molecular transporters", Proc. Natl. Acad. Sci. USA (2000), 97(24): 13003-13008.
Weymarn, "Process Development for Mannitol Production by Lactic Acid Bacteria", Helinski University of Technology Department of Chemical Technology, Laboratory of Bioprocess Engineering. Technical Biochemistry Report Jan. 2002. Dissertation Apr. 12, 2002.
Wilgus et al. "Reduction of scar formation in full-thickness wounds with topical celecoxib treatment", Wound Rep Reg (2003), 11: 25-34.
Willecke et al. "Mouse Connexin37: Cloning and Functional Expression of a Gap Junction Gene Highly Expressed in Lung", J. Cell Biol. (1991), 114(5): 1049-1057.
Wright et al. "The connexin mimetic peptide Gap27 increases human dermal fibroblast migration in hyperglycemic and hyperinsulinemic conditions in vitro", Cell Physiol. (2011), 227(1): 77-87. Epub Feb. 24, 2011.
Written Opinion of the International Searching Authority, 7 pages, PCT appl. No. PCT/US2005/046442 (dated Mar. 26, 2007).
Wu et al., "Use of Pressure Offloading Devices in Diabetic Fool Ulcers," Diabetes Care, Nov. 2008, 31 (11):2118-2119.
Yoo, D.S. "The dielectric properties of cancerotissues in a nude mouse xenograft model", Bioelectromagnetics (2004), 25(7): 492-497.
Zarbin. "Current Concepts in the Pathogenesis of Age-Related Macular Degeneration",Arch. Ophthalmol. (2004), 122(4):598-614.
Zhang et al., "The Gap Junction-independent Tumor-suppressing Effect of Connexin 43", J. Biol. Chem. (2003), 278(45): 44852-44856.
Zhu et al. "Quantitative Analysis of ZO-1 Co-Localization with Cx43 Gap Junction Plaques in Cultures of Rat Neonatal Cardiomyocytes", Microsc Microanal. (2005), 11(3): 244-248.

* cited by examiner

Figure 2 Subject Self Assessment of Pain ITT Population (N=91)
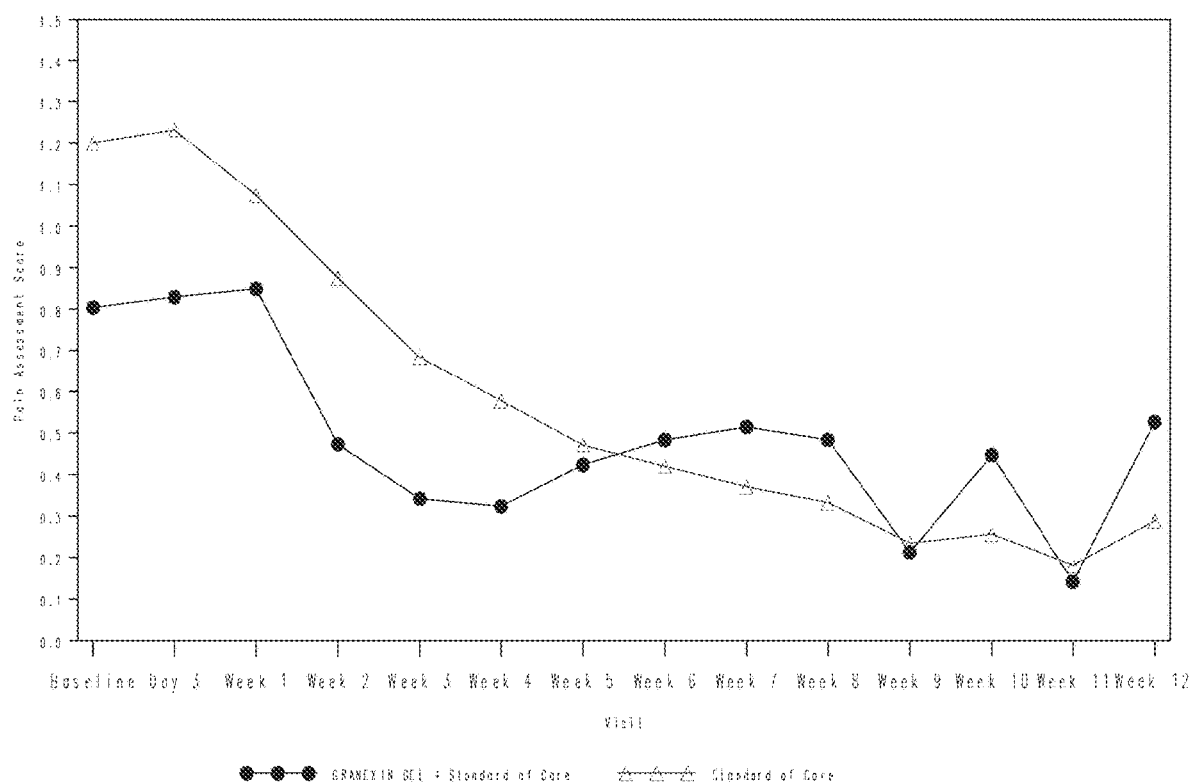

Figure 3  Subject Self Pain Assessment PP Population (N = 60)
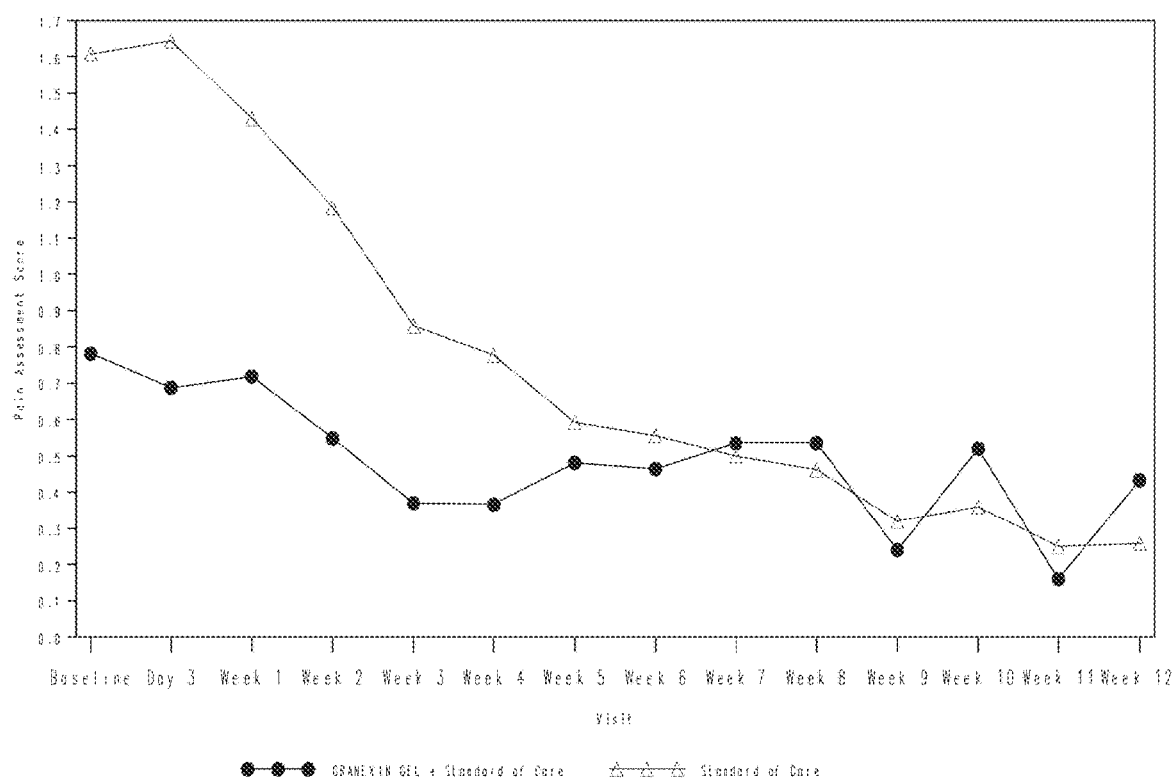

Figure 4 Kaplan-Meier Plot of Time to 100 % Wound Closure ITT Population (N = 91)
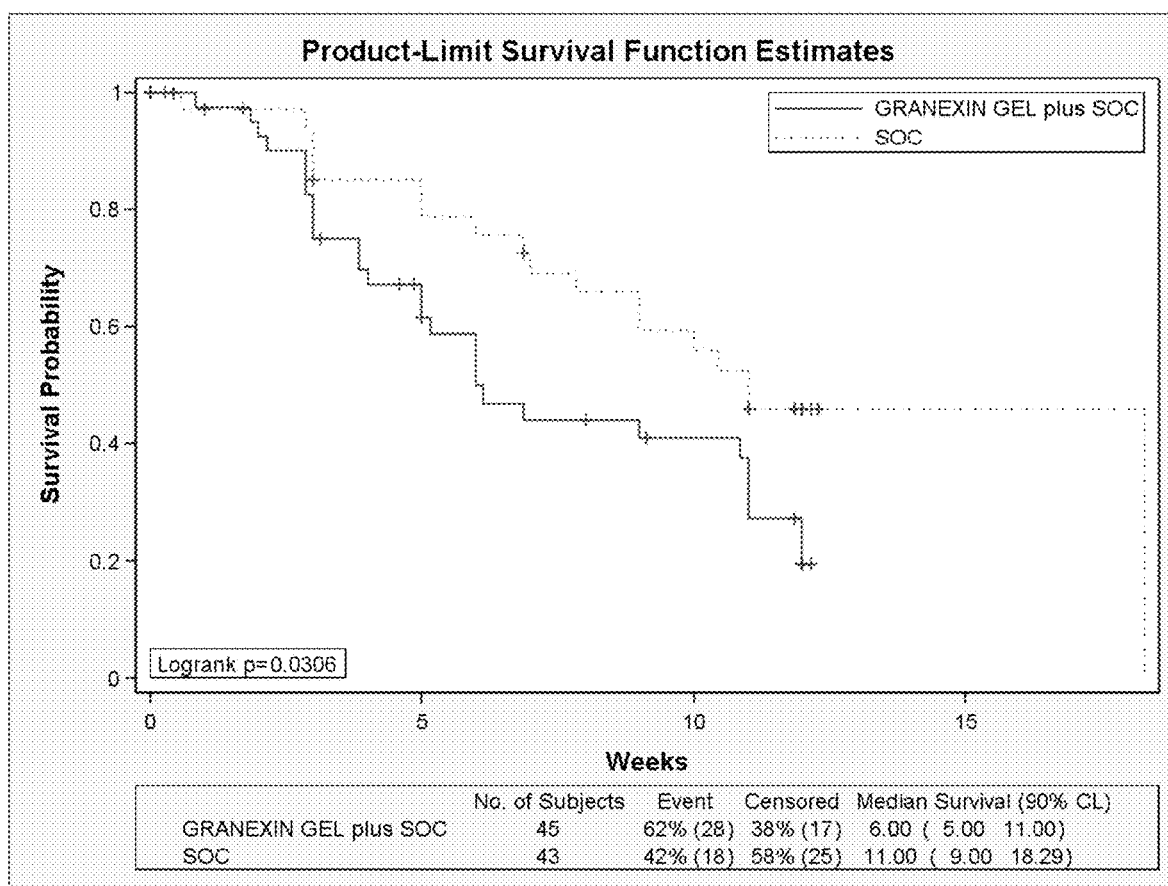

Figure 5    Kaplan-Meier Plot of Time to 100 % Wound Closure PP Population (N = 60)
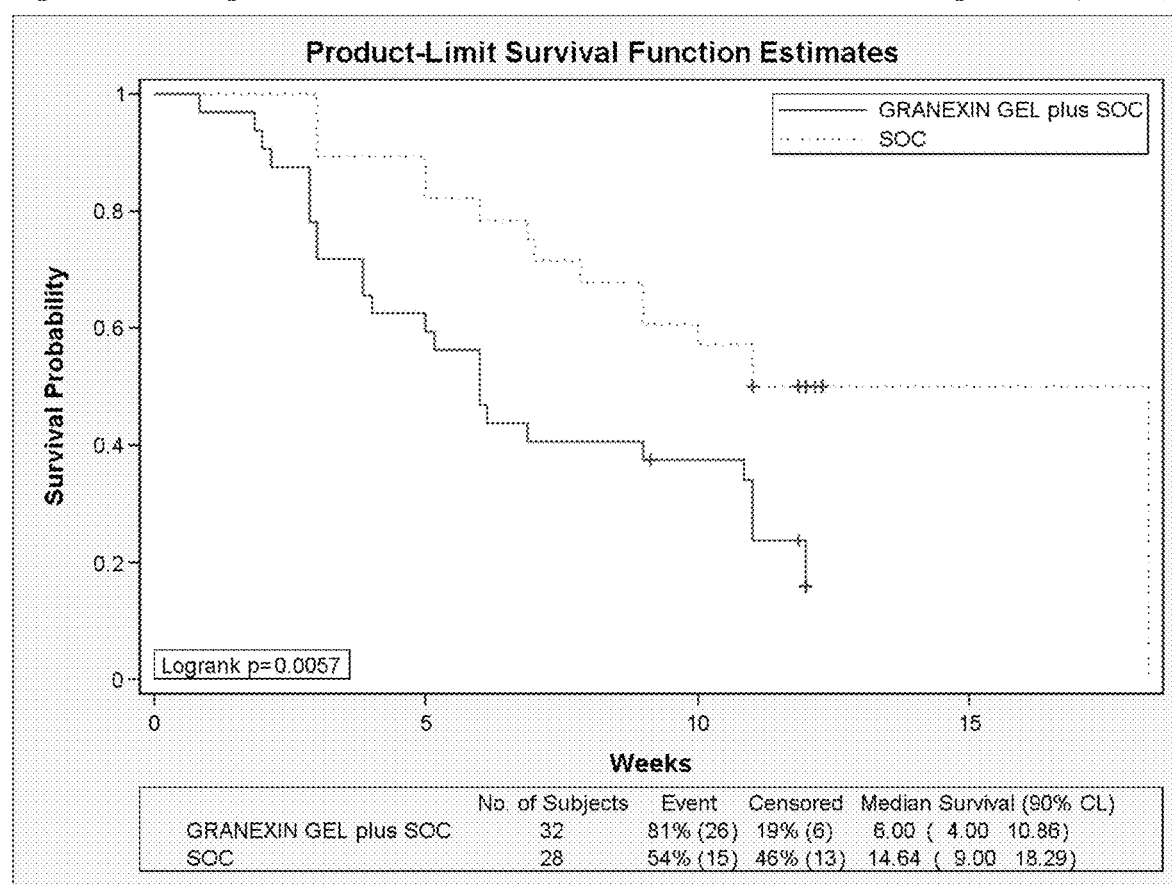

Figure 6 Kaplan-Meier Plot of Time to 50 % Wound Closure ITT Population (N = 91)
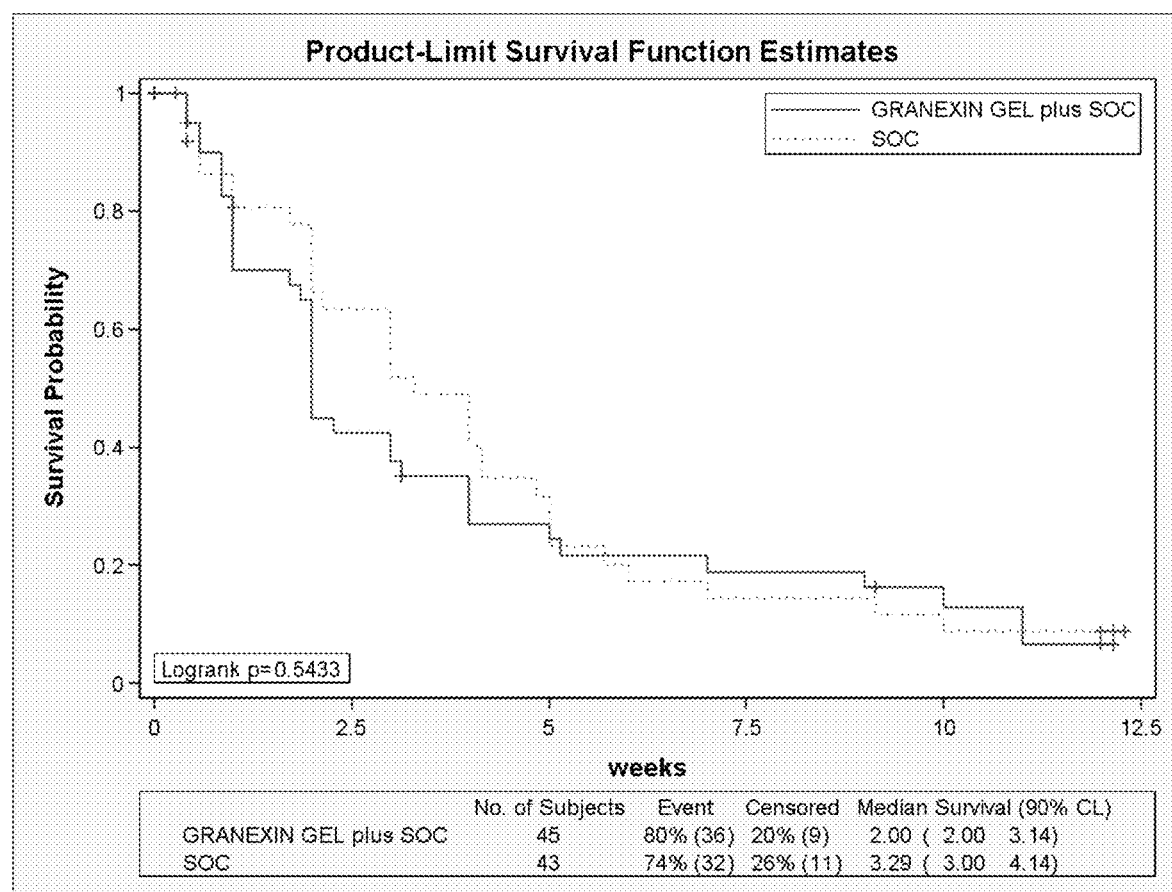

Figure 7     Kaplan-Meier Plot of Time to 50 % Wound Closure PP Population (N = 60)
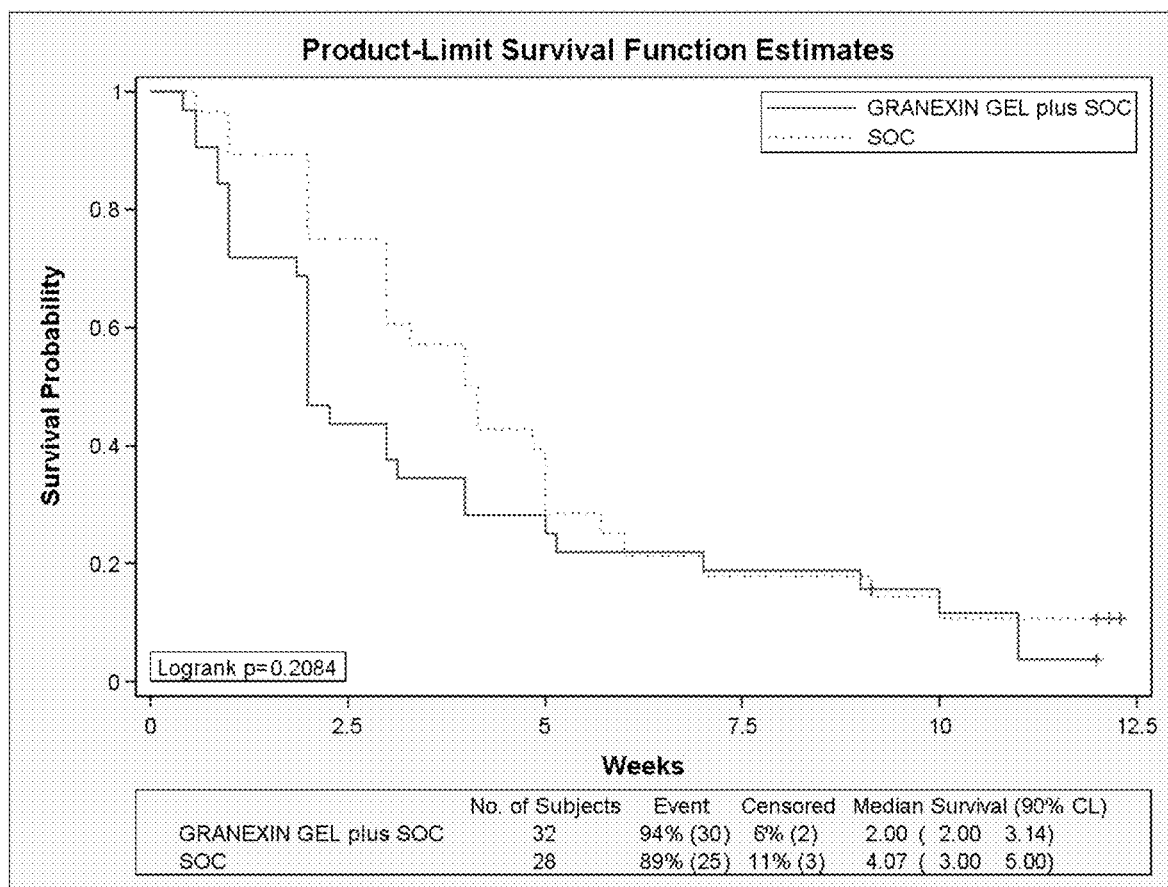

Figure 8    Average Wound Closure at All Visits ITT Population (N = 91)
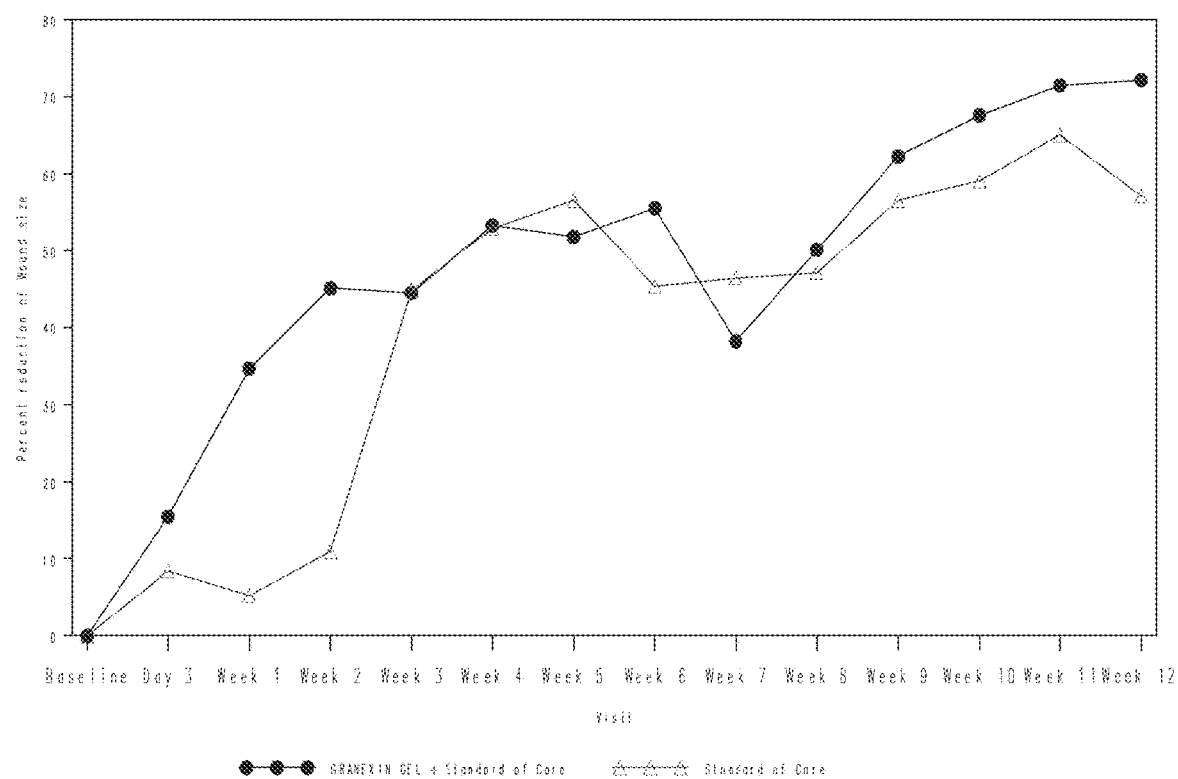

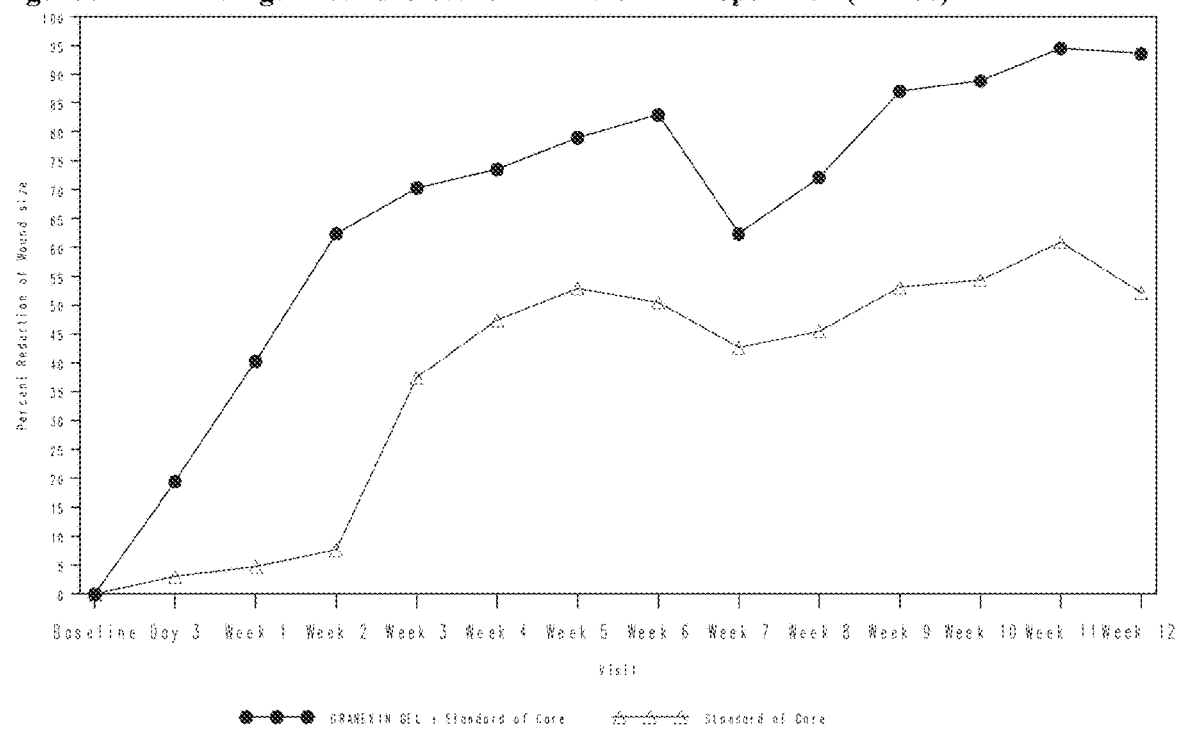
Figure 9  Average Wound Closure at All Visit PP Population (N = 60)

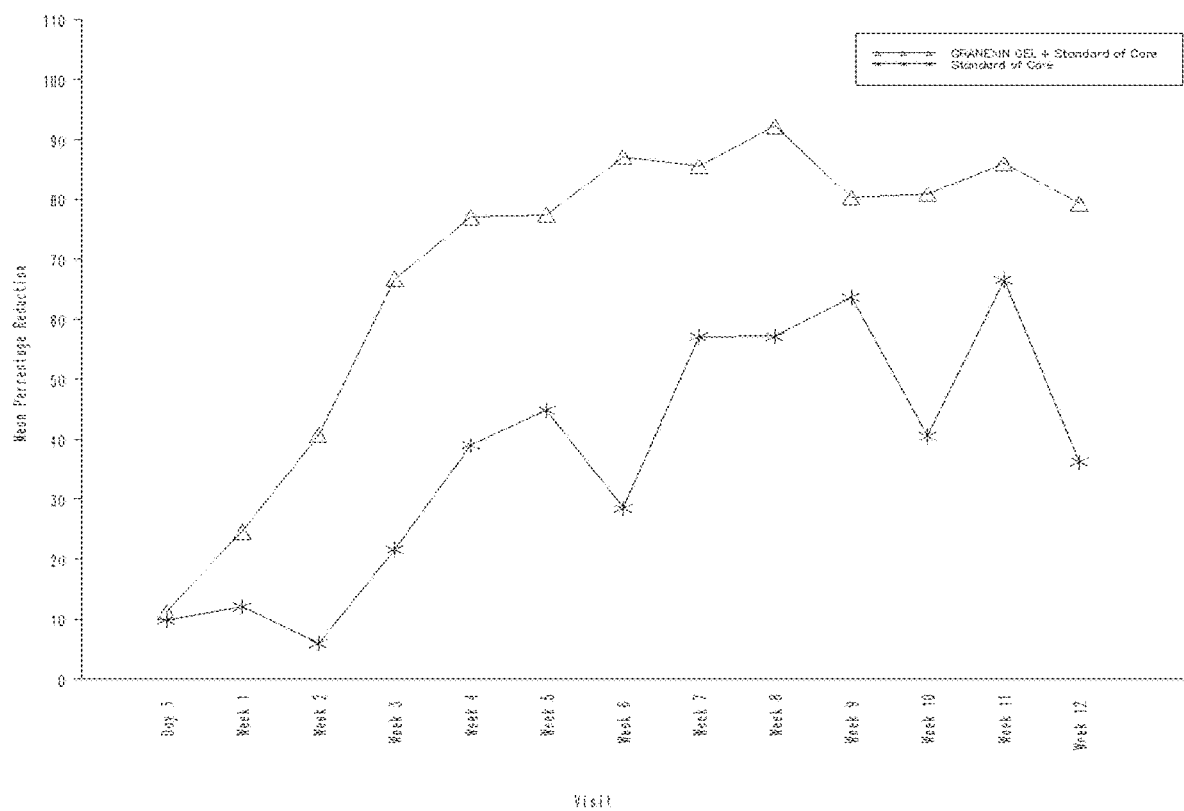
Figure 10 Longitudinal Response Profile of the Mean Percent Reduction of Wound Area (mm$^2$) from Baseline to Week 12 by Treatment Group - ITT Population (N=92)

Figure 11 Longitudinal Response Profile of the Mean Percentage Reduction of Wound Area from Baseline to Week 12 by Treatment Group - mITT Population (N=77)
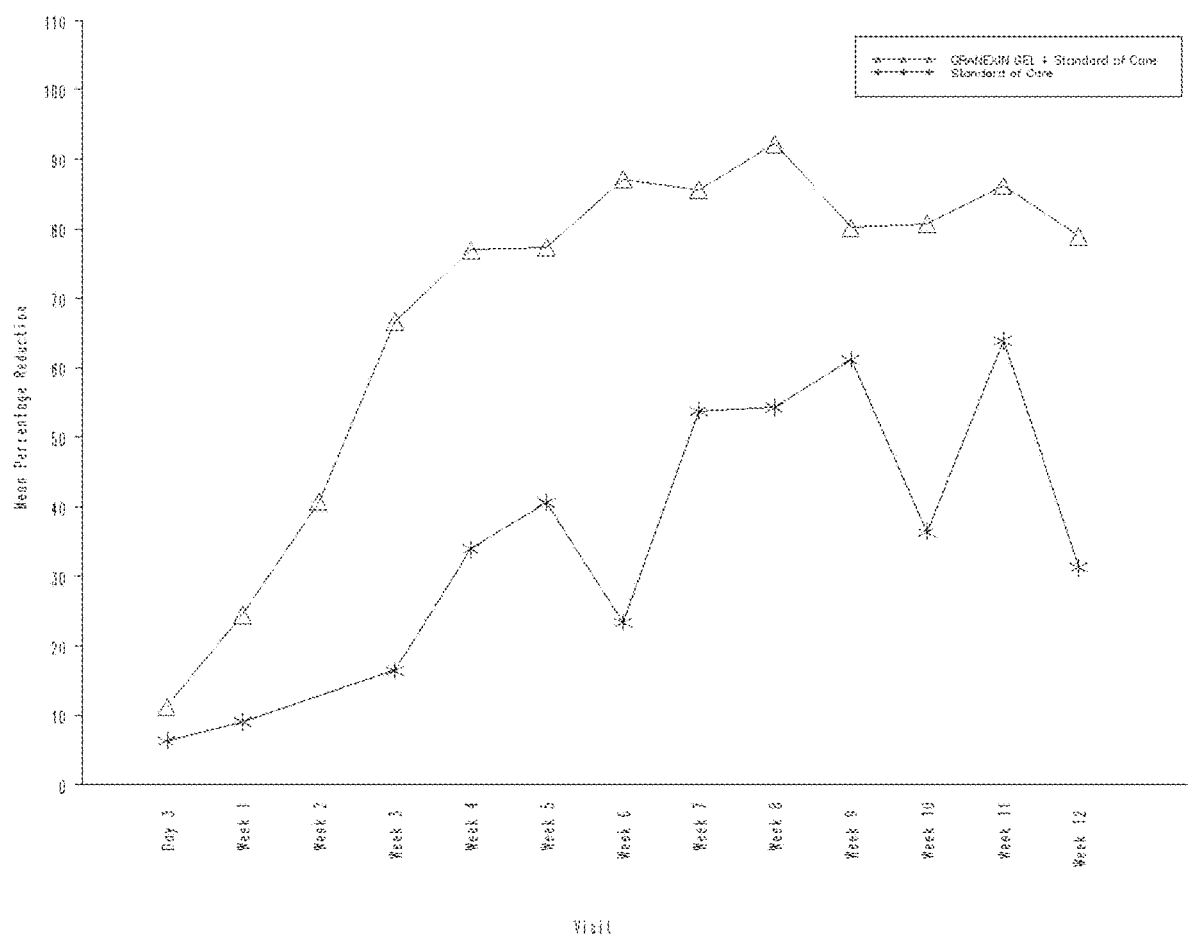

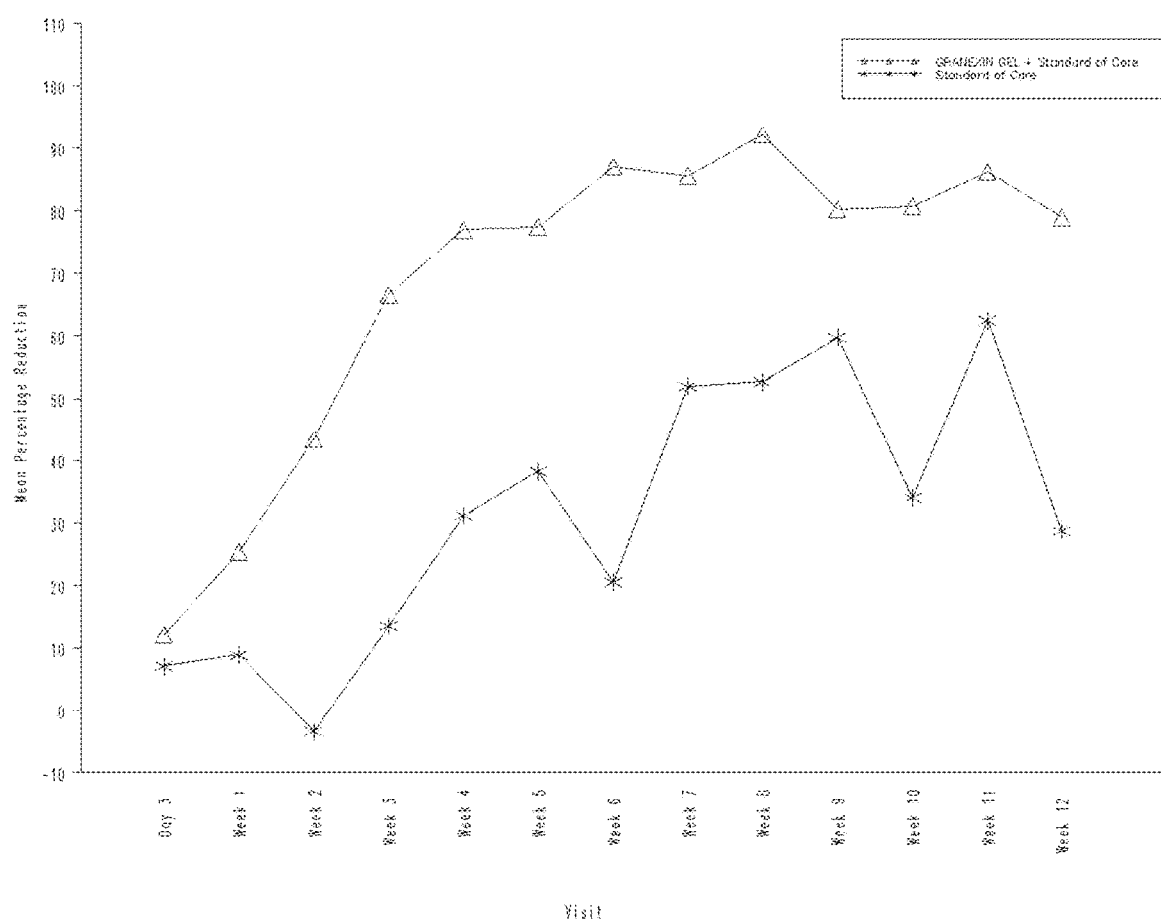
Figue 12 Longitudinal Response Profile of the Mean Percentage Reduction of Wound Area (mm$^2$) from Baseline to Week 12 by Treatment Group - PP Population (N=68)

Figure 13 Kaplan-Meier Plot of Time to First 100 % Wound Closure ITT Population (N = 92)
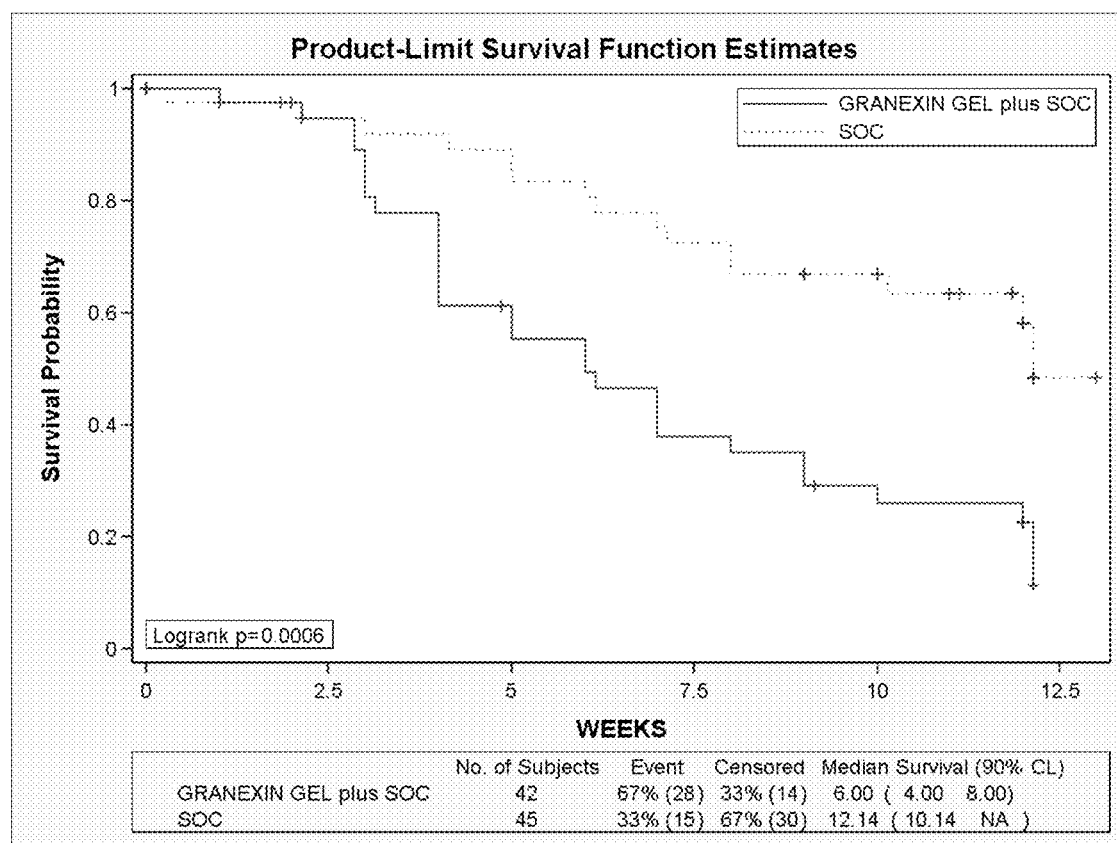

Figure 14 Kaplan-Meier Plot of Time to 100% Wound Closure - mITT Population (N=77)
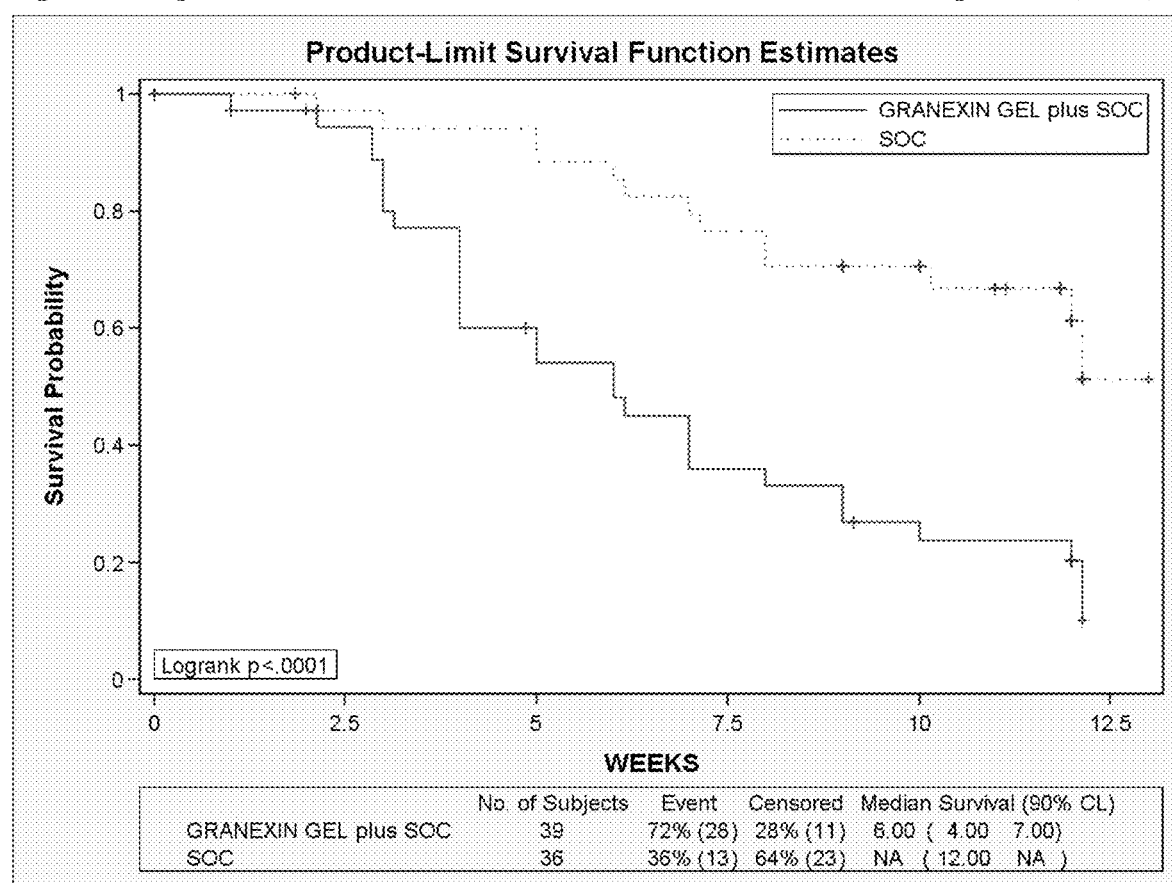

Figure 15 Kaplan-Meier Plot of Time to First 100 % Wound Closure PP Population (N = 68)
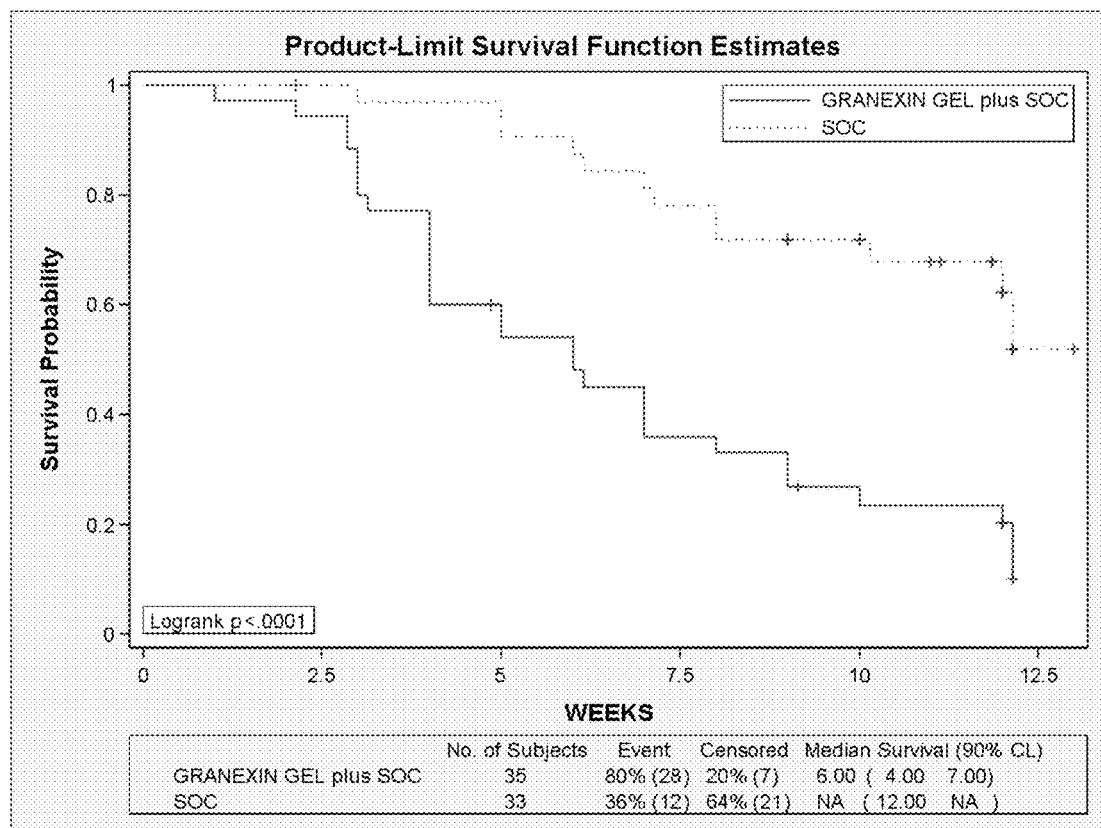

Figure 16 Kaplan-Meier Plot of Time to First 50 % Wound Closure ITT Population (N = 92)
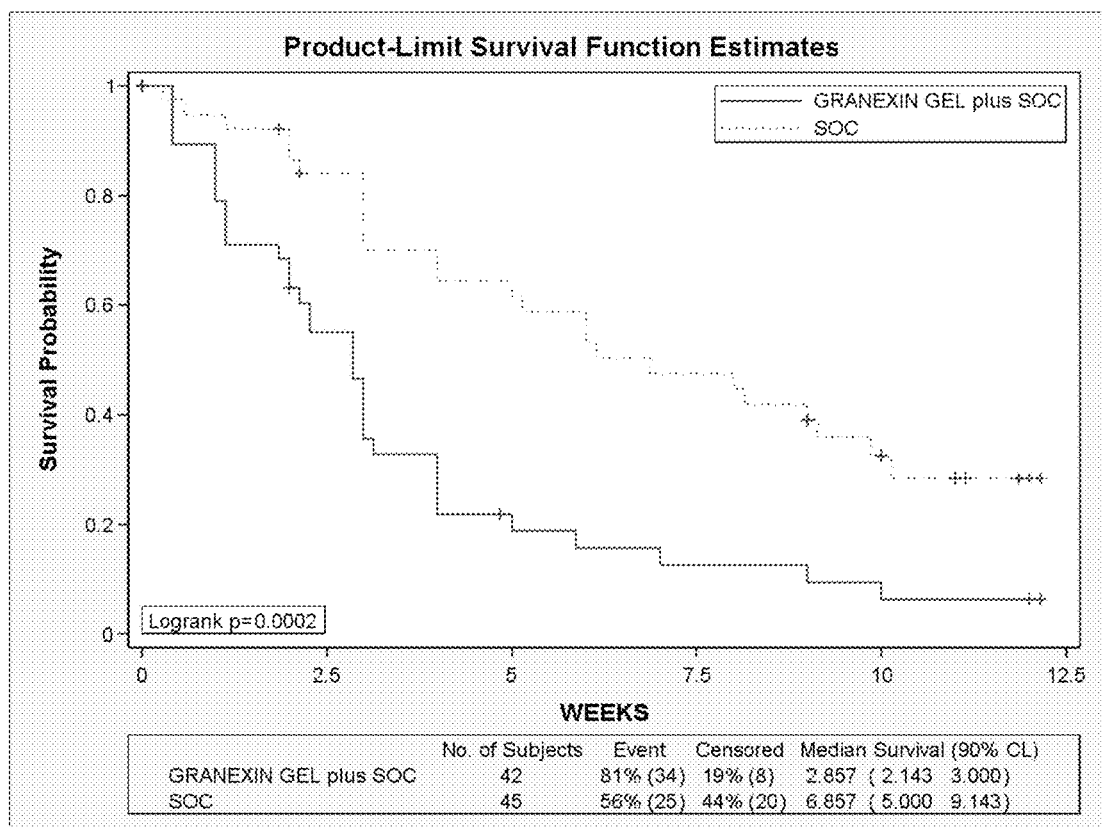

Figure 17 Kaplan-Meier Plot of Time to 50% Wound Closure - mITT Population (N=77)
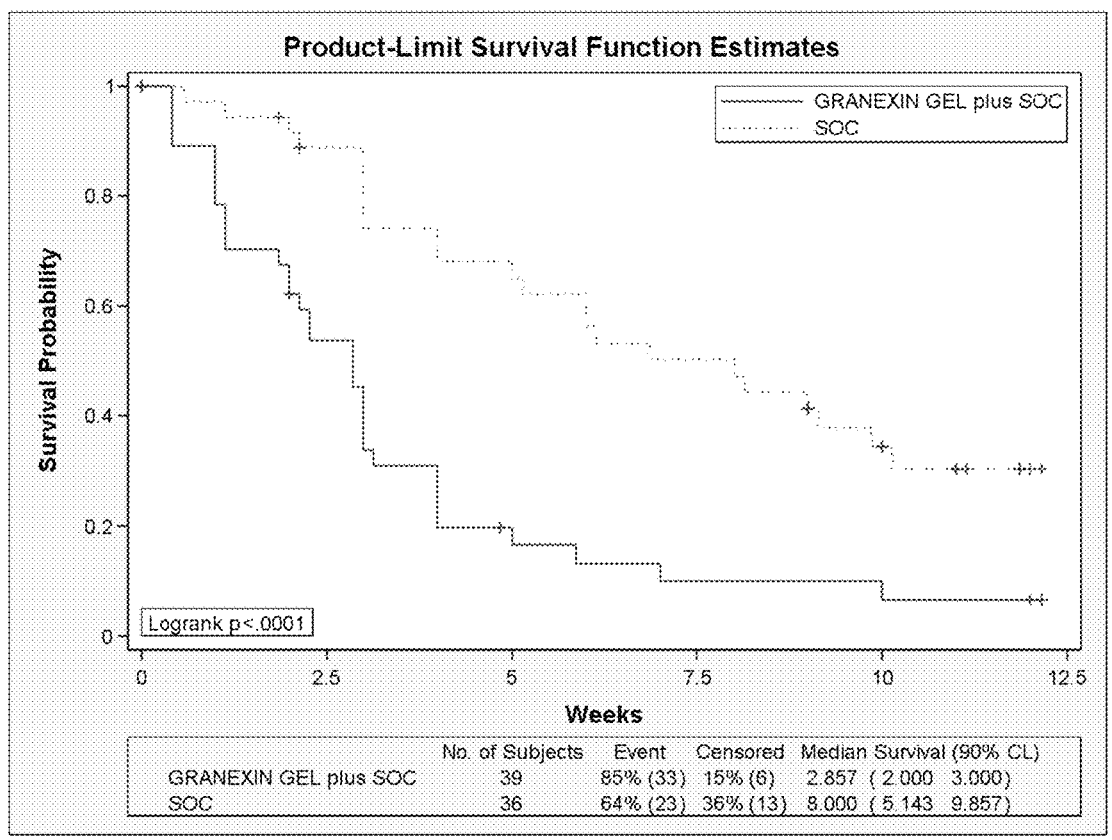

Figure 18 Kaplan-Meier Plot of Time to First 50 % Wound Closure PP Population (N = 68)
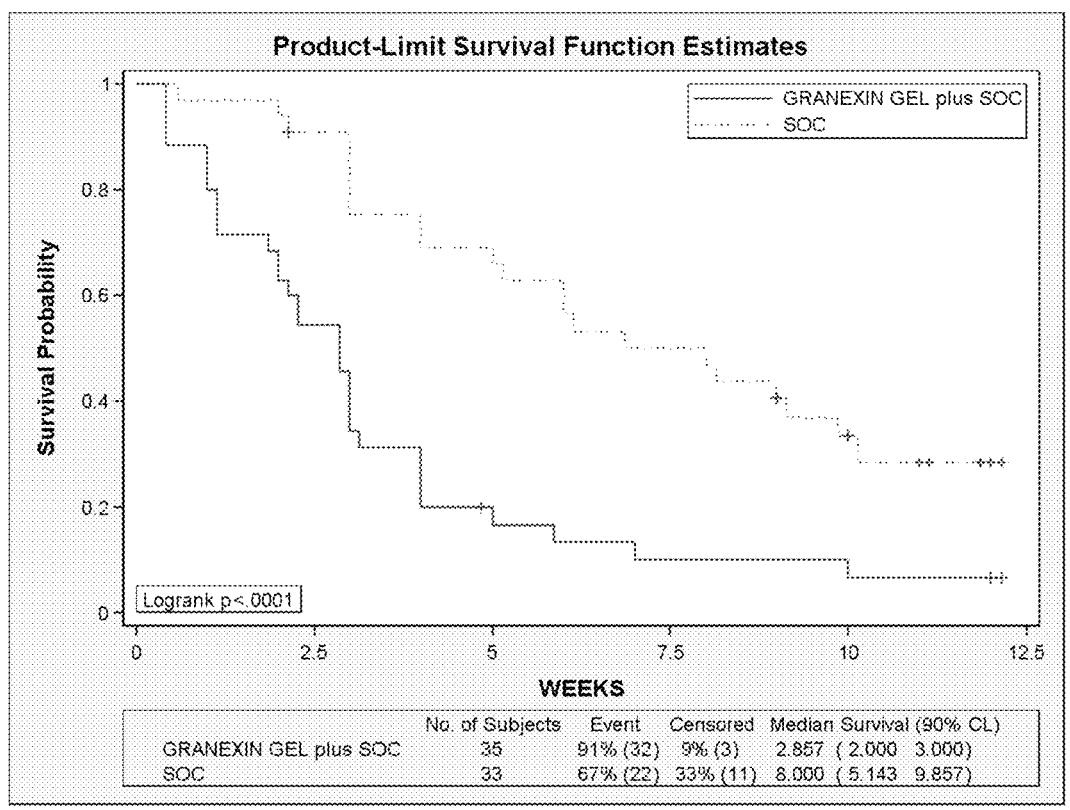

SEQUENCE LISTING

```
<160> NUMBER OF SEQ ID NOS: 92

<210> SEQ ID NO 1
<211> LENGTH: 20
<212> TYPE: PRT
<213> ORGANISM: Homo sapiens

<400> SEQUENCE: 1

Pro Ser Ser Arg Ala Ser Ser Arg Ala Ser Ser Arg Pro Arg Pro Asp
1               5                   10                  15

Asp Leu Glu Ile
            20

<210> SEQ ID NO 2
<211> LENGTH: 9
<212> TYPE: PRT
<213> ORGANISM: Homo sapiens

<400> SEQUENCE: 2

Arg Pro Arg Pro Asp Asp Leu Glu Ile
```

```
1               5

<210> SEQ ID NO 3
<211> LENGTH: 9
<212> TYPE: PRT
<213> ORGANISM: Artificial Sequence
<220> FEATURE:
<223> OTHER INFORMATION: mutated ACT 3 peptide sequence

<400> SEQUENCE: 3

Arg Pro Arg Pro Asp Asp Leu Glu Val
1               5

<210> SEQ ID NO 4
<211> LENGTH: 9
<212> TYPE: PRT
<213> ORGANISM: Artificial Sequence
<220> FEATURE:
<223> OTHER INFORMATION: mutated ACT 4 peptide sequence

<400> SEQUENCE: 4

Arg Pro Arg Pro Asp Asp Val Pro Val
1               5

<210> SEQ ID NO 5
<211> LENGTH: 9
<212> TYPE: PRT
<213> ORGANISM: Artificial Sequence
<220> FEATURE:
<223> OTHER INFORMATION: mutated ACT 5 peptide sequence

<400> SEQUENCE: 5

Lys Ala Arg Ser Asp Asp Leu Ser Val
1               5

<210> SEQ ID NO 6
<211> LENGTH: 27
<212> TYPE: DNA
<213> ORGANISM: Homo sapiens

<400> SEQUENCE: 6
agacctcggc ctgatgacct ggagatt                                      27

<210> SEQ ID NO 7
<211> LENGTH: 16
<212> TYPE: PRT
<213> ORGANISM: Drosophila melanogaster

<400> SEQUENCE: 7

Arg Gln Pro Lys Ile Trp Phe Pro Asn Arg Arg Lys Pro Trp Lys Lys
1               5                   10                  15

<210> SEQ ID NO 8
<211> LENGTH: 36
<212> TYPE: PRT
<213> ORGANISM: Artificial Sequence
<220> FEATURE:
<223> OTHER INFORMATION: Antp/ACT 2 fusion peptide sequence

<400> SEQUENCE: 8

Arg Gln Pro Lys Ile Trp Phe Pro Asn Arg Arg Lys Pro Trp Lys Lys
1               5                   10                  15

Pro Ser Ser Arg Ala Ser Ser Arg Ala Ser Ser Arg Pro Arg Pro Asp
            20                  25                  30

Asp Leu Glu Ile
```

```
<210> SEQ ID NO 9
<211> LENGTH: 25
<212> TYPE: PRT
<213> ORGANISM: Artificial Sequence
<220> FEATURE:
<223> OTHER INFORMATION: Antp/ACT 1 fusion peptide sequence

<400> SEQUENCE: 9

Arg Gln Pro Lys Ile Trp Phe Pro Asn Arg Arg Lys Pro Trp Lys Lys
1               5                   10                  15

Arg Pro Arg Pro Asp Asp Leu Glu Ile
            20                  25

<210> SEQ ID NO 10
<211> LENGTH: 25
<212> TYPE: PRT
<213> ORGANISM: Artificial Sequence
<220> FEATURE:
<223> OTHER INFORMATION: Antp/ACT 3 fusion peptide sequence

<400> SEQUENCE: 10

Arg Gln Pro Lys Ile Trp Phe Pro Asn Arg Arg Lys Pro Trp Lys Lys
1               5                   10                  15

Arg Pro Arg Pro Asp Asp Leu Glu Val
            20                  25

<210> SEQ ID NO 11
<211> LENGTH: 25
<212> TYPE: PRT
<213> ORGANISM: Artificial Sequence
<220> FEATURE:
<223> OTHER INFORMATION: Antp/ACT 4 fusion peptide sequence

<400> SEQUENCE: 11

Arg Gln Pro Lys Ile Trp Phe Pro Asn Arg Arg Lys Pro Trp Lys Lys
1               5                   10                  15

Arg Pro Arg Pro Asp Asp Val Pro Val
            20                  25

<210> SEQ ID NO 12
<211> LENGTH: 25
<212> TYPE: PRT
<213> ORGANISM: Artificial Sequence
<220> FEATURE:
<223> OTHER INFORMATION: Antp/ACT 5 fusion peptide sequence

<400> SEQUENCE: 12

Arg Gln Pro Lys Ile Trp Phe Pro Asn Arg Arg Lys Pro Trp Lys Lys
1               5                   10                  15

Lys Ala Arg Ser Asp Asp Leu Ser Val
            20                  25

<210> SEQ ID NO 13
<211> LENGTH: 74
<212> TYPE: DNA
<213> ORGANISM: Artificial Sequence
<220> FEATURE:
<223> OTHER INFORMATION: Antp/ACT 1 fusion nucleotide sequence

<400> SEQUENCE: 13
cggcagccca agatctggtt ccccaaccgg cggaagccct ggaagaagcg gcccggcccg      60
acgacctgga gatc                                                       74
```

```
<210> SEQ ID NO 14
<211> LENGTH: 11
<212> TYPE: PRT
<213> ORGANISM: Human immunodeficiency virus

<400> SEQUENCE: 14

Gly Arg Lys Lys Arg Arg Gln Arg Pro Pro Gln
1               5                   10

<210> SEQ ID NO 15
<211> LENGTH: 16
<212> TYPE: PRT
<213> ORGANISM: Drosophila melanogaster

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 16
<212> TYPE: PRT
<213> ORGANISM: Drosophila melanogaster

<400> SEQUENCE: 16

Arg Gln Ile Ala Ile Trp Phe Gln Asn Arg Arg Met Lys Trp Ala Ala
1               5                   10                  15

<210> SEQ ID NO 17
<211> LENGTH: 9
<212> TYPE: PRT
<213> ORGANISM: Human immunodeficiency virus

<400> SEQUENCE: 17

Arg Lys Lys Arg Arg Gln Arg Arg Arg
1               5

<210> SEQ ID NO 18
<211> LENGTH: 21
<212> TYPE: PRT
<213> ORGANISM: Artificial Sequence
<220> FEATURE:
<223> OTHER INFORMATION: mutated Buforin II peptide sequence

<400> SEQUENCE: 18

Thr Arg Ser Ser Arg Ala Gly Leu Gln Phe Pro Val Gly Arg Val His
1               5                   10                  15

Arg Leu Leu Arg Lys
            20

<210> SEQ ID NO 19
<211> LENGTH: 26
<212> TYPE: PRT
<213> ORGANISM: Artificial Sequence
<220> FEATURE:
<223> OTHER INFORMATION: mutated Transportan peptide sequence

<400> SEQUENCE: 19

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 20
```

```
<211> LENGTH: 18
<212> TYPE: PRT
<213> ORGANISM: Artificial Sequence
<220> FEATURE:
<223> OTHER INFORMATION: model amphipathic peptide

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 16
<212> TYPE: PRT
<213> ORGANISM: Artificial Sequence
<220> FEATURE:
<223> OTHER INFORMATION: mutated K-FGF peptide sequence

<400> SEQUENCE: 21

Ala Ala Val Ala Leu Leu Pro Ala Val Leu Leu Ala Leu Leu Ala Pro
1               5                   10                  15

<210> SEQ ID NO 22
<211> LENGTH: 10
<212> TYPE: PRT
<213> ORGANISM: Artificial Sequence
<220> FEATURE:
<223> OTHER INFORMATION: mutated Ku70 peptide sequence

<400> SEQUENCE: 22

Val Pro Met Leu Lys Pro Met Leu Lys Glu
1               5                   10

<210> SEQ ID NO 23
<211> LENGTH: 28
<212> TYPE: PRT
<213> ORGANISM: Artificial Sequence
<220> FEATURE:
<223> OTHER INFORMATION: mutated Prion peptide sequence

<400> SEQUENCE: 23

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
                20                  25

<210> SEQ ID NO 24
<211> LENGTH: 18
<212> TYPE: PRT
<213> ORGANISM: Mus musculus

<400> SEQUENCE: 24

Leu Leu Ile Ile Leu Arg Arg Arg Ile Arg Lys Gln Ala His Ala His
1               5                   10                  15

Ser Lys

<210> SEQ ID NO 25
<211> LENGTH: 21
<212> TYPE: PRT
<213> ORGANISM: Artificial Sequence
<220> FEATURE:
<223> OTHER INFORMATION: mutated Pep-1 peptide sequence

<400> SEQUENCE: 25

Lys Glu Thr Trp Trp Glu Thr Trp Trp Thr Glu Trp Ser Gln Pro Lys
```

```
                1               5                  10                 15

Lys Lys Arg Lys Val
                20

<210> SEQ ID NO 26
<211> LENGTH: 18
<212> TYPE: PRT
<213> ORGANISM: Artificial Sequence
<220> FEATURE:
<223> OTHER INFORMATION: mutated SynB1 peptide sequence

<400> SEQUENCE: 26

Arg Gly Gly Arg Leu Ser Tyr Ser Arg Arg Arg Phe Ser Thr Ser Thr
1               5                   10                  15

Gly Arg

<210> SEQ ID NO 27
<211> LENGTH: 15
<212> TYPE: PRT
<213> ORGANISM: Artificial Sequence
<220> FEATURE:
<223> OTHER INFORMATION: mutated Pep-7 peptide sequence

<400> SEQUENCE: 27

Ser Asp Leu Trp Glu Met Met Met Val Ser Leu Ala Cys Gln Tyr
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: mutated HN-1 peptide sequence

<400> SEQUENCE: 28

Thr Ser Pro Leu Asn Ile His Asn Gly Gln Lys Leu
1               5                   10

<210> SEQ ID NO 29
<211> LENGTH: 19
<212> TYPE: PRT
<213> ORGANISM: Gallus gallus

<400> SEQUENCE: 29

Pro Ser Arg Ala Ser Ser Arg Ala Ser Ser Arg Pro Arg Pro Asp Asp
1               5                   10                  15

Leu Glu Ile

<210> SEQ ID NO 30
<211> LENGTH: 20
<212> TYPE: PRT
<213> ORGANISM: Homo sapiens

<400> SEQUENCE: 30

Gly Ser Asn Lys Ser Thr Ala Ser Ser Lys Ser Pro Asp Pro Lys Asn
1               5                   10                  15

Ser Val Trp Ile
                20

<210> SEQ ID NO 31
<211> LENGTH: 20
<212> TYPE: PRT
<213> ORGANISM: Gallus gallus
```

```
<400> SEQUENCE: 31

Gly Ser Asn Lys Ser Ser Ala Ser Ser Lys Ser Gly Asp Gly Lys Asn
1               5                   10                  15

Ser Val Trp Ile
            20

<210> SEQ ID NO 32
<211> LENGTH: 21
<212> TYPE: PRT
<213> ORGANISM: Homo sapiens

<400> SEQUENCE: 32

Gly Arg Ala Ser Lys Ala Ser Arg Ala Ser Ser Gly Arg Ala Arg Pro
1               5                   10                  15

Glu Asp Leu Ala Ile
            20

<210> SEQ ID NO 33
<211> LENGTH: 13
<212> TYPE: PRT
<213> ORGANISM: Homo sapiens

<400> SEQUENCE: 33

Gly Ser Ala Ser Ser Arg Asp Gly Lys Thr Val Trp Ile
1               5                   10

<210> SEQ ID NO 34
<211> LENGTH: 19
<212> TYPE: PRT
<213> ORGANISM: Pan troglodytes

<400> SEQUENCE: 34

Pro Arg Val Ser Val Pro Asn Phe Gly Arg Thr Gln Ser Ser Asp Ser
1               5                   10                  15

Ala Tyr Val

<210> SEQ ID NO 35
<211> LENGTH: 19
<212> TYPE: PRT
<213> ORGANISM: Gallus gallus

<400> SEQUENCE: 35

Pro Arg Met Ser Met Pro Asn Phe Gly Arg Thr Gln Ser Ser Asp Ser
1               5                   10                  15

Ala Tyr Val

<210> SEQ ID NO 36
<211> LENGTH: 21
<212> TYPE: PRT
<213> ORGANISM: Homo sapiens

<400> SEQUENCE: 36

Pro Arg Ala Gly Ser Glu Lys Gly Ser Ala Ser Ser Arg Asp Gly Lys
1               5                   10                  15

Thr Thr Val Trp Ile
            20

<210> SEQ ID NO 37
<211> LENGTH: 23
<212> TYPE: PRT
<213> ORGANISM: Homo sapiens
```

```
<400> SEQUENCE: 37

Gly Tyr His Ser Asp Lys Arg Arg Leu Ser Lys Ala Ser Ser Lys Ala
1               5                   10                  15

Arg Ser Asp Asp Leu Ser Val
            20

<210> SEQ ID NO 38
<211> LENGTH: 19
<212> TYPE: PRT
<213> ORGANISM: Homo sapiens

<400> SEQUENCE: 38

Pro Leu Ser Arg Leu Ser Lys Ala Ser Ser Arg Ala Arg Ser Asp Asp
1               5                   10                  15

Leu Thr Val

<210> SEQ ID NO 39
<211> LENGTH: 22
<212> TYPE: PRT
<213> ORGANISM: Homo sapiens

<400> SEQUENCE: 39

Pro Asn His Val Val Ser Leu Thr Asn Asn Leu Ile Gly Arg Arg Val
1               5                   10                  15

Pro Thr Asp Leu Gln Ile
            20

<210> SEQ ID NO 40
<211> LENGTH: 29
<212> TYPE: PRT
<213> ORGANISM: Rattus norvegicus

<400> SEQUENCE: 40

Pro Ser Cys Val Ser Ser Ala Val Leu Thr Thr Ile Cys Ser Ser
1               5                   10                  15

Asp Gln Val Val Pro Val Gly Leu Ser Ser Phe Tyr Met
            20                  25

<210> SEQ ID NO 41
<211> LENGTH: 21
<212> TYPE: PRT
<213> ORGANISM: Ovis aries

<400> SEQUENCE: 41

Gly Arg Ser Ser Lys Ala Ser Lys Ser Ser Gly Gly Arg Ala Arg Ala
1               5                   10                  15

Ala Asp Leu Ala Ile
            20

<210> SEQ ID NO 42
<211> LENGTH: 17
<212> TYPE: PRT
<213> ORGANISM: Homo sapiens

<400> SEQUENCE: 42

Leu Cys Tyr Leu Leu Ile Arg Tyr Cys Ser Gly Lys Ser Lys Lys Pro
1               5                   10                  15

Val

<210> SEQ ID NO 43
<211> LENGTH: 18
```

<212> TYPE: PRT
<213> ORGANISM: Homo sapiens

<400> SEQUENCE: 43

Gly Gln Lys Pro Pro Ser Arg Pro Ser Ser Ala Ser Lys Lys Gln
1               5                   10                  15

Tyr Val

<210> SEQ ID NO 44
<211> LENGTH: 19
<212> TYPE: PRT
<213> ORGANISM: Artificial Sequence
<220> FEATURE:
<223> OTHER INFORMATION: conservative Cx43 variant

<400> SEQUENCE: 44

Ser Ser Arg Ala Ser Ser Arg Ala Ser Ser Arg Pro Arg Pro Asp Asp
1               5                   10                  15

Leu Glu Val

<210> SEQ ID NO 45
<211> LENGTH: 9
<212> TYPE: PRT
<213> ORGANISM: Artificial Sequence
<220> FEATURE:
<223> OTHER INFORMATION: conservative Cx43 variant

<400> SEQUENCE: 45

Arg Pro Lys Pro Asp Asp Leu Glu Ile
1               5

<210> SEQ ID NO 46
<211> LENGTH: 19
<212> TYPE: PRT
<213> ORGANISM: Artificial Sequence
<220> FEATURE:
<223> OTHER INFORMATION: conservative Cx43 variant

<400> SEQUENCE: 46

Ser Ser Arg Ala Ser Ser Arg Ala Ser Ser Arg Pro Lys Pro Asp Asp
1               5                   10                  15

Leu Glu Ile

<210> SEQ ID NO 47
<211> LENGTH: 9
<212> TYPE: PRT
<213> ORGANISM: Artificial Sequence
<220> FEATURE:
<223> OTHER INFORMATION: conservative Cx43 variant

<400> SEQUENCE: 47

Arg Pro Lys Pro Asp Asp Leu Asp Ile
1               5

<210> SEQ ID NO 48
<211> LENGTH: 19
<212> TYPE: PRT
<213> ORGANISM: Artificial Sequence
<220> FEATURE:
<223> OTHER INFORMATION: conservative Cx43 variant

<400> SEQUENCE: 48

Ser Ser Arg Ala Ser Ser Arg Ala Ser Ser Arg Pro Arg Pro Asp Asp
1               5                   10                  15

-continued

Leu Asp Ile

```
<210> SEQ ID NO 49
<211> LENGTH: 19
<212> TYPE: PRT
<213> ORGANISM: Artificial Sequence
<220> FEATURE:
<223> OTHER INFORMATION: conservative Cx43 variant

<400> SEQUENCE: 49
```

Ser Ser Arg Ala Ser Thr Arg Ala Ser Ser Arg Pro Arg Pro Asp Asp
1               5                   10                  15

Leu Glu Ile

```
<210> SEQ ID NO 50
<211> LENGTH: 9
<212> TYPE: PRT
<213> ORGANISM: Artificial Sequence
<220> FEATURE:
<223> OTHER INFORMATION: conservative Cx43 variant

<400> SEQUENCE: 50
```

Arg Pro Arg Pro Glu Asp Leu Glu Ile
1               5

```
<210> SEQ ID NO 51
<211> LENGTH: 19
<212> TYPE: PRT
<213> ORGANISM: Artificial Sequence
<220> FEATURE:
<223> OTHER INFORMATION: conservative Cx43 variant

<400> SEQUENCE: 51
```

Ser Ser Arg Ala Ser Ser Arg Ala Ser Ser Arg Pro Arg Pro Glu Asp
1               5                   10                  15

Leu Glu Ile

```
<210> SEQ ID NO 52
<211> LENGTH: 9
<212> TYPE: PRT
<213> ORGANISM: Artificial Sequence
<220> FEATURE:
<223> OTHER INFORMATION: conservative Cx45 variant

<400> SEQUENCE: 52
```

Gly Asp Gly Lys Asn Ser Val Trp Val
1               5

```
<210> SEQ ID NO 53
<211> LENGTH: 23
<212> TYPE: PRT
<213> ORGANISM: Artificial Sequence
<220> FEATURE:
<223> OTHER INFORMATION: conservative Cx45 variant

<400> SEQUENCE: 53
```

Ser Lys Ala Gly Ser Asn Lys Ser Thr Ala Ser Ser Lys Ser Gly Asp
1               5                   10                  15

Gly Lys Asn Ser Val Trp Val
            20

```
<210> SEQ ID NO 54
<211> LENGTH: 18
<212> TYPE: PRT
<213> ORGANISM: Artificial Sequence
```

```
<220> FEATURE:
<223> OTHER INFORMATION: conservative Cx37 variant

<400> SEQUENCE: 54

Gly Gln Lys Pro Pro Ser Arg Pro Ser Ser Ser Ala Ser Lys Lys Leu
1               5                   10                  15

Tyr Val

<210> SEQ ID NO 55
<211> LENGTH: 24
<212> TYPE: PRT
<213> ORGANISM: Artificial Sequence
<220> FEATURE:
<223> OTHER INFORMATION: non-active control peptide

<400> SEQUENCE: 55

Arg Gln Pro Lys Ile Trp Phe Pro Asn Arg Arg Lys Pro Trp Lys Ile
1               5                   10                  15

Glu Leu Asp Asp Pro Arg Pro Arg
            20

<210> SEQ ID NO 56
<211> LENGTH: 20
<212> TYPE: PRT
<213> ORGANISM: Artificial Sequence
<220> FEATURE:
<223> OTHER INFORMATION: HIV-Tat/ACT 1 fusion peptide sequence

<400> SEQUENCE: 56

Gly Arg Lys Lys Arg Arg Gln Arg Pro Pro Gln Arg Pro Arg Pro Asp
1               5                   10                  15

Asp Leu Glu Ile
            20

<210> SEQ ID NO 57
<211> LENGTH: 25
<212> TYPE: PRT
<213> ORGANISM: Artificial Sequence
<220> FEATURE:
<223> OTHER INFORMATION: Penetratin/ACT 1 fusion peptide sequence

<400> SEQUENCE: 57

Arg Gln Ile Lys Ile Trp Phe Gln Asn Arg Arg Met Lys Trp Lys Lys
1               5                   10                  15

Arg Pro Arg Pro Asp Asp Leu Glu Ile
            20                  25

<210> SEQ ID NO 58
<211> LENGTH: 25
<212> TYPE: PRT
<213> ORGANISM: Artificial Sequence
<220> FEATURE:
<223> OTHER INFORMATION: Antp-3A/ACT 1 fusion peptide sequence

<400> SEQUENCE: 58

Arg Gln Ile Ala Ile Trp Phe Gln Asn Arg Arg Met Lys Trp Ala Ala
1               5                   10                  15

Arg Pro Arg Pro Asp Asp Leu Glu Ile
            20                  25

<210> SEQ ID NO 59
<211> LENGTH: 18
<212> TYPE: PRT
<213> ORGANISM: Artificial Sequence
```

```
<220> FEATURE:
<223> OTHER INFORMATION: Tat/ACT 1 fusion peptide sequence

<400> SEQUENCE: 59

Arg Lys Lys Arg Arg Gln Arg Arg Arg Pro Arg Pro Asp Asp Leu
1               5                   10                  15

Glu Ile

<210> SEQ ID NO 60
<211> LENGTH: 30
<212> TYPE: PRT
<213> ORGANISM: Artificial Sequence
<220> FEATURE:
<223> OTHER INFORMATION: Buforin II/ACT 1 fusion peptide sequence

<400> SEQUENCE: 60

Thr Arg Ser Ser Arg Ala Gly Leu Gln Phe Pro Val Gly Arg Val His
1               5                   10                  15

Arg Leu Leu Arg Lys Arg Pro Arg Pro Asp Asp Leu Glu Ile
            20                  25                  30

<210> SEQ ID NO 61
<211> LENGTH: 35
<212> TYPE: PRT
<213> ORGANISM: Artificial Sequence
<220> FEATURE:
<223> OTHER INFORMATION: Transportan/ACT 1 fusion peptide sequence

<400> SEQUENCE: 61

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu Arg Pro Arg Pro Asp Asp
            20                  25                  30

Leu Glu Ile
        35

<210> SEQ ID NO 62
<211> LENGTH: 27
<212> TYPE: PRT
<213> ORGANISM: Artificial Sequence
<220> FEATURE:
<223> OTHER INFORMATION: MAP/ACT 1 fusion peptide sequence

<400> SEQUENCE: 62

Lys Leu Ala Leu Lys Leu Ala Leu Lys Ala Leu Lys Ala Ala Leu Lys
1               5                   10                  15

Leu Ala Arg Pro Arg Pro Asp Asp Leu Glu Ile
            20                  25

<210> SEQ ID NO 63
<211> LENGTH: 25
<212> TYPE: PRT
<213> ORGANISM: Artificial Sequence
<220> FEATURE:
<223> OTHER INFORMATION: K-FGF/ACT 1 fusion peptide sequence

<400> SEQUENCE: 63

Ala Ala Val Ala Leu Leu Pro Ala Val Leu Leu Ala Leu Leu Ala Pro
1               5                   10                  15

Arg Pro Arg Pro Asp Asp Leu Glu Ile
            20                  25

<210> SEQ ID NO 64
```

```
<211> LENGTH: 19
<212> TYPE: PRT
<213> ORGANISM: Artificial Sequence
<220> FEATURE:
<223> OTHER INFORMATION: Ku70/ACT 1 fusion peptide sequence

<400> SEQUENCE: 64

Val Pro Met Leu Lys Pro Met Leu Lys Glu Arg Pro Arg Pro Asp Asp
1               5                   10                  15

Leu Glu Ile

<210> SEQ ID NO 65
<211> LENGTH: 37
<212> TYPE: PRT
<213> ORGANISM: Artificial Sequence
<220> FEATURE:
<223> OTHER INFORMATION: Prion/ACT 1 fusion peptide sequence

<400> SEQUENCE: 65

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Arg Pro Arg Pro
            20                  25                  30

Asp Asp Leu Glu Ile
        35

<210> SEQ ID NO 66
<211> LENGTH: 27
<212> TYPE: PRT
<213> ORGANISM: Artificial Sequence
<220> FEATURE:
<223> OTHER INFORMATION: pVEC/ACT 1 fusion peptide sequence

<400> SEQUENCE: 66

Leu Leu Ile Ile Leu Arg Arg Arg Ile Arg Lys Gln Ala His Ala His
1               5                   10                  15

Ser Lys Arg Pro Arg Pro Asp Asp Leu Glu Ile
            20                  25

<210> SEQ ID NO 67
<211> LENGTH: 30
<212> TYPE: PRT
<213> ORGANISM: Artificial Sequence
<220> FEATURE:
<223> OTHER INFORMATION: Pep-1/ACT 1 fusion peptide sequence

<400> SEQUENCE: 67

Lys Glu Thr Trp Trp Glu Thr Trp Trp Thr Glu Trp Ser Gln Pro Lys
1               5                   10                  15

Lys Lys Arg Lys Val Arg Pro Arg Pro Asp Asp Leu Glu Ile
            20                  25                  30

<210> SEQ ID NO 68
<211> LENGTH: 27
<212> TYPE: PRT
<213> ORGANISM: Artificial Sequence
<220> FEATURE:
<223> OTHER INFORMATION: SynB1/ACT 1 fusion peptide sequence

<400> SEQUENCE: 68

Arg Gly Gly Arg Leu Ser Tyr Ser Arg Arg Phe Ser Thr Ser Thr
1               5                   10                  15

Gly Arg Arg Pro Arg Pro Asp Asp Leu Glu Ile
            20                  25
```

<210> SEQ ID NO 69
<211> LENGTH: 24
<212> TYPE: PRT
<213> ORGANISM: Artificial Sequence
<220> FEATURE:
<223> OTHER INFORMATION: Pep-7/ACT 1 fusion peptide sequence

<400> SEQUENCE: 69

Ser Asp Leu Trp Glu Met Met Met Val Ser Leu Ala Cys Gln Tyr Arg
1               5                   10                  15

Pro Arg Pro Asp Asp Leu Glu Ile
            20

<210> SEQ ID NO 70
<211> LENGTH: 21
<212> TYPE: PRT
<213> ORGANISM: Artificial Sequence
<220> FEATURE:
<223> OTHER INFORMATION: HN-1/ACT 1 fusion peptide sequence

<400> SEQUENCE: 70

Thr Ser Pro Leu Asn Ile His Asn Gly Gln Lys Leu Arg Pro Arg Pro
1               5                   10                  15

Asp Asp Leu Glu Ile
            20

<210> SEQ ID NO 71
<211> LENGTH: 122
<212> TYPE: PRT
<213> ORGANISM: Homo sapiens

<400> SEQUENCE: 71

Lys Gly Lys Ser Asp Pro Tyr His Ala Thr Ser Gly Ala Leu Ser Pro
1               5                   10                  15

Ala Lys Asp Cys Gly Ser Gln Lys Tyr Ala Tyr Phe Asn Gly Cys Ser
                20                  25                  30

Ser Pro Thr Ala Pro Leu Ser Pro Met Ser Pro Pro Gly Tyr Lys Leu
            35                  40                  45

Val Thr Gly Asp Arg Asn Asn Ser Ser Cys Arg Asn Tyr Asn Lys Gln
        50                  55                  60

Ala Ser Glu Gln Asn Trp Ala Asn Tyr Ser Ala Glu Gln Asn Arg Met
65                  70                  75                  80

Gly Gln Ala Gly Ser Thr Ile Ser Asn Ser His Ala Gln Pro Phe Asp
                85                  90                  95

Phe Pro Asp Asp Asn Gln Asn Ser Lys Lys Leu Ala Ala Gly His Glu
            100                 105                 110

Leu Gln Pro Leu Ala Ile Val Asp Gln Arg
        115                 120

<210> SEQ ID NO 72
<211> LENGTH: 120
<212> TYPE: PRT
<213> ORGANISM: Gallus gallus

<400> SEQUENCE: 72

Lys Thr Asp Pro Tyr Ser His Ser Gly Thr Met Ser Pro Ser Lys Asp
1               5                   10                  15

Cys Gly Ser Pro Lys Tyr Ala Tyr Asn Gly Cys Ser Ser Pro Thr
                20                  25                  30

Ala Pro Leu Ser Pro Met Ser Pro Gly Tyr Lys Leu Val Thr Gly
         35                  40                  45

Asp Arg Asn Asn Ser Ser Cys Arg Asn Tyr Asn Lys Gln Ala Ser Glu
 50                      55                  60

Gln Asn Trp Ala Asn Tyr Ser Ala Glu Gln Asn Arg Met Gly Gln Ala
 65                  70                  75                  80

Gly Ser Thr Ile Ser Asn Ser His Ala Gln Pro Phe Asp Phe Ala Asp
                 85                  90                  95

Glu His Gln Asn Thr Lys Lys Leu Ala Ser Gly His Glu Leu Gln Pro
                100                 105                 110

Leu Thr Ile Val Asp Gln Arg Pro
            115                 120

<210> SEQ ID NO 73
<211> LENGTH: 120
<212> TYPE: PRT
<213> ORGANISM: Homo sapiens

<400> SEQUENCE: 73

Leu Gly Phe Gly Thr Ile Arg Asp Ser Leu Asn Ser Lys Arg Arg Glu
 1               5                  10                  15

Leu Glu Asp Pro Gly Ala Tyr Asn Tyr Pro Phe Thr Trp Asn Thr Pro
                 20                  25                  30

Ser Ala Pro Pro Gly Tyr Asn Ile Ala Val Lys Pro Asp Gln Ile Gln
             35                  40                  45

Tyr Thr Glu Leu Ser Asn Ala Lys Ile Ala Tyr Lys Gln Asn Lys Ala
 50                  55                  60

Asn Thr Ala Gln Glu Gln Gln Tyr Gly Ser His Glu Glu Asn Leu Pro
 65                  70                  75                  80

Ala Asp Leu Glu Ala Leu Gln Arg Glu Ile Arg Met Ala Gln Glu Arg
                 85                  90                  95

Leu Asp Leu Ala Val Gln Ala Tyr Ser His Gln Asn Asn Pro His Gly
                100                 105                 110

Pro Arg Glu Lys Lys Ala Lys Val
            115                 120

<210> SEQ ID NO 74
<211> LENGTH: 120
<212> TYPE: PRT
<213> ORGANISM: Gallus gallus

<400> SEQUENCE: 74

Gly Phe Gly Thr Ile Arg Asp Thr Leu Asn Asn Lys Arg Lys Glu Leu
 1               5                  10                  15

Glu Asp Ser Gly Thr Tyr Asn Tyr Pro Phe Thr Trp Asn Thr Pro Ser
                 20                  25                  30

Ala Pro Pro Gly Tyr Asn Ile Ala Val Lys Pro Asp Gln Met Gln Tyr
             35                  40                  45

Thr Glu Leu Ser Asn Ala Lys Met Ala Tyr Lys Gln Asn Lys Ala Asn
 50                  55                  60

Ile Ala Gln Glu Gln Gln Tyr Gly Ser Asn Glu Glu Asn Ile Pro Ala
 65                  70                  75                  80

Asp Leu Glu Asn Leu Gln Arg Glu Ile Lys Val Ala Gln Glu Arg Leu
                 85                  90                  95

Asp Met Ala Ile Gln Ala Tyr Asn Asn Gln Asn Asn Pro Gly Ser Ser
                100                 105                 110

```
Ser Arg Glu Lys Lys Ser Lys Ala
        115                 120
```

<210> SEQ ID NO 75
<211> LENGTH: 120
<212> TYPE: PRT
<213> ORGANISM: Homo sapiens

<400> SEQUENCE: 75

```
Pro Tyr Leu Val Asp Cys Phe Val Ser Arg Pro Thr Glu Lys Thr Ile
1               5                   10                  15

Phe Ile Ile Phe Met Leu Val Val Gly Leu Ile Ser Leu Val Leu Asn
            20                  25                  30

Leu Leu Glu Leu Val His Leu Leu Cys Arg Cys Leu Ser Arg Gly Met
        35                  40                  45

Arg Ala Arg Gln Gly Gln Asp Ala Pro Pro Thr Gln Gly Thr Ser Ser
    50                  55                  60

Asp Pro Tyr Thr Asp Gln Val Phe Phe Tyr Leu Pro Val Gly Gln Gly
65                  70                  75                  80

Pro Ser Ser Pro Pro Cys Pro Thr Tyr Asn Gly Leu Ser Ser Ser Glu
                85                  90                  95

Gln Asn Trp Ala Asn Leu Thr Thr Glu Glu Arg Leu Ala Ser Ser Arg
            100                 105                 110

Pro Pro Leu Phe Leu Asp Pro Pro
        115                 120
```

<210> SEQ ID NO 76
<211> LENGTH: 120
<212> TYPE: PRT
<213> ORGANISM: Rattus norvegicus

<400> SEQUENCE: 76

```
Cys Gly Ser Lys Glu His Gly Asn Arg Lys Met Arg Gly Arg Leu Leu
1               5                   10                  15

Leu Thr Tyr Met Ala Ser Ile Phe Phe Lys Ser Val Phe Glu Val Ala
            20                  25                  30

Phe Leu Leu Ile Gln Trp Tyr Leu Tyr Gly Phe Thr Leu Ser Ala Val
        35                  40                  45

Tyr Ile Cys Glu Gln Ser Pro Cys Pro His Arg Val Asp Cys Phe Leu
    50                  55                  60

Ser Arg Pro Thr Glu Lys Thr Ile Phe Ile Leu Phe Met Leu Val Val
65                  70                  75                  80

Ser Met Val Ser Phe Val Leu Asn Val Ile Glu Leu Phe Tyr Val Leu
                85                  90                  95

Phe Lys Ala Ile Lys Asn His Leu Gly Asn Gly Lys Glu Glu Val Tyr
            100                 105                 110

Cys Asn Pro Val Glu Leu Gln Lys
        115                 120
```

<210> SEQ ID NO 77
<211> LENGTH: 239
<212> TYPE: PRT
<213> ORGANISM: Artificial Sequence
<220> FEATURE:
<223> OTHER INFORMATION: enhanced green fluorescent protein

<400> SEQUENCE: 77

```
Met Val Ser Lys Gly Glu Glu Leu Phe Thr Gly Val Val Pro Ile Leu
1               5                   10                  15
```

Val Glu Leu Asp Gly Asp Val Asn Gly His Lys Phe Ser Val Ser Gly
        20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 78
<211> LENGTH: 60
<212> TYPE: DNA
<213> ORGANISM: Homo sapiens

<400> SEQUENCE: 78
ccctcctccc gggcctcctc ccgggcctcc tcccggcccc ggcccgacga cctggagatc      60

<210> SEQ ID NO 79
<211> LENGTH: 27
<212> TYPE: DNA
<213> ORGANISM: Homo sapiens

<400> SEQUENCE: 79
cggccccggc ccgacgacct ggagatc                                          27

<210> SEQ ID NO 80
<211> LENGTH: 27
<212> TYPE: DNA
<213> ORGANISM: Artificial Sequence
<220> FEATURE:
<223> OTHER INFORMATION: mutated ACT 3 nucleotide sequence

<400> SEQUENCE: 80
cggccccggc ccgacgacct ggaggtg                                          27

<210> SEQ ID NO 81
<211> LENGTH: 27
<212> TYPE: DNA

<213> ORGANISM: Artificial Sequence
<220> FEATURE:
<223> OTHER INFORMATION: mutated ACT 4 nucleotide sequence

<400> SEQUENCE: 81
cggccccggc ccgacgacgt gcccgtg                                    27

<210> SEQ ID NO 82
<211> LENGTH: 27
<212> TYPE: DNA
<213> ORGANISM: Artificial Sequence
<220> FEATURE:
<223> OTHER INFORMATION: mutated ACT 5 nucleotide sequence

<400> SEQUENCE: 82
aaggcccggt ccgacgacct gtccgtg                                    27

<210> SEQ ID NO 83
<211> LENGTH: 48
<212> TYPE: DNA
<213> ORGANISM: Drosophila melanogaster

<400> SEQUENCE: 83
cggcagccca agatctggtt ccccaaccgg cggaagccct ggaagaag              48

<210> SEQ ID NO 84
<211> LENGTH: 108
<212> TYPE: DNA
<213> ORGANISM: Artificial Sequence
<220> FEATURE:
<223> OTHER INFORMATION: Antp/ACT 2 fusion nucleotide sequence

<400> SEQUENCE: 84
cggcagccca agatctggtt ccccaaccgg cggaagccct ggaagaagcc ctcctcccgg    60
gcctcctccc gggcctcctc ccggccccgg cccgacgacc tggagatc             108

<210> SEQ ID NO 85
<211> LENGTH: 75
<212> TYPE: DNA
<213> ORGANISM: Artificial Sequence
<220> FEATURE:
<223> OTHER INFORMATION: Antp/ACT 1 fusion nucleotide sequence

<400> SEQUENCE: 85
cggcagccca agatctggtt ccccaaccgg cggaagccct ggaagaagcg ccccggccc    60 gacgacctgg agatc                                                 75

<210> SEQ ID NO 86
<211> LENGTH: 75
<212> TYPE: DNA
<213> ORGANISM: Artificial Sequence
<220> FEATURE:
<223> OTHER INFORMATION: Antp/ACT 3 fusion nucleotide sequence

<400> SEQUENCE: 86
cggcagccca agatctggtt ccccaaccgg cggaagccct ggaagaagcg ccccggccc    60 gacgacctgg aggtg                                                 75

<210> SEQ ID NO 87
<211> LENGTH: 75
<212> TYPE: DNA
<213> ORGANISM: Artificial Sequence
<220> FEATURE:
<223> OTHER INFORMATION: Antp/ACT 4 fusion nucleotide sequence

<400> SEQUENCE: 87
cggcagccca agatctggtt ccccaaccgg cggaagccct ggaagaagcg gccccggccc    60
gacgacgtgc ccgtg                                                    75

<210> SEQ ID NO 88
<211> LENGTH: 75
<212> TYPE: DNA
<213> ORGANISM: Artificial Sequence
<220> FEATURE:
<223> OTHER INFORMATION: Antp/ACT 5 fusion nucleotide sequence

<400> SEQUENCE: 88
cggcagccca agatctggtt ccccaaccgg cggaagccct ggaagaagaa ggcccggtcc    60
gacgacctgt ccgtg                                                    75

<210> SEQ ID NO 89
<211> LENGTH: 20
<212> TYPE: PRT
<213> ORGANISM: Danio rerio

<400> SEQUENCE: 89

Pro Cys Ser Arg Ala Ser Ser Arg Met Ser Ser Arg Ala Arg Pro Asp
1               5                   10                  15

Asp Leu Asp Val
            20

<210> SEQ ID NO 90
<211> LENGTH: 19
<212> TYPE: PRT
<213> ORGANISM: Gallus gallus

<400> SEQUENCE: 90

Pro Arg Val Ser Val Pro Asn Phe Gly Arg Thr Gln Ser Ser Asp Ser
1               5                   10                  15

Ala Tyr Val

<210> SEQ ID NO 91
<211> LENGTH: 19
<212> TYPE: PRT
<213> ORGANISM: Danio rerio

<400> SEQUENCE: 91

Pro Arg Met Ser Met Pro Asn Phe Gly Arg Thr Gln Ser Ser Asp Ser
1               5                   10                  15

Ala Tyr Val

<210> SEQ ID NO 92
<211> LENGTH: 32
<212> TYPE: PRT
<213> ORGANISM: Artificial Sequence
<220> FEATURE:
<223> OTHER INFORMATION: Cx43 isoleucine deletion

<400> SEQUENCE: 92

Arg Gln Pro Lys Ile Trp Phe Pro Asn Arg Arg Lys Pro Trp Lys Lys
1               5                   10                  15

Arg Ala Ser Ser Arg Ala Ser Ser Arg Pro Arg Pro Asp Asp Leu Glu
            20                  25                  30

FORMULATIONS AND METHODS OF USE FOR ALPHA CONNEXIN C-TERMINAL (ACT) PEPTIDES

CROSS REFERENCE TO RELATED APPLICATIONS

This application is a continuation of U.S. patent application Ser. No. 14/848,916, filed Sep. 9, 2015, now U.S. Pat. No. 10,632,173, which is a continuation of U.S. patent application Ser. No. 14/341,406, filed Jul. 25, 2014, now U.S. Pat. No. 9,161,984, which is a continuation of U.S. patent application Ser. No. 13/815,723, filed Mar. 15, 2013, now U.S. Pat. No. 8,846,605, which is a continuation-in-part of PCT Application No. PCT/US2013/028727, filed Mar. 1, 2013, which claims priority to U.S. Provisional Patent Application No. 61/605,528, filed Mar. 1, 2012, all of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: FIRS_006_01US_SeqList_ST25.txt, date recorded: Mar. 15, 2013, file size 32 kilobytes).

TECHNICAL FIELD

The present invention relates to compositions for wound treatment comprising alpha connexin polypeptides and stabilizing agents. Topical formulations containing alpha connexin polypeptides and hydroxyethylcellulose are particularly stable. These compositions may be used to treat a variety of wounds including acute surgical wounds and chronic ulcers. Methods for treatment of chronic wounds are also provided.

BACKGROUND

While human tissues damaged by mechanical wounding, disease processes and other causes are capable of healing, complex tissue structure and function is rarely, if ever wholly restored. Instead, recovery of nearly all tissues from injury in humans and other higher vertebrates is dominated by the formation of scar tissue. The most familiar example of this is the discolored and fibrotic scars that linger following the healing of a skin cut or graze. Less well appreciated is that formation of glial scar tissue following injury to the brain or spinal chord is one of the main obstacles to restoration of neural function following damage to the central nervous system (Silver and Miller JH, 2004). There is currently no means of treating or preventing such scarring and promoting the regeneration of complex tissue structure and function following injury.

Once such treatments are discovered, there is also a need to provide formulations that stabilize the active pharmaceutical ingredients (API) which they contain. While there are a myriad of potential stabilizing agents, not all of them work equally well in stabilizing specific APIs.

Venous ulcers are chronic wounds associated with long-standing venous hypertension of the lower extremity. The number of individuals affected by these ulcers in the United States is over 600,000. These indolent wounds are a major cause of morbidity and are a major financial burden. Diabetes affects an estimated 25.8 million people (8% of the US population) according to the Centers for Disease Control and Prevention. People with diabetes have 12-25% chance of developing foot ulcer in their lifetime. Diabetic Foot Ulcers (DFUs) refer to wounds below the ankle of a diabetic subject which develops due to neuropathy (sensory, motor, or autonomic deficits), ischemia or both. Foot ulcers are a substantial cause for morbidity and can severely impair quality of life, engender high treatment costs, and serve as the most important risk factor for lower-extremity amputation.

No single available product or procedure is adequate for the treatment of all subjects with chronic ulcers. Treatment selection is determined by patient tolerance, patient medical status, cost, availability, and physician preference. Compression wraps are the Standard of Care (SoC) and are needed to assist venous return and to address the underlying pathophysiology of venous disease and venous ulceration. Compression bandages and stockings heal more ulcers compared with no compression, but it has not been ascertained if intermittent pneumatic compression is beneficial compared with compression bandages or stockings. Occlusive (hydrocolloid) dressings are no more effective than simple low-adherent dressings in people treated with compression.

Despite various advances in wound treatment, the need exists for additional effective VLU and DFU treatments that combine advanced wound care therapeutics with SoC compression therapy for faster healing of ulcers. Rapid healing would result in fewer hospitalizations, decreased infection, less use of antibiotics, improved mobility, less pain, and fewer surgical procedures for subjects with VLUs or DFUs.

SUMMARY OF THE INVENTION

The present invention is directed in part to a topical gel drug product preparation containing a composition comprising an isolated alpha connexin polypeptide. The topical formulation may further comprise hydroxyethylcellulose gel, which stabilizes the alpha connexin polypeptide during storage. In certain embodiments the alpha connexin polypeptide comprises a carboxy terminal amino acid sequence of an alpha connexin (hereinafter "ACT"). The alpha connexin polypeptides of the present invention may comprise or consist of the carboxy-terminal most 4 to 30 contiguous amino acids of an alpha connexin protein or conservative variant thereof, wherein said at least one alpha connexin polypeptide is linked at its amino terminus to a cellular internalization transporter.

It is an object of the present invention to prepare a formulation of a stable, elegant, and pourable topical gel carrier that contains ACT for aesthetic as well as therapeutic applications including the prevention of scaring and accelerated healing of wounds of a subject. The drug product may be administered to treat acute surgical wounds to reduce scarring or be applied chronically to difficult-to-heal wounds including, but not limited to, venous leg ulcers, diabetic foot ulcers, pressure ulcers, and the like. The drug product possesses physicochemical, biochemical, and rheological properties that enable its ability to provide a therapeutic and effective amount of ACT peptide when applied to all type of wounds.

In one aspect of the invention, one or more stabilizer is selected among many, and prepared with ACT peptide to stabilize the isolated polypeptide. Preferably the stabilizers are non-irritating, non-staining, and non-immunogenic. The stabilizers enable the long term (i.e., for 3 months, for 6 months, for 9 months, for 12 months, for 18 months, or for 24 months) storage of the drug product under a variety of temperature conditions (i.e., at about 5° C., at about 10° C., at about 15° C., at about 20° C., at about 25° C., at about 30° C., at about 35° C., or at about 40° C.) and under a range of relative humidities (i.e., at 0% relative humidity, at 10% relative humidity, at 20% relative humidity, at 30% relative humidity, at 40% relative humidity, at 50% relative humidity, at 60% relative humidity, at 70% relative humidity, at 80% relative humidity, at 90% relative humidity, or at 100% relative humidity).

In another aspect of the invention, one or more excipients are selected from the group consisting of water-soluble porogens, polymers, ionic compounds, non-ionic compounds, and solvents. In a further embodiment, excipients act as one or more of carriers, stabilizers, and gelling agents. In one embodiment, at least one excipient is prepared with ACT. Preferably the excipients are non-irritating, non-staining, and non-immunogenic. In one embodiment the formulation comprises at least one polymer. In a further embodiment, the formulation comprises a derivative of cellulose. In a yet further embodiment, the derivative of cellulose is hydroxyethylcellulose.

In yet another aspect of the invention, an optimal pH range for the topical gel is about pH 5 to about pH 7, and is maintained by the addition of one or more buffering agents. Preferably the buffering agents are non-irritating, non-staining, and non-immunogenic.

In yet another aspect of the invention, at least one excipient is a gelling agent. In one embodiment, a gelling agent is a carrier of ACT. In some embodiments, the gelling agent also acts as a stabilizer. In some embodiments, the gelling agent may be combined with at least one of the following: one or more buffering agent, and one or more additional excipient. In one embodiment, the gelling agent is hydroxyethylcellulose.

In some embodiments, the present invention includes a method of wound treatment comprising administering to a subject in need thereof a topical formulation comprising at least one alpha connexin polypeptide and hydroxyethylcellulose gel. In an exemplary embodiment, the steps are disclosed for manufacturing of the drug product.

The present invention also includes methods of treating wounds and ulcers in a patient in need thereof, particularly wounds and ulcers that are chronic in nature. The present inventors have found that the peptides and formulations of the present invention provide faster healing of ulcers when combined with compression therapy than is achieved by compression therapy alone. Accordingly, the present invention includes methods of treating a chronic wound in a subject, comprising administering to the subject a topical formulation comprising at least one alpha connexin polypeptide in addition to standard of care compression therapy, wherein the chronic wound is healed at a faster rate and/or increased frequency than achieved with standard of care compression therapy alone.

In one aspect a method of treating a chronic wound in a subject comprising administering to the subject a topical formulation comprising at least one alpha connexin polypeptide is provided. In a further embodiment, the formulation is administered daily or weekly or a combination thereof. In another embodiment, the formulation is administered according to any dosing regiment that is effective in the treatment of the chronic wound. In a further embodiment, the formulation is administered in a dosing regimen at day 0, day 3, week 1, week 2, week 3, week 4, week 5, week 6, week 7, week 8, week 9, week 10, week 11, and week 12.

In one embodiment a method of treating a chronic wound in a subject comprising administering to the subject a topical formulation comprising at least one alpha connexin poly-peptide and hydroxyethylcellulose is provided. In a further embodiment, the hydroxyethylcellulose is present at a concentration of about 1.25% (w/w). In one embodiment, the at least one isolated polypeptide comprises the carboxy terminal-most 4 to 30 contiguous amino acids of an alpha Connexin, or a conservative variant thereof. In another embodiment, the alpha connexin polypeptide is connexin 37, connexin 40, connexin 43, or connexin 45. In one embodiment, the alpha connexin is linked at its amino terminus to a cellular internalization transporter such as, for example an Antennapedia sequence, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (BisGuanidinium-Tren-Cholesterol). In one embodiment, the cellular internalization transporter is an antennapedia sequence. In a further embodiment, the formulation comprises a polypeptide comprising the amino acid sequence of SEQ ID NO: 9.

In one embodiment, the formulation for use in treatment of a chronic wound comprises at least one alpha connexin polypeptide and hydroxyethylcellulose gel. In a further embodiment, the hydroxycellulose gel is present at a concentration of about 2%, about 1.75%, about 1.5%, about 1.25%, about 1.0%, or about 0.75%. In one embodiment, the hydroxycellulose gel is present at a concentration of about 1.25% (w/w).

In one aspect, the chronic wound is an ulcer. In a further embodiment, the chronic wound is a lower extremity ulcer. In another embodiment, the chronic wound is selected from the group consisting of venous leg ulcers, diabetic foot ulcers, and pressure ulcers. In one embodiment, a method for treating a chronic wound in a subject is provided, wherein the method comprises administering to the subject a topical formulation of at least one alpha connexin polypeptide, wherein the formulation is administered in a dosing regimen at day 0, day 3, week 1, week 2, week 3, week 4, week 5, week 6, week 7, week 8, week 9, week 10, week 11, and week 12, wherein the symptoms of the chronic wound are reduced. In a further embodiment, the formulation does not induce excessive levels of side effects. In another embodiment, the chronic wound is improved in the absence of clinically significant abnormalities. In another embodiment, the method reduces the time to 100% wound closure, as compared to the time to 100% wound closure when the standard of care treatment is used. In other embodiments, the method reduces the time to 100% wound closure when administered in conjunction with standard of care, as compared to treatment with either standard of care alone.

Standard of care treatments are known to those of skill in the art and include, for example, cleaning the wound, applying dressing to the wound, and applying a pressure bandage to the wound. In one embodiment, the subject treated with the methods and formulations provided herein has a higher percent wound closure as compared to a subject receiving standard of care therapy, at 12 weeks, 11 weeks, 10 weeks, 9 weeks, 8 weeks, 7 weeks, 6 weeks, 5 weeks, 4 weeks, 3 weeks, or 2 weeks. In one embodiment, the percent wound closure at 12 weeks is higher in subjects treated with the methods and formulations disclosed herein, as compared to the percent wound closure at 12 weeks in subjects receiving standard of care treatment. In one embodiment, the method reduces the time to 50% wound closure, as compared to the time to 50% wound closure when the standard of care treatment is used. In another embodiment, the percent wound closure at 4 weeks is higher in subjects treated with the methods and formulations disclosed herein, as compared to the percent wound closure at 4 weeks in subjects treated with standard of care treatment.

In another embodiment, the method results in a reduction in pain levels in the subject. In a further embodiment, the pain level is determined through patient self-assessment. In one embodiment, the method increases the average percent of wound closure at 12 weeks, 11 weeks, 10 weeks, 9 weeks, 8 weeks, 7 weeks, 6 weeks, 5 weeks, 4 weeks, 3 weeks, or 2 weeks as compared to standard of care treatment. In one embodiment, the method increases the average percent of wound closure at 12 weeks. In one embodiment, the method decreases the wound area as compared to the wound area in subjects that are treated with standard of care therapy. In one embodiment, the method does not induce the production of anti-alpha connexin polypeptide antibodies in the subject.

In another embodiment, the method increases the incidence or frequency of 100% complete wound closure compared to standard of care treatments for wound healing. In another embodiment, the method is used to treat an ulcer lacking sufficient wound size reduction within one, four, 12, 24, 36, or more weeks of standard of care. In one embodiment, the method is used to treat an ulcer with less than 50% wound closure within one four, 12, 24, 36, or more weeks of standard of care. In one embodiment, the method is used to treat an ulcer lacking sufficient wound size reduction within one, four, 12, 24, 36, or more weeks of standard of care. In one embodiment, the method is used to treat an ulcer lacking sufficient wound size reduction within one, four, 12, 24, 36, or more weeks of standard of care. In one embodiment, the method is used to treat a patient with an ulcer possessing wound area and duration characteristics of a chronic wound. In one embodiment, the method is used to treat a patient with an ulcer possessing a wound with a non-healing wound trajectory. In one embodiment, the method is used to treat an ulcer possessing wound area and time duration characteristics of a chronic wound.

DESCRIPTION OF DRAWINGS

For a fuller understanding of the nature and advantages of the present invention, reference should be had to the following detailed description taken in connection with the accompanying drawings, in which:

FIG. 2 shows the subject self assessment of pain in the intent-to-treat population in the Diabetic Foot Ulcer (DFU) study.

FIG. 3 shows the subject self assessment of pain in the per-protocol (PP) population in the DFU study.

FIG. 4 shows the time to 100% wound closure in the intent-to-treat (ITT) population in the DFU study.

FIG. 5 shows the time to 100% wound closure in the PP population in the DFU study.

FIG. 6 shows the time to 50% wound closure in the ITT population in the DFU study.

FIG. 7 shows the time to 50% wound closure in the PP population in the DFU study.

FIG. 8 shows the average wound closure at each visit in the ITT population in the DFU study.

FIG. 9 shows the average wound closure at each visit in the PP population in the DFU study.

FIG. 10 shows the Longitudinal Response Profile of the Mean Percent Reduction of Wound Area ($mm^2$) from Baseline to Week 12 by Treatment Group—ITT Population (N=92)

FIG. 11 Longitudinal Response Profile of the Mean Percentage Reduction of Wound Area from Baseline to Week 12 by Treatment Group—mITT Population (N=77)

FIG. 12 shows the Longitudinal Response Profile of the Mean Percentage Reduction of Wound Area ($mm^2$) from Baseline to Week 12 by Treatment Group—PP Population (N=68)

FIG. 13 shows the Kaplan-Meier Plot of Time to First 100% Wound Closure ITT Population (N=92)

FIG. 14 shows the Kaplan-Meier Plot of Time to First 100% Wound Closure ITT Population (N=92)

FIG. 15 shows Kaplan-Meier Plot of Time to First 100% Wound Closure PP Population (N=68)

FIG. 16 shows the Kaplan-Meier Plot of Time to First 50% Wound Closure ITT Population (N=92)

FIG. 17 shows the Kaplan-Meier Plot of Time to 50% Wound Closure—mITT Population (N=77)

FIG. 18 shows the Kaplan-Meier Plot of Time to First 50% Wound Closure PP Population (N=68)

DETAILED DESCRIPTION

Figure 1:
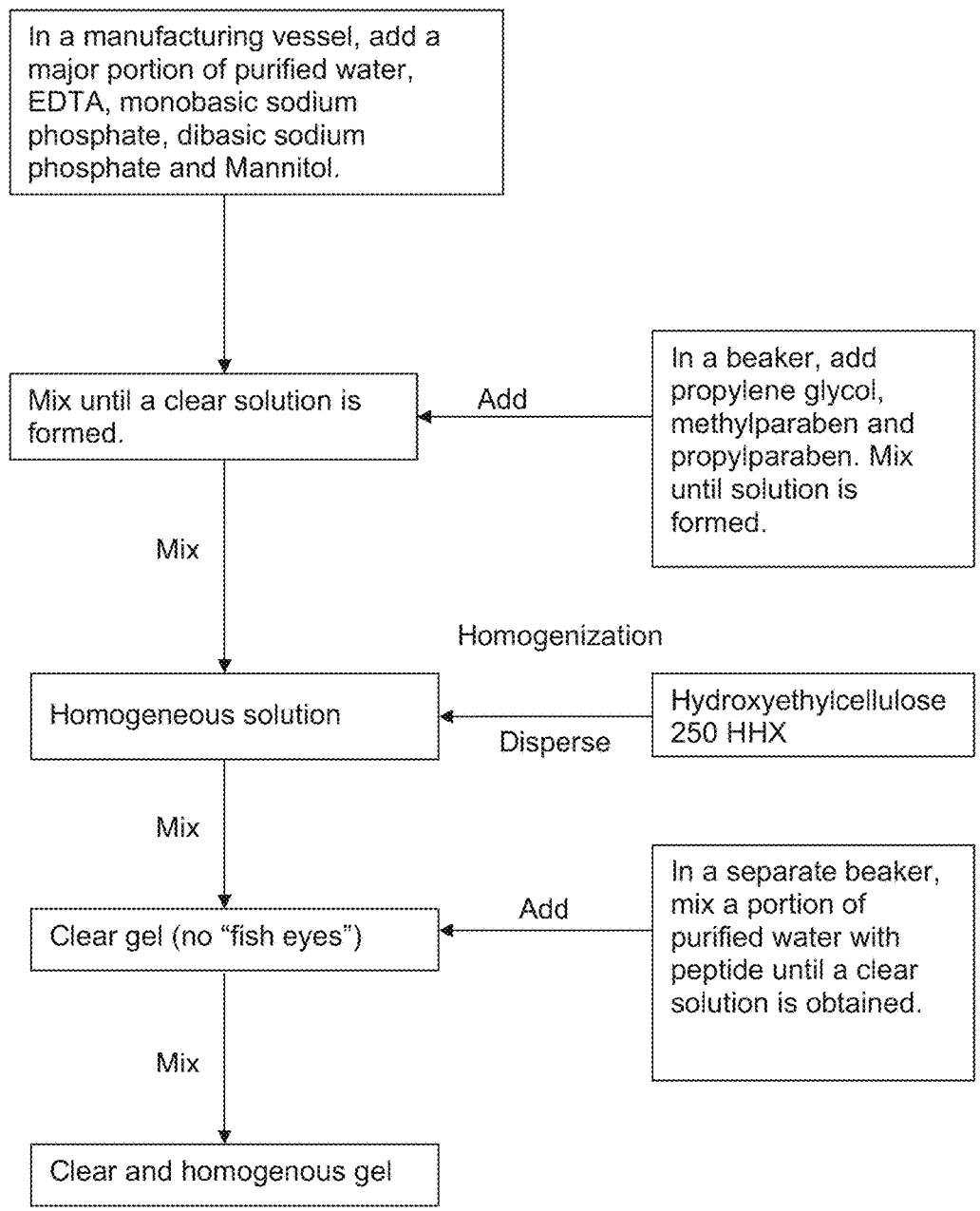
FIG. 1 illustrates the manufacturing process flow chart.

Before the present compositions and methods are described, it is to be understood that this invention is not limited to the particular processes, compositions, or methodologies described, as these may vary. The terminology used in the description is for the purpose of describing the particular versions or embodiments only, and it is not intended to limit the scope of the present invention which will be limited only by the appended claims. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to an "element" is a reference to one or more elements and equivalents thereof known to those skilled in the art, and so forth.

The term "topical" refers to administration of inventive drug product at, or immediately beneath, the point of application. As used herein "topical application" refers to application onto one or more surfaces(s) including keratinous tissue, i.e., "topically applying." Topical application or "topically applying" may involve direct application to the area of the desired substrate. The topical preparation and/or composition may be applied by pouring, dropping, or spraying, if a liquid; rubbing on, if an ointment, lotion, cream, gel, or the like; dusting, if a powder; spraying, if a liquid or aerosol composition; or by any other appropriate means.

As used herein, the phrase "gelling agents" refers to agents that make a topical preparation denser or more viscous in consistency. Gelling agents may be water-based or oil-based. Gelling agents may also be referred to as "thickening agents." "Excipients," as used herein, are inactive ingredients that serve as carriers of the active pharmaceutical ingredient (API). Excipients may also serve as gelling or thickening agents, or stabilizers.

A "subject" or a "mammal" includes a human or a non-human mammal. Non-human mammals include, but not limited to, livestock and pets, such as ovine, bovine, porcine, canine, feline and murine mammals. In one embodiment, the subject or mammal is human.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with the drug product, can include, but is not limited to, providing the drug product and the ACT peptide into or onto the target tissue. "Administering" a composition may be accomplished by injection, topical administration, or by any method in combination with other known techniques.

Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to the treatment of scarring and delayed wound healing.

As used herein, the phrase "effective amount" or "therapeutically effective amount" refers to a nontoxic but sufficient amount of the ACT polypeptides used in the practice of the invention that is effective to achieve the desired effect, i.e., to treat acute and chronic wounds. The activity contemplated by the present methods includes both medical therapeutic and/or prophylactic treatment, as appropriate, including, for example, a reduction and/or alleviation of the signs, symptoms, or causes of a disease or disorder, or any other desired alteration of a biological system. The specific dose of a compound administered according to this invention to obtain therapeutic and/or prophylactic effects will, of course, be determined by the particular circumstances surrounding the case, including, for example, the specific polypeptide administered and the condition being treated. A therapeutically effective amount of compound of this invention is typically an amount such that when it is administered in a physiologically tolerable excipient composition, it is sufficient to achieve an effective intracellular concentration and local concentration in the tissue.

Generally speaking, the term "tissue" refers to any aggregation of similarly specialized cells which are united in the performance of a particular function. As used herein, "tissue", unless otherwise indicated, refers to tissue which includes elastin as part of its necessary structure and/or function.

The terms "treat," "treated," or "treating" as used herein refers to both therapeutic treatment and prophylactic or preventative measures, wherein the object is to prevent, ameliorate the effects of or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; reducing the severity of a symptom of a condition, disease or disorder; reducing the frequency of a symptom of a condition, disease or disorder; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. In some embodiments, treatment may include preventing or reducing scarring and/or promoting the regeneration of complex tissue structure and function following injury.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have an N-terminal and a C-terminal. The N-terminal will have an amino group, which may be free (i.e., as a NH2 group) or appropriately protected (for example, with a BOC or aFmoc group). The C-terminal will have a carboxylic group, which may be free (i.e., as a COOH group) or appropriately protected (for example, as a benzyl or a methyl ester). A cyclic peptide does not have free N- or C-terminal, since the ends are covalently bonded through an amide bond to form the cyclic structure. Amino acids may be represented by their full names (for example, leucine), 3-letter abbreviations (for example, Leu) and 1-letter abbreviations (for example, L). The structure of amino acids and their abbreviations can be found in the chemical literature, such as in Stryer, "Biochemistry", 3rd Ed., W. H. Freeman and Co., New York, 1988.

Excipients for use in topical gels are well-known in the art and examples may be found in the Handbook of Pharmaceutical Excipients (Rowe, R. C. et al, APhA Publications; $5^{th}$ ed., 2005). Exemplary excipients may include waxes, various sugars and types of starch, polymers, gels, emollients, thickening agents, rheology modifiers, humectants, glycerol, organic basic compounds, cellulose derivatives, gelatin, vegetable oils, polyethylene glycols and solvents. Examples of rheology modifiers include Carbopol, hydroxypropyl cellulose, $C_{26-28}$ alkyl dimethicone, $C_{26-28}$ alkyl methicone, polyphenylsisquioxane, trimethylsiloxysilicate, crosspolymers of cyclopentasiloxane and dimethicone/vinyltrimethylsiloxysilicate, fumed silica (e.g. Cab-O-Sil M5P), and mixtures thereof. Examples of emollients include glycerine, pentylene glycol, sodium pyrrolidone carboxylic acid, lanolin, saccharide isomerate, stearoxy dimethicone, stearyl dimethicone, and mixtures thereof. Emollients may be useful to prevent stratum corneum dehydration occurring due to the use of anhydrous solvents in the formulation. Examples of organic bases include 2-amino-2-methyl propanol, niacinamide, methanolamines, triethanolamines, Trisamino, AMP-95, AmP-Ultra PC 2000, triisopropanolamine, diisopropanolamine, Neutrol TE, Ethomeen, and mixtures thereof. The organic base may render the pH of the medicament basic or neutral.

Other exemplary excipients include water-soluble porogens. A water-soluble porogen is an additive that may facilitate water uptake and diffusion into the gel. Any suitable porogen may be used, but in some embodiments, the porogen may include sodium chloride, potassium chloride, sucrose, glucose, lactose, sorbitol, xylitol, polyethylene glycol, polyvinylpyrrollidone, polyvinyl alcohol or mixtures thereof.

Polymers may also act as excipients in topical gels. Exemplary polymers include hydrophilic polyurethanes, hydrophilic polyacrylates, co-polymers of carboxymethylcellulose and acrylic acid, N-vinylpyrrolidone, poly(hydroxy acids), polyanhydrides, polyorthoesters, polyamides, polycarbonates, polyalkylenes (e.g., polyethylene and polypropylene), polyalkylene glycols (e.g., poly(ethylene glycol)), polyalkylene oxides (e.g., polyethylene oxide), polyalkylene terephthalates (e.g., polyethylene terephthalate), polyvinyl alcohols, polyvinyl ethers, polylvinyl esters, polyvinyl halides (e.g., poly(vinyl chloride)), polyvinylpyrrolidone, polysiloxanes, poly(vinyl acetates), polystyrenes, polyurethane copolymers, cellulose, derivatized celluloses (e.g., hydroxyethyl cellulose, hydroxypropyl cellulose, hydroxypropyl methyl cellulose, methylcellulose, ethylcellulose, carboxymethyl cellulose, or cellulose acetate), alginates, poly(acrylic acid), poly(acrylic acid) derivatives, acrylic acid copolymers, methacrylic acid, methacrylic acid derivatives, methacrylic acid copolymers, poly(butyric acid), poly(valeric acid), poly(lactide-co-caprolactone), copolymers thereof and blends thereof.

In some embodiments of the invention, the polymers may be superabsorbent polymers (SAPs). A polymer is considered superabsorbent, as defined per IUPAC, as a polymer that can absorb and retain extremely large amounts of water relative to its own mass. SAPs may absorb water up to 500 times their own weight and may swell up to 1000-times their original volume. Particular SAPs of interest include sodium polyacrylate, the polyurethane Tecophilic TG-2000, and polymers prepared by the use of polyacrylamide copolymer, ethylene maleic anhydride copolymer, cross-linked carboxymethyl-cellulose, polyvinyl alcohol copolymers, polyvinylpyrrolindone and cross-linked polyethylene oxide.

In some embodiments of the invention, polymers that are relatively hydrophobic may be used. Any suitable hydrophobic polymer may be used. However, exemplary polymers that are relatively hydrophobic include aromatic polyurethanes, silicone rubber, polysiloxanes, polycaprolactone, polycarbonate, polyvinylchloride, polyethylene, poly-L-lactide, poly-DL-glycolide, polyetheretherketone (PEEK), polyamide, polyimide and polyvinyl acetate. In addition, a hydrophobic gel-base and/or rheology modifier may be used.

In some embodiments of the invention, the polymers may act as thickening agents in the medicaments. Specifically, the polymeric portion of the gel may act as a visco-elastic substance and may retain the gel at the site of application, along with the alpha connexin polypeptides dispersed therein.

In some other embodiments, a gel that includes a polymer may have spreadability such that it forms a thin film when applied on the skin surface. This film may enable the application of the contained alpha connexin polypeptides over a wide area, and may serve to maintain the alpha connexin polypeptides on the affected area of the skin.

Other excipients may include various ionic or non-ionic compounds to maintain stability of the formulation, thereby protecting from the de-emulsification, settling, agglomeration or degradation of the formulation constituents that may reduce its therapeutic or aesthetic value.

Examples of ionic compounds may include salts such as sodium chloride, potassium chloride; cationic, anionic or zwitterionic surfactants such as sodium dodecyl sulfate (SDS), perfluorooctanoate (PFOA), perfluorooctanesulfonate (PFOS), ammonium lauryl sulfate (ALS), sodium lauryl ether sulfate (SLES), alkyl benzene sulfonate, cetyl trimethylammonium bromide (CTAB), cetylpyridinium chloride (CPC), polyethoxylated tallow amine (POEA), benzalkonium chloride (BAC), benzethonium chloride, dodecyl betaine, cocamidopropyl betaine and cocoampho glycinate.

Examples of non-ionic compounds that may act as excipients include non-ionic surfactants such as Pluronic, Tween, AMP, and Brij family of surfactants; and surfactants derived from biological sources, e.g., natural or semi-synthetic surfactants, such as oleic acid, sorbitan trioleate, sorbitan monooleate, lecithin, cocamide MEA, cocamide DEA and cocamidopropyl betaine. Surfactants (both ionic and non-ionic) may reduce the interfacial surface energy and may facilitate spreading of the topical formulation over a wider area.

In some embodiments of the invention, solvent excipients may be used as a carrier vehicle for the alpha connexin polypeptides and other excipients. The polymer chains may interact with the solvent and undergo swelling to form a network that may impart visco-elastic properties to the topical formulation. In some embodiments of the topical formulation, the solvent may evaporate upon application, leaving a residual film of the polymer along with the entrapped alpha connexin polypeptides.

Exemplary solvent excipients that may be useful in hydrophilic formulations may include dimethyl isosorbide, propylene glycol, glycerol, isopropanol, ethanol, benzyl alcohol, ethylene glycol, polyethylene glycol, ethoxydiglycol or mixtures thereof. Exemplary solvent excipients that may be useful in hydrophobic formulations may include capric/caprylic triglycerides, isopropyl myristate, mineral oil, isododecane, isodecyl neopentanoate, butylene glycol, pentylene glycol, hexylene glycol, methoxypolyethyleneglycol, cyclopentasiloxane, cyclotetrasiloxane, dimethicone, caprylyl methicone or mixtures thereof.

In addition to the alpha connexin polypeptides and excipients, the topical formulation may also include at least one additional therapeutic agent such as antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents and mixtures thereof.

Examples of antimicrobial agents include penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, Linezolid, Synercid, Aztreonam, and Metronidazole, Epiroprim, Sanfetrinem sodium, Biapenem, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil.

Examples of topical anti-acne agents include adapalene, azelaic acid, benzoyl peroxide, clindamycin and clindamycin phosphate, doxycycline, erythromycin, keratolytics such as salicylic acid and retinoic acid (Retin-A"), norgestimate, organic peroxides, retinoids such as isotretinoin and tretinoin, sulfacetamide sodium, and tazarotene. Particular anti-acne agents include adapalene, azelaic acid, benzoyl peroxide, clindamycin {e.g., clindamycin phosphate), doxycycline {e.g., doxycycline monohydrate), erythromycin, isotretinoin, norgestimate, sulfacetamide sodium, tazarotene, etretinate and acetretin.

Examples of antihistamine agents include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include nonsteroidal antiinflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21—monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocaine; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include thrombin, phytonadione, protamine sulfate, aminocaproic acid, tranexamic acid, carbazochrome, carbaxochrome sodium sulfanate, rutin and hesperidin.

Beside the bioactive polypeptide component, the instant invention may also contain other active agents such as niacinamide, phytantriol, farnesol, bisabolol and salicylic acid. It is expected that certain additional active agents will act synergistically with the bioactive peptide component, or will enhance the shelf-life of the formulation.

Examples of wound treatments that may be used together with the drug product of the present invention include fibrinolytic enzymes, such as fibrinolysin, deoxyribonuclease, streptokinase, and streptodornase, necrotomy tissue agents containing lysozyme chloride, antimicrobial agents containing gentamicin sulfate, sulfadiazine silver, bacitracin, and fradiomycin sulfate, incarnant agents containing trafermin, bucladesine sodium, tretinoin tocoferil (tocoretinate), alprostadil alfadex, solcoseryl (extract from hemolysed blood of young cattle), and alcloxa, iodine preparations containing white soft sugar, povidone iodine, and iodine, and preparations containing bendazac, dimethyl isopropylazulene (guaiazulene), and epinephrine as active ingredients.

In addition to the alpha connexin polypeptides, excipients, and other therapeutic agents, the gels may also include other compounds that improve the organoleptic properties of the topical formulation.

Examples of such compounds include perfumes, dyes and colorants; chelating agents including but not limited to edetate disodium (EDTA), EGTA, CP94, citric acid; preservatives including but not limited to quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Alpha connexin polypeptides that may be used in the formulation of the present invention are described in U.S. Pat. No. 7,786,074, which is hereby incorporated by reference. In some embodiments, the alpha connexin polypeptide is a full length alpha connexin protein such as connexin 37, connexin 40, connexin 43, or connexin 45. In some embodiments, the polypeptide does not comprise the full-length connexin protein.

Peptides useful in the formulations of the present invention include alpha connexin polypeptides. The alpha connexin polypeptides useful in the formulations of the present invention may comprise or consist of the carboxy-terminal most 4 to 30 contiguous amino acids of an alpha connexin protein or conservative variant thereof. Thus, the polypeptides useful in the formulations can comprise the c-terminalmost 4 to 30 amino acids of the alpha Connexin, including the c-terminal most 4, 5, 6, 7, 8, 9, 10, 11, 12, 13, 14, 15, 16, 17, 18, 19, 20, 21, 25 22, 23, 24, 25, 26, 27, 28, 29, 30 amino acids of the alpha Connexin. In some aspects, the provided polypeptide further comprises a deletion of one or more amino acids of the c-terminal-most 4 to 30 amino acids of the alpha Connexin, including a deletion of 1, 2, 3, 4, 5, 6, 7, 8, 9, or 10 amino acids of the c-terminal-most 4 to 30 amino acids of the alpha Connexin. For example, in some aspects, the polypeptides useful in the formulations of the present invention do not comprise the c-terminal-most 1, 2, or 3 amino acids of the alpha Connexin. For example, the polypeptides can consist essentially of the amino acid sequence SEQ ID NO:92, or a carboxy terminal fragment thereof of at least 4, 5, 6, 7, 8, 9, 10 amino acids in length.

In certain embodiments, the alpha connexin polypeptide of the present invention is linked at its amino or carboxy terminus to a cellular internalization transporter. Separate embodiments include the alpha connexin polypeptide without any cellular internalization transporter attached. The cellular internalization transporter linked to the alpha connexin polypeptides may be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (BisGuanidinium-Tren-Cholesterol).

In one embodiment of the present invention, the amino acid sequence of the alpha connexin polypeptide is selected from the group consisting of SEQ ID NOs: 1, 2, 3, 4, and 5, or a conservative variant thereof. In a further embodiment of the present invention, the alpha connexin polypeptide comprises the amino acid sequence of SEQ ID NO: 2. In another embodiment of the present invention, the polypeptide comprises an alpha connexin polypeptide and a cellular internalization transporter. In a further embodiment, the alpha connexin polypeptide is linked at is amino terminus to the cellular internalization transporter. In a yet further embodiment, the amino acid sequence of the alpha connexin polypeptide linked to the cellular internalization transporter is selected from the group consisting of SEQ ID NO: 8, 9, 10, 11, and 12, or a conservative variant thereof. In one embodiment, the polypeptide consists of or comprises the amino acid sequence of SEQ ID NO: 9, namely, RQP-KIWFPNRRKPWKKRPRPDDLEI.

When specific proteins are referred to herein, variants, derivatives, and fragments are contemplated. Protein variants and derivatives are well understood to those of skill in the art and can involve amino acid sequence modifications.

For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues, but can occur at a number of different locations at once; insertions usually will be on the order of about from 1 to 10 amino acid residues. Deletions or insertions may be made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place. Such substitutions generally are referred to as conservative substitutions. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions Conservatively substituted variations of each explicitly disclosed sequence are included within the polypeptides provided herein. Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions. A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids. Further information about conservative substitutions can be found in, among other locations, in Ben-Bassat et al., (*J. Bacterial.* 169:751-7, 1987), O'Regan et al., (*Gene* 77:237-51, 1989), Sahin-Toth et al., (Protein Sci. 3:240-7, 1994), Hochuli et al., (*Bio/Technology* 6:1321-5, 1988) and in standard textbooks of genetics and molecular biology.

As used herein, "analytical methods" includes the following techniques that are useful for determining the identity and quantity of the ACT peptide in a particular formulation: NMR, HPLC, Amino Acid Composition and Molecular Weight Determinations, and Specific Optical Rotation.

The present invention includes a topical formulation comprising at least one alpha connexin polypeptide and hydroxyethylcellulose gel, wherein the hydroxyethylcellulose gel stabilizes the alpha connexin polypeptide. In certain embodiments, the hydroxyethylcellulose gel stabilizes the alpha connexin polypeptide so that after 3 months of storage at 5° C. at least 80%, 81%, 82%, 83%, 84%, 85%, 86%, 87%, 88%, 89%, 90%, 91%, 92%, 93%, 94%, 95%, 96%, 97%, 98%, 99%, or 100% of the alpha connexin polypeptide is detectable by analytical methods. In some embodiments, the alpha connexin polypeptide is present in the formulation at a concentration of about 0.0025% (w/w), of about 0.005% (w/w), of about 0.0075% (w/w), of about 0.010% (w/w), of about 0.015% (w/w), of about 0.020% (w/w), of about 0.025% (w/w), of about 0.030% (w/w), of about 0.035% (w/w), of about 0.040% (w/w), of about 0.045% (w/w), of about 0.050% (w/w), of about 0.055% (w/w), of about 0.060% (w/w), of about 0.065% (w/w), of about 0.070% (w/w), of about 0.075% (w/w), of about 0.080% (w/w), of about 0.085% (w/w), of about 0.090% (w/w), of about 0.095% (w/w), of about 0.100% (w/w), of about 0.150% (w/w), of about 0.200% (w/w), of about 0.250% (w/w), of about 0.50% (w/w), of about 0.750% (w/w), of about 1.00% (w/w), of about 1.50% (w/w), of about 2.00% (w/w), of about 2.50% (w/w), or of about 5.00 (w/w). In one embodiment, the alpha connexin polypeptide is present in the formulation at a concentration of between about 0.005% (w/w) and about 1.00% (w/w).

In other embodiments, the drug product of the invention is a clear colorless gel which contains 0.0072% (w/w) (20 μM) of the ACT peptide, 0.018% (w/w) (50 μM) of the ACT peptide, 0.036% (w/w) (100 μM) of the ACT peptide, or 0.072% (w/w) (200 μM) of the ACT peptide. The ACT peptide may be dissolved in a semisolid dosage form that contains >0% water, >10% water, >20% water, >30% water, >40% water, >50% water, >60% water, >70% water, >80% water, or >90% water and 0.25% gelling agent (polymer), 0.55% gelling agent (polymer), 0.75% gelling agent (polymer), 1.00% gelling agent (polymer), 1.25% gelling agent (polymer), 1.50% gelling agent (polymer), 1.75% gelling agent (polymer), 2.00% gelling agent (polymer), 2.25% gelling agent (polymer), or 2.50% gelling agent (polymer). The ACT peptide may be well preserved and adequately buffered to pH 6. In one embodiment of the topical formulation, the qualitative and quantitative composition is that listed in Table 1.

TABLE 1

Drug Product Gel Qualitative & Quantitative Composition

| Ingredients | Grade | Function | Concentration (% w/w) |
|---|---|---|---|
| Peptide 328967 (ACT peptide) | — | Active | 0.0072; 0.018 0.036; 0.072 |
| Methylparaben | NF | Preservative | 0.17 |
| Propylparaben | NF | Preservative | 0.02 |
| Glycerin | USP | Solvent | 5.0 |
| Sodium Phosphate Monobasic | USP | Buffer Agent | 0.263 |
| Sodium Phosphate Dibasic | USP | Buffer Agent | 0.044 |
| Propylene Glycol | USP | Solvent | 3.0 |
| Edetate Disodium (EDTA) | USP | Chelating Agent | 0.05 |

TABLE 1-continued

Drug Product Gel Qualitative & Quantitative Composition

| Ingredients | Grade | Function | Concentration (% w/w) |
|---|---|---|---|
| D-Mannitol | USP | Stabilizer | 0.05 |
| Hydroxyethylcellulose, 250HHX | NF | Gelling Agent | 1.25% |
| Purified Water, qsad | USP | Solvent | 100% |

The ACT1 peptide sequence is listed in Table 2 below in which Ahx refers to L-2-aminohexanoic acid, also known as 6-aminohexanoic acid:

TABLE 2

Peptide 328967 (Antp/ACT1) sequence.

Biotin-Ahx-Arg-Gln-Pro-Lys-Ile-Trp-Phe-Pro-Asn-
Arg-Arg-Lys-Pro-Trp-Lys-Lys-Arg-Pro-Arg-Pro-Asp-
Asp-Leu-Glu-Ile-OH The general properties of the Peptide 328967 are listed in Table 3.

TABLE 3

General Physical Properties of Peptide 328967

| Physical Appearance | White to off-white powder |
| Molecular Weight | 3597.33 ± 2.0 amu |
| Counter-Ion | AcOH |
| Solubility | Soluble in water at room temperature |

In one aspect of the invention, the excipients used in the drug product topical preparation are selected from the group consisting of or are one or more of the following:
Methylparaben
Propylparaben
Glycerin
Sodium Phosphate Monobasic
Sodium Phosphate Dibasic
Propylene Glycol
Edetate Disodium (EDTA)
D-Mannitol
Hydroxyethylcellulose, 250 HHX
Purified Water In one embodiment, the drug product topical preparation comprises a peptide, D-mannitol, hydroxyethylcellulose, and purified water. Said preparation may further comprise one or more of methylparaben, propylparaben, glycerin, sodium phosphate monobasic, sodium phosphate dibasic, propylene glycol, and edetate disodium (EDTA). In a further embodiment, the hydroxyethylcellulose is 250 HHX. In a further embodiment, the peptide is an alpha connexin polypeptide.

In such embodiments, the drug product topical preparation comprises a peptide at a concentration between about 0.001% (w/w) and about 0.5% (w/w) (for example, at about 0.0072%, 0.018%, 0.036%, or 0.072% (w/w)); methylparaben at a concentration between about 0.10% (w/w) and about 0.25% (w/w) (for example, about 0.17% (w/w)); propylparaben at a concentration between about 0.01% (w/w) and about 0.03% (w/w) (for example, about 0.02% (w/w)); glycerin at a concentration between about 1% (w/w) and about 10% w/w) (for example, about 5% (w/w)); sodium phosphate monobasic at a concentration between about 0.1% (w/w) and about 0.5% (w/w) (for example, about 0.263% (w/w)); sodium phosphate dibasic at a concentration between about 0.02% and about 0.06% (for example, about 0.044% (w/w)); propylene glycol at a concentration between about 1% (w/w) and about 5% (w/w) (for example, about 3% (w/w)); EDTA at a concentration between about 0.01% and about 0.1% (for example, about 0.05% (w/w)); D-mannitol at a concentration between about 0.01% (w/w) and about 0.1% (w/w) (for example, about 0.05% (w/w)); hydroxyethylcellulose at a concentration between about 0.5% and about 2.5% (for example, about 1.25% (w/w)), and purified water at a concentration of about 0.1% to about 10% (for example, about 1%). In a further embodiment, the peptide is an alpha connexin polypeptide. In a yet further embodiment, the peptide comprises an amino acid sequence selected from the group consisting of SEQ ID NO: 1, 2, 3, 4, 5, 8, 9, 10, 11, and 12. In one embodiment, the peptide comprises an amino acid sequence according to SEQ ID NO: 9.

Derived through in vitro and in vivo studies, these stabilizers and excipients are incorporated into the drug product since they are non-irritating, non-staining, and non-immunogenic. Stability studies showed that the ACT1 peptide is more stable in the gelling agent Hydroxyethylcellulose, 250 HHX (1.25%) compared to Pluronic gels. The ACT peptide within the drug product containing 1.25% hydroxyethylcellulose only dropped to 98% of the label claim (i.e., initial concentration) when stored at 5° C. for three months and to 84% of the label claim when stored at 25° C. for the same duration. In one aspect of the invention, edetate disodium (EDTA) and Mannitol are incorporated within the drug product to provide stability to the ACT1 peptide. In some embodiments of the invention, the Mannitol is present in the formulation at 0.01% (w/w) to 1.6% (w/w), 0.01% (w/w) to 1.5% (w/w), 0.01% (w/w) to 1.4% (w/w), 0.01% (w/w) to 1.3% (w/w), 0.01% (w/w) to 1.2% (w/w), 0.01% (w/w) to 1.1% (w/w), 0.01% (w/w) to 1.0% (w/w), 0.01% (w/w) to 0.9% (w/w), 0.01% (w/w) to 0.8% (w/w), 0.01% (w/w) to 0.7% (w/w), 0.01% (w/w) to 0.6% (w/w), 0.01% (w/w) to 0.5% (w/w), 0.01% (w/w) to 0.4% (w/w), 0.01% (w/w) to 0.3% (w/w), 0.01% (w/w) to 0.2% (w/w), 0.01% (w/w) to 0.1% (w/w), or 0.01% (w/w) to 0.0.05% (w/w). In one embodiment, the Mannitol is present in the formulation at about 0.05% (w/w).

In another aspect of the present invention, a buffering agent is included in the topical formulation to maintain the pH in a certain range. Suitable buffering agents can include, but are not limited to, acetate buffers, citrate buffers, phosphate buffers, lactic acid buffers, malic acid buffers, succinic acid buffers, borate buffers, sodium hydroxide, potassium hydroxide, and ammonium hydroxide. Phosphate salts such as monosodium phosphate ($NaH_2PO_4$; also known as monobasic sodium phosphate), disodium hydrogen phosphate ($Na_2HPO_4$; also known as dibasic sodium phosphate), monopotassium phosphate ($KH_2PO_4$), dipotassium phosphate ($K_2HPO_4$), and mixtures thereof can also be used. In one embodiment, phosphate buffer provides superior stability compared to citrate buffer. A buffer capacity at 25 mM was found to be adequate for the drug product. Buffer is needed to control pH of the gel system and to maintain stability of the peptide drug. The pH range of the topical formulation may be pH 2 to pH 12, pH 4 to pH 10, or pH 6 to pH 8. In one embodiment, the proper pH range is in the range of 5 to 7. In some embodiments, the pH of the topical formulation of the present invention is 4.0, 4.5, 5.0, 5.5, 6.0, 6.5, 7.0, 7.5, or 8.0. In yet another aspect, propylene glycol in the amount of 3% provides better solubilization of parabens in the aqueous system.

In one embodiment, the formulation with an ACT peptide incorporated into hydroxyethylcellulose enables large scale manufacturing of a product with the characteristics that make it practical for clinical treatments as well as meeting desired storage and stability requirements. While a formulation for ACT1 using Pluronic gel may require a relatively long incorporation time of approximately 2.5 hours and only yield 50 gram batches, a formulation with hydroxyethylcellulose provides allows for significantly faster incorporation of the ACT peptide into the gel and yields much larger batches. For example, when using Pluronic F 127 gel in the topical formulation it takes over an hour to incorporate the polymer, and the formulation needs to be placed in a water bath to help with incorporation. In contrast, hydroxyethylcellulose (e.g., HEC 250 HHX) is easily incorporated at room temperature and hydrates within 30 minutes. Thus, the use of hydroxyethylcellulose may facilitate large scale manufacturing. The manufacturing process with Pluronic gel may require a cold bath to bring its viscosity into a desired range and require more energy than the manufacturing process with hydroxyethylcellulose. In addition, the final formulation in Pluronic gel may be very thin at a storage condition of 5 degrees C.

It has been discovered that hydroxyethylcellulose (HEC) is a suitable gelling agent and acceptable carrier of the drug product of the present invention. In one embodiment, the gelling agent is Hydroxyethylcellulose (HEC), 250 HHX. In one embodiment, the percent (w/w) of HEC is in the range of 1-5%. In a further embodiment, the percent (w/w) of HEC is 1.25%. In the manufacture of HEC, a purified cellulose is reacted with sodium hydroxide to produce a swollen alkali cellulose. The alkali-treated cellulose is more chemically reactive than cellulose. By reacting the alkali cellulose with ethylene oxide, a series of hydroxyethylcellulose ethers is produced. In this reaction, the hydrogen atoms in the hydroxyl groups of cellulose are replaced by hydroxyethyl groups, which confer water solubility to the gel. It is contemplated in this invention that a single HEC ether may be used, or a mixture of HEC ethers of difference molecular weight and structure may be used. Suitable grades of HEC for pharmaceutical purposes are well known and full described in the pharmaceutical literature. Suitable commercially available brands of HEC include but are not limited to Fuji HEC-HP; Fuji HEC-AG 15; NATRO-SOL 250HR; NATROSOL 250MH; NATROSOL 250G; CELLOSIZE QP 30000; TYLOSE H SERIES; NATROSOL 180L; NATROSOL 300H; TYLOSE P-X; NATROSOL 250M; CELLOSIZE WP 4400; CELLOSIZE UT 40; NATROSOL 250H4R; Tylose H 20P; NATROSOL LR; TYLOSE MHB; NATROSOL 250HHP; HERCULES N 100; CELLOSIZE WP 300; TYLOSE P-Z SERIES; NATROSOL 250H; TYLOSE PS-X; Cellobond HEC 400; CELLOSIZE QP; CELLOSIZE QP 1500; NATRO-SOL 250; HYDROXYETHYL CELLULOSE ETHER; HESPAN; TYLOSE MHB-Y; NATROSOL 240JR; HYDROXYETHYL STARCH; CELLOSIZE WP; CELLOSIZE WP 300H; 2-HYDROXYETHYL CELLULOSE ETHER; BL 15; CELLOSIZE QP 4400; CELLOSIZE QP3; TYLOSE MB; CELLULOSE HYDROXY-ETHYLATE; CELLOSIZE WPO 9H17; CELLOSIZE 4400H16; CELLULOSE HYDROXYETHYL ETHER; Hydroxyethyl Cellulose; Hydroxyl Ethyl Cellulose (HEC); Hydroxyethyl Cellulose 100H (celocell 100h); TYLOSE M-XP; NATROSOL 250HX; Natrosol; Daicel EP 500; HEC-Unicel; HEC (Hydroxyethyl cellulose); Cellosize; HEC-Al 5000; Fuji HEC-AL 15; HEC-Unicel QP 09L; Cellulose, ethers, 2-hydroxyethyl ether; Unicel QP 52000H; HEC-QP 4400; SP 250 (cellulose); Hetastarch; Cellulose, ethers,2-hydroxyethyl ether; Glutofix 600; FL 52; Fuji HEC-AX 15F; Tylose H 300P; HEC-Unicel QP 300H; Tylose H 300; Daicel SP 550; Daicel SE 600; Unicel QP 15000; HEC-QP 100MH; HEC-QP 9H; OETs; Daicel EP 850; H. E. Cellulose; Cellobond 25T; Unicel QP 100MH; Tylose H 4000; SE 850K; Tylomer H 20; Daicel SE 850K; Tylose H 30000YP; Unicel QP 4400; SP 407; Tylose H 100000; Daicel SP 200; Culminal HEC 5000PR; Tylopur H 300; Daicel SP 750; Sanhec; BL 15 (cellulose derivative); Unicel QP 300H; Tylomer H 200; J 164; Tylose H 10; Tylose H 20; AH 15; Daicel SP 600; Daicel SE 900; HEC-Unicel QP 4400H; AX 15; Daicel SP 800; Fuji HEC-AW 15F; HEC-SE 850; HEC-A 5-25CF; Metolose 90SEW; AW 15 (polysaccharide); Cellobond HEC 5000; HEC-QP 100M; Cellobond HEC 15A; Tylose H 15000YP2; Walocel HT 6.000PFV; 2-Hydroxyethyl cellulose (Natrosol Type 250HRCS); Fuji HEC-BL 20; Fuji HEC-SY 25F; Telhec; HEC-SP 200; HEC-AH 15; HEC-Unicel QP 30000H; see; HEC 10A; Daicel SP 400; Admiral 3089FS; Fuji HEC-A 5000F; HEC-SP 400; Hydroxyethyl Methyl Cellulose (HEMC); HYDROXYETHYL CELLULOSE (HEC); Hydroxyethyl Starch (CAS No: 9004-62-0); Hydroxy Ethyl Cellulose; "Natrosol" [Aqualon]; HEC; 2-HYDROXYETHYL CELLULOSE; NATROSOL 150L; TYLOSE MHB-YP; HYDROXYETHYL ETHER CELLULOSE; NATROSOL 250L; CELLOSIZE WP 400H; TYLOSE P; CELLULOSE, 2-HYDROXYETHYL ETHER; TYLOSE MH-K; NATROSOL 250HHR.

In another embodiment, the drug product of the present invention is packaged in 20 mL vial (USP Type I, Borosilicate clear scintillation glass with poly-seal cone urea screw cap). A mixture of methylparaben at 0.17% (w/w) and propylparaben 0.02% (w/w) is used as a preservative.

In some embodiments, the present invention includes a method of wound treatment comprising administering to a subject in need thereof a topical formulation comprising at least one alpha connexin polypeptide and hydroxyethylcellulose gel, wherein the hydroxyethylcellulose gel stabilizes the alpha connexin polypeptide. The wound treated may be an acute surgical wound or a chronic, non-infected, full-thickness lower extremity ulcer.

In a certain embodiment, the drug product of the present invention may be used to mitigate excessive scar formation associated with acute surgical wounds. In this embodiment, the drug product of the present invention may be applied at the time of surgical incision closure, 1 hour after surgical incision closure, 2 hours after surgical incision closure, 3 hours after surgical incision closure, 4 hours after surgical incision closure, 5 hours after surgical incision closure, 6 hours after surgical incision closure, 7 hours after surgical incision closure, 8 hours after surgical incision closure, 9 hours after surgical incision closure, 10 hours after surgical incision closure, 11 hours after surgical incision closure, 12 hours after surgical incision closure, 13 hours after surgical incision closure, 14 hours after surgical incision closure, 15 hours after surgical incision closure, 16 hours after surgical incision closure, 17 hours after surgical incision closure, 18 hours after surgical incision closure, 19 hours after surgical incision closure, 20 hours after surgical incision closure, 21 hours after surgical incision closure, 22 hours after surgical incision closure, 23 hours after surgical incision closure, 24 hours after surgical incision closure, 48 hours after surgical incision closure, 72 hours after surgical incision closure, or thereafter.

In another embodiment, the drug product of the present invention may be used to treat chronic ulcers. For example, ulcers may include diabetic foot ulcers, venous leg ulcers, and pressure ulcers. These ulcers may be chronic, non-infected, full-thickness lower extremity ulcers. In one embodiment, the drug product of the present invention may be applied to a chronic ulcer in a daily regimen, a regimen of every other day, a regimen of once a week, or in various other regimens until healing of the chronic ulcer is apparent. In another embodiment, the drug product of the present invention may be applied to a chronic ulcer in a regimen at day 0, 3, 7, 14, 21, and 28. In another embodiment, the drug product of the present invention may be applied to a chronic ulcer in a regimen at day 0, day 3, week 1, week 2, week 3, week 4, week 5, week 6, week 7, week 8, week 9, week 10, week 11, and week 12. In another aspect of the present invention, the drug product is manufactured with the following steps:

Step 1: In a suitable size of beaker, add propylene glycol, glycerin, methylparaben and propylparaben. Mix with a propeller until the parabens are completely dissolved.

Step 2: In a manufacturing vessel, add purified water (part I), EDTA, monobasic sodium phosphate, dibasic sodium phosphate and D-mannitol. Mix with a propeller until a clear solution is obtained.

Step 3: Add the solution from step 1 to the manufacturing vessel. Rinse the beaker with purified water (part II, divided into approximately 3 equal portions) and add the rinse back to the vessel. Continue with propeller mixing until the solution is visually homogeneous.

Step 4: With homogenization mixing, add hydroxyethyl cellulose into the manufacturing vessel from Step 3. Mix until the polymer is fully dispersed.

Step 5: In a separate beaker, add purified water (part III) and an alpha connexin polypeptide (e.g., Peptide 328967 ACT1 peptide). Mix with a stir bar or propeller mixer until the peptide is completely dissolved and a gel is formed.

Step 6: With continuous propeller mixing, add the drug solution from step 5 to the manufacturing vessel. Rinse the beaker with purified water (part IV, divided into approximately 3 equal portions) and add the rinse back to the vessel. Mix until the gel is homogeneous.

The manufacturing process flow chart is provided in FIG. 1 Manufacturing Process Flow Chart.

```
Sequences
SEQ ID NO: 1 (ACT 2)
PSSRASSRASSRPRPDDLEI

SEQ ID NO: 2 (ACT 1)
RPRPDDLEI

SEQ ID NO: 3 (ACT 3)
RPRPDDLEV

SEQ ID NO: 4 (ACT 4)
RPRPDDVPV

SEQ ID NO: 5 (ACT 5)
KARSDDLSV

SEQ ID NO: 6
aga cct cgg cct gat gac ctg gag att

SEQ ID NO: 7 (Antp)
RQPKIWFPNRRKPWKK

SEQ ID NO: 8 (Antp/ACT 2)
RQPKIWFPNRRKPWKKPSSRASSRASSRPRPDDLEI
```

SEQ ID NO: 9 (Antp/ACT 1)
RQPKIWFPNRRKPWKKRPRPDDLEI

SEQ ID NO: 10 (Antp/ACT 3)
RQPKIWFPNRRKPWKKRPRPDDLEV

SEQ ID NO: 11 (Antp/ACT 4)
RQPKIWFPNRRKPWKKRPRPDDVPV

SEQ ID NO: 12 (Antp/ACT 5)
RQPKIWFPNRRKPWKKKARSDDLSV

SEQ ID NO: 13 (encodes polypeptide of SEQ ID NO 9)
cgg cag ccc aag atc tgg ttc ccc aac cgg cgg aag ccc tgg aag aag cgg ccc ggc ccg acg acc tgg aga tc SEQ ID NO: 14 (HIV-Tat)
GRKKRRQRPPQ SEQ ID NO: 15 (Penetratin)
RQIKIWFQNRRMKWKK SEQ ID NO: 16 (Antp-3A)
RQIAIWFQNRRMKWAA SEQ ID NO: 17 (Tat)
RKKRRQRRR SEQ ID NO: 18 (Buforin II)
TRSSRAGLQFPVGRVHRLLRK SEQ ID NO: 19 (Transportan)
GWTLNSAGYLLGKINKALAALAKKIL SEQ ID NO: 20 (model amphipathic peptide)
KLALKLALKALKAALKLA

SEQ ID NO: 21 (K-FGF)
AAVALLPAVLLALLAP

SEQ ID NO: 22 (Ku70)
VPMLK-PMLKE

SEQ ID NO: 23 (Prion)
MANLGYWLLALFVTMWTDVGLCKKRPKP

SEQ ID NO: 24 (pVEC)
LLIILRRRIRKQAHAHSK

SEQ ID NO: 25 (Pep-1)
KETWWETWWTEWSQPKKKRKV

SEQ ID NO: 26 (SynB1)
RGGRLSYSRRRFSTSTGR

SEQ ID NO: 27 (Pep-7)
SDLWEMMMVSLACQY

SEQ ID NO: 28 (HN-1)
TSPLNIHNGQKL

SEQ ID NO: 29 (Chick alpha Cx43 ACT)
PSRASSRASSRPRPDDLEI

SEQ ID NO: 30 (Human alpha Cx45)
GSNKSTASSKSPDPKNSVWI

SEQ ID NO: 31 (Chick alpha Cx45)
GSNKSSASSKSGDGKNSVWI

SEQ ID: 32 (Human alpha Cx46)
GRASKASRASSGRARPEDLAI

SEQ ID: 33 (Human alpha Cx46.6)
GSASSRDGKTVWI

SEQ ID NO: 34 (Chimp alpha Cx36)
PRVSVPNFGRTQSSDSAYV

SEQ ID NO: 35 (Chick alpha Cx36)
PRIVISMPNFGRTQSSDSAYV

SEQ ID NO: 36 (Human alpha Cx47)
PRAGSEKGSASSRDGKTTVWI

SEQ ID NO: 37 (Human alpha Cx40)
GYHSDKRRLSKASSKARSDDLSV

SEQ ID NO: 38 (Human alpha Cx50)
PLSRLSKASSRARSDDLTV

SEQ ID NO: 39 (Human alpha Cx59)
PNHVVSLTNNLIGRRVPTDLQI

SEQ ID NO: 40 (Rat alpha Cx33)
PSCVSSSAVLTTICSSDQVVPVGLSSFYM

SEQ ID NO: 41 (Sheep alpha Cx44)
GRSSKASKSSGGRARAADLAI

SEQ ID NO: 42 (Human beta Cx26)
LCYLLIRYCSGKSKKPV

SEQ ID: 43 (Human alpha Cx37)
GQKPPSRPSSSASKKQ*YV

SEQ ID 44: (conservative Cx43 variant)
SSRASSRASSRPRPDDLEV

SEQ ID 45: (conservative Cx43 variant)
RPKPDDLEI

SEQ ID 46: (conservative Cx43 variant)
SSRASSRASSRPKPDDLEI,

SEQ ID 47: (conservative Cx43 variant)
RPKPDDLDI

SEQ ID 48: (conservative Cx43 variant)
SSRASSRASSRPRPDDLDI

SEQ ID 49: (conservative Cx43 variant)
SSRASTRASSRPRPDDLEI

SEQ ID 50: (conservative Cx43 variant)
RPRPEDLEI

SEQ ID 51: (conservative Cx43 variant)
SSRASSRASSRPRPEDLEI,

SEQ ID 52: (conservative Cx45 variant)
GDGKNSVWV

SEQ ID 53: (conservative Cx45 variant)
SKAGSNKSTASSKSGDGKNSVWV

SEQ ID 54: (conservative Cx37 variant)
GQKPPSRPSSSASKKLYV

SEQ ID NO: 55 (non-active control peptide)
RQPKIWFPNRRKPWKIELDDPRPR

SEQ ID NO: 56 (HIV-Tat/ACT 1)
GRKKRRQRPPQ RPRPDDLEI

SEQ ID NO: 57 (Penetratin/ACT 1)
RQIKIWFQNRRMKWKK RPRPDDLEI

SEQ ID NO: 58 (Antp-3A/ACT 1)
RQIAIWFQNRRMKWAA RPRPDDLEI

SEQ ID NO: 59 (Tat/ACT 1)
RKKRRQRRR RPRPDDLEI

SEQ ID NO: 60 (Buforin II/ACT 1)
TRSSRAGLQFPVGRVHRLLRK RPRPDDLEI

-continued

SEQ ID NO: 61 (Transportan/ACT 1)
GWTLNSAGYLLGKINKALAALAKKIL RPRPDDLEI

SEQ ID NO: 62 (MAP/ACT 1)
KLALKLALKALKAALKLAR PRPDDLEI

SEQ ID NO: 63 (K-FGF/ACT 1)
AAVALLPAVLLALLAP RPRPDDLEI

SEQ ID NO: 64 (Ku70/ACT 1)
VPMLKPMLKER PRPDDLEI

SEQ ID NO: 65 (Prion/ACT 1)
MANLGYWLLALFVTMWTDVGLCKKRPKPRPRPDDLEI

SEQ ID NO: 66 (pVEC/ACT 1)
LLIILRRRIRKQAHAHSK RPRPDDLEI

SEQ ID NO: 67 (Pep-1/ACT 1)
KETWWETWWTEWSQPKKKRKV RPRPDDLEI

SEQ ID NO: 68 (SynB1/ACT 1)
RGGRLSYSRRRFSTSTGR RPRPDDLEI

SEQ ID NO: 69 (Pep-7/ACT 1)
SDLWEMMMVSLACQY RPRPDDLEI

SEQ ID NO: 70 (HN-1/ACT 1)
TSPLNIHNGQKL RPRPDDLEI

SEQ ID NO: 71 (20 to 120 residues flanking amino acid 363 of human Cx43)
KGKSDPYHATSGALSPAKDCGSQKYAYFNGCSSPTAPLSPMS

PPGYKLVTGDRNNSSCRNYNKQASEQNWANYSAEQNRMGQAG

STISNSHAQPFDFPDDNQNSKKLAAGHELQPLAIVDQR

SEQ ID NO: 72 (20 to 120 residues flanking amino acid 362 of chick Cx43)
KTDPYSHSGTMSPSKDCGSPKYAYYNGCSSPTAPLSPMSPPG

YKLVTGDRNNSSCRNYNKQASEQNWANYSAEQNRMGQAGSTI

SNSHAQPFDFADEHQNTKKLASGHELQPLTIVDQRP

SEQ ID NO: 73 (20 to 120 residues flanking amino acid 377 of human Cx45)
LGFGTIRDSLNSKRRELEDPGAYNYPFTWNTPSAPPGYNIAV

KPDQIQYTELSNAKIAYKQNKANTAQEQQYGSHEENLPADLE

ALQREIRMAQERLDLAVQAYSHQNNPHGPREKKAKV

SEQ ID NO: 74 (20 to 120 residues flanking amino acid 375 of chick Cx45)
GFGTIRDTLNNKRKELEDSGTYNYPFTWNTPSAPPGYNIAVK

PDQMQYTELSNAKMAYKQNKANIAQEQQYGSNEENIPADLEN

LQREIKVAQERLDMAIQAYNNQNNPGSSSREKKSKA.

SEQ ID NO: 75 (20 to 120 residues flanking amino acid 313 of human Cx37)
PYLVDCFVSRPTEKTIFIIFMLVVGLISLVLNLLELVHLLCR

CLSRGMRARQGQDAPPTQGTSSDPYTDQVFFYLPVGQGPSSP

PCPTYNGLSSSEQNWANLTTEERLASSRPPLFLDPP

SEQ ID NO: 76 (20 to 120 residues flanking amino acid 258 of rat Cx33)
CGSKEHGNRKMRGRLLLTYMASIFFKSVFEVAFLLIQWYLYG

FTLSAVYICEQSPCPHRVDCFLSRPTEKTIFILFMLVVSMVS

FVLNVIELFYVLFKAIKNHLGNEKEEVYCNPVELQK.

SEQ ID NO: 77 (enhanced green fluorescent protein)
MVSKGEELFTGVVPILVELDGDVNGHKFSVSGEGEGDATYGK

LTLKFICTTGKLPVPWPTLVTTLTYGVQCFSRYPDHMKQHDF

FKSAMPEGYVQERTIFFKDDGNYKTRAEVKFEGDTLVNRIEL

KGIDFKEDGNILGHKLEYNYNSHNVYIMADKQKNGIKVNFKI

RHNIEDGSVQLADHYQQNTPIGDGPVLLPDNHYLSTQSALSK

DPNEKRDHMVLLEFVTAAGITLGMDELYK

SEQ ID NO: 78 (ACT 2)
CCCTCCTCCCGGGCCTCCTCCCGGGCCTCCTCCCGGCCCCGG

CCCGACGACCTGGAGATC

SEQ ID NO: 79 (ACT 1)
CGGCCCCGGCCCGACGACCTGGAGATC

SEQ ID NO: 80 (ACT 3)
CGGCCCCGGCCCGACGACCTGGAGGTG

SEQ ID NO: 81 (ACT 4)
CGGCCCCGGCCCGACGACGTGCCCGTG

SEQ ID NO: 82 (ACT 5)
AAGGCCCGGTCCGACGACCTGTCCGTG

SEQ ID NO: 83 (Antp)
CGGCAGCCCAAGATCTGGTTCCCCAACCGGCGGAAGCCCTGG

AAG AAG

SEQ ID NO: 84 (Antp/ACT 2)
CGGCAGCCCAAGATCTGGTTCCCCAACCGGCGGAAGCCCTGG

AAGAAGCCCTCCTCCCGGGCCTCCTCCCGGGCCTCCTCCCGG

CCCCGGCCCGACGACCTGGAGATC

SEQ ID NO: 85 (Antp/ACT 1)
CGGCAGCCCAAGATCTGGTTCCCCAACCGGCGGAAGCCCTGG

AAGAAGCGGCCCCGGCCCGACGACCTGGAGATC

SEQ ID NO: 86 (Antp/ACT 3)
CGGCAGCCCAAGATCTGGTTCCCCAACCGGCGGAAGCCCTGG

AAGAAGCGGCCCCGGCCCGACGACCTGGAGGTG

SEQ ID NO: 87 (Antp/ACT 4)
CGGCAGCCCAAGATCTGGTTCCCCAACCGGCGGAAGCCCTGG

AAGAAGCGGCCCCGGCCCGACGACGTGCCCGTG

SEQ ID NO: 88 (Antp/ACT 5)
CGGCAGCCCAAGATCTGGTTCCCCAACCGGCGGAAGCCCTGG

AAGAAGAAGGCCCGGTCCGACGACCTGTCCGTG

SEQ ID NO: 89 (Zebrafish alpha Cx43)
PCSRASSRMSSRARPDDLDV

SEQ ID NO: 90 (Chick alpha Cx36)
PRVSVPNFGRTQSSDSAYV

SEQ ID NO: 91 (Zebrafish alpha Cx36)
PRMSMPNFGRTQSSDSAYV

SEQ ID NO: 92 (Cx43 isoleucine deletion)
RQPKIWFPNRRKPWKKRASSRASSRPRPDDLE

EXAMPLES

Example 1

The objective was to develop a stable, elegant and pourable gel in which the Active Pharmaceutical Ingredient (API) is in solution for wound healing purposes.

The major challenges encountered during formulation development were the selection of suitable stabilizers for the API (ACT1), and other excipients that are non-irritating for wound healing application. Studies were conducted to evaluate prototype formulations.

R&D Study Per Protocol #1062

The first study was conducted per protocol #1062. During this study, 6 prototype formulations were evaluated as outlined in Table 4. The purposes of the study were to select a proper pH range for the product and also to select a proper gelling agent. The API concentration used for this study was 0.072% which was the initial targeted product concentration. Phosphate buffers at pH 5, 6, and 7 and two gelling agents, Pluronic and Hydroxyethylcellulose (HEC) were evaluated. The quantity of API required for the formulations was calculated as follows:

Batch size for each formulation=12×5 g=60 g or 70 g
API quantity for 6 formulations=6×70×0.072%/82.4%=0.37 g
API purity value=82.4%

Five formulations, formulae 2414-10 to -14, were gelled with Pluronic 127, which was assumed to be the preferred gelling agent. Only one formulation, 2414-15, was gelled with HEC as a back-up. The available stability data indicated the following conclusions.

Buffer was needed to control the pH of the gel system and to maintain stability of the peptide drug. Proper pH range seemed to be between 5 and 7. Phosphate buffer was adequate.

Surprisingly, the API, ACT1, was more stable in HEC gel than Pluronic gels. With Pluronic gels, the API dropped to an average of 85% of the label claim (LC) from initial when gels were stored at 5° C. for one month; and to 79% when stored at 25° C. for one month. With HEC gel, the API dropped to 98% of label claim from initial when stored at 5° C. for 3 months and 84% when stored at 25° C. for three months.

HEC appeared to be a better choice of gelling agent than Pluronic when comparing formula 2414-14 to 2414-15. Both formulations were exactly same except that formula 2414-14 was gelled with Pluronic and formula 2414-15 was gelled with HEC. The API in formula 2414-14 dropped to 68% of the label claim from the initial concentration when stored at 5° C. for one month while the API in formula 2414-15 only dropped to 98% of the label claim from the initial concentration when stored at 5° C. for 3 months.

EDTA and Mannitol appear to provide some stability to the peptide drug.

The formulations did not appear to be stable at 25° C. The final product might require refrigeration, which is typical for products containing peptides and proteins.

Formula 2414-15 with HEC as the gelling agent is the most stable formulation compared to the rest of the formulations tested. It was selected for further development. Stability data of formulations 2414-14 and 2414-15 are summarized in Tables 5 and 6, respectively.

TABLE 4

Wound Healing Gel Formulation Compositions for Stability Testing per Study #1062

| Components (% W/W) | Formula #: 2414-10 | Formula #: 2414-11 | Formula #: 2414-12 | Formula #: 2414-13 | Formula #: 2414-14 | Formula #: 2414-15 |
|---|---|---|---|---|---|---|
| API | 0.072 | 0.072 | 0.072 | 0.072 | 0.072 | 0.072 |
| Propylene glycol | 1.0 | 1.0 | 1.0 | 1.0 | 1.0 | 1.0 |
| Glycerin | 5.0 | 5.0 | 5.0 | 5.0 | 5.0 | 5.0 |
| Monobasic Sodium Phosphate | — | 0.300 | 0.263 | 0.120 | 0.263 | 0.263 |
| Dibasic Sodium Phosphate | — | 0.0036 | 0.044 | 0.217 | 0.044 | 0.044 |
| Methylparaben | 0.17 | 0.17 | 0.17 | 0.17 | 0.17 | 0.17 |
| Propylparaben | 0.02 | 0.02 | 0.02 | 0.02 | 0.02 | 0.02 |
| Pluronic 127 (Poloxmer 407) | 20.0 | 20.0 | 20.0 | 20.0 | 20.0 | — |
| EDTA Disodium | — | — | — | — | 0.05 | 0.05 |
| Mannitol | — | — | — | — | 0.05 | 0.05 |
| Hydroxyethylcellulose 250HHX | — | — | — | — | — | 1.25 |
| Purified water | q.s. 100 No Buffer | q.s. 100 Buffer pH 5 | q.s. 100 Buffer pH 6 | q.s. 100 Buffer pH 7 | q.s. 100 Buffer pH 6 | q.s. 100 Buffer pH 6 |

TABLE 5

Stability Results of Formula 2414-14 Containing Pluronic 127 per Study #1062

| Storage Condition | Time Point (Month) | Physical Properties and Appearance | Chemical Assay (%, LC) API | Methyl-paraben | Propyl-paraben |
|---|---|---|---|---|---|
| | Initial | Clear and colorless gel | 98.8 | 92.0 | 96.6 |
| Freeze/Thaw | | Conforms | 89.8 | 88.6 | 94.0 |
| 5° C. | 1 | Conforms | 84.6 | 93.0 | 97.9 |
| 25° C. | ½ | Conforms | 90.6 | 93.6 | 98.6 |
| | 1 | Conforms | 82.8 | 88.8 | 94.0 |

TABLE 6

Stability Results of Formula 2414-15 Containing HEC per Study #1062

| Storage Condition | Time Point (Month) | Physical Properties and Appearance | Chemical Assay (%, LC) | | |
|---|---|---|---|---|---|
| | | | API | Methyl-paraben | Propyl-paraben |
| | Initial | Clear colorless gel | 101.9 | 97 | 103.1 |
| Freeze/Thaw | | Conforms | 98.8 | 97.1 | 103.9 |
| 5° C. | 1 | Conforms | 96 | 98.1 | 104.6 |
| | 3 | Conforms | 99.7 | 98.3 | 101.8 |
| 25° C. | ½ | Conforms | 91.6 | 99.7 | 106.7 |
| | 1 | Conforms | 93.4 | 96.8 | 103 |
| | 3 | Conforms | 85.7 | 92.8 | 96.5 |

Example 2

R&D Study Per Protocol #1074

Based on the results from study #1062, additional prototype formulations based on formula 2414-15 were designed and evaluated per protocol #1074. During this study, 7 prototype formulations were prepared. The purposes of the study were to select a proper buffering system and antioxidants for the formulation. Five (5) antioxidants were evaluated: Mannitol, Methionine, Acetylcysteine, Lysine and Histidine. Two buffer systems were used: phosphate buffer at pH 6 and citrate buffer at pH 5. Glycerin (5%) was introduced into the new prototype formulations to provide some humectant property to the wound treatment topical gel. PEG 200 was also evaluated for its potential stabilizer effect. The compositions of the prototypes evaluated per study #1074 are listed in Table 7.

Due to API availability limitations, 0.036% of API concentration was used for this study. Formula 2414-18 is identical to 2414-15 except that the API concentration was reduced from 0.072% to 0.036%. The available stability data from study #1074 found in Table 8 indicated the following conclusions.

Phosphate buffer seemed to provide better stability to the peptide when compared to the citrate buffer. The buffer capacity at 25 mM is adequate for the system.

Mannitol seemed to provide adequate stability to the peptide.

The effect of other antioxidants was not clear due to the variability in the chemical data.

Based on the study results mainly from study #1062 and partially from #1074, a final formulation was selected for further development. The final formulation contained 25 mM phosphate buffer to maintain the pH of the formulation, mannitol as a stabilizer for the API, and HEC as a gelling agent. The amount of propylene glycol was increased from 1% to 3% in prototype formulations to allow for better solubilization of the parabens in the aqueous system. Four potential API concentrations were selected: 0.0072%, 0.018%, 0.036% and 0.072%. The final formula is summarized in Table 9. The stability of the final selected formula containing different levels of API was also evaluated with analytical methods. In addition, the overall stability was assessed by visual inspection for white powder or precipitate and determination of water content.

TABLE 7

Composition of Prototype Formulations per Study #1074

| Component (% w/w) | Formula # 2414- | | | | | | |
|---|---|---|---|---|---|---|---|
| | 18 | 19 | 20 | 21 | 22 | 23 | 26 |
| Peptide 328967 (ACT1) | 0.036 | 0.036 | 0.036 | 0.036 | 0.036 | 0.036 | 0.036 |
| Propylene Glycol | 1.0 | 1.0 | 1.0 | 1.0 | 1.0 | — | — |
| PEG 200 | — | — | — | — | — | 5.0 | 5.0 |
| Glycerin | 5.0 | 5.0 | 5.0 | 5.0 | 5.0 | 5.0 | 5.0 |
| Monobasic Sodium Phosphate | 0.263 | 0.263 | 0.263 | 0.263 | 0.526 | — | — |
| Dibasic Sodium Phosphate | 0.044 | 0.044 | 0.044 | 0.044 | 0.088 | — | — |
| Citric Acid, anhydrous | — | — | — | — | — | 0.60 | 0.60 |
| Sodium Citrate, anhydrous | — | — | — | — | — | 1.73 | 1.73 |
| Methylparaben | 0.17 | 0.17 | 0.17 | 0.17 | 0.17 | 0.17 | 0.17 |
| Propylparaben | 0.02 | 0.02 | 0.02 | 0.02 | 0.02 | 0.02 | 0.02 |
| EDTA disodium | 0.05 | 0.05 | 0.05 | 0.05 | 0.05 | 0.05 | 0.05 |
| Mannitol | 0.05 | — | — | — | — | 0.05 | — |
| Methionine | — | 0.5 | 0.5 | 0.5 | 0.5 | — | — |
| Acetylcysteine | — | — | — | — | 0.2 | — | — |
| Lysine | — | — | 0.1 | — | — | — | 0.1 |
| Histidine | — | — | — | 0.1 | — | — | — |
| Hydroxyethylcellulose 250 HHX | 1.25 | 1.25 | 1.25 | 1.25 | 1.25 | 1.25 | 1.25 |
| Purified Water, qsad | 100 | 100 | 100 | 100 | 100 | 100 | 100 |
| | 25 mM Buffer pH 6 | 25 mM Buffer pH 6 | 25 mM Buffer pH 6 | 25 mM Buffer pH 6 | 50 mM Buffer pH 6 | 100 mM Buffer pH 5 | 100 mM Buffer pH 5 |

TABLE 8

Stability Results of Formulas 2414-18, 2414-19, 2414-20, 2414-21, 2414-22, 2414-23, and 2414-26 from Study #1074

| Sample | Storage Condition | Time Point (Month) | Physical Properties Appearance | API | Methyl-paraben | Propyl-paraben |
|---|---|---|---|---|---|---|
| Formula 2414-18 | | Initial | Clear and Colorless Gel | 106.4 | 94.6 | 102.2 |
| | 5° C. | 1 | Conforms | 90.1 | 83.4 | 88.2 |
| | | 2 | Conforms | NA | NA | NA |
| | | 3 | Conforms[1] | NA | NA | NA |
| | 25° C. | 1 | Conforms | 94.3 | 90.4 | 95.5 |
| | | 2 | Conforms | NA | NA | NA |
| | | 3 | Conforms[1] | NA | NA | NA |
| Formula 2414-19 | | Initial | Clear and Colorless Gel | 109.3 | 94.2 | 119.7 |
| | 5° C. | 1 | Conforms | 101.1 | 90.4 | 112.6 |
| | | 2 | Conforms | NA | NA | NA |
| | | 3 | Conforms[1] | NA | NA | NA |
| | 25° C. | 1 | Conforms | 103.3 | 94.6 | 117.4 |
| | | 2 | Conforms | NA | NA | NA |
| | | 3 | Conforms[1] | NA | NA | NA |
| Formula 2414-20 | | Initial | Clear and Colorless Gel | 107.0 | 96.9 | 99.9 |
| | 5° C. | 1 | Conforms | 106.8 | 96.7 | 98.4 |
| | | 2 | Conforms | NA | NA | NA |
| | | 3 | Conforms[1] | NA | NA | NA |
| | 25° C. | 1 | Conforms | 97.9 | 94.2 | 95.6 |
| | | 2 | Conforms | NA | NA | NA |
| | | 3 | Conforms[1] | NA | NA | NA |
| Formula 2414-21 | | Initial | Clear and Colorless Gel | 104.3 | 95.1 | 110.4 |
| | 5° C. | 1 | Conforms | 96.7 | 91.5 | 104.2 |
| | | 2 | Conforms | NA | NA | NA |
| | | 3 | Conforms[1] | NA | NA | NA |
| | 25° C. | 1 | Conforms | 96.4 | 95.0 | 108.4 |
| | | 2 | Conforms | NA | NA | NA |
| | | 3 | Conforms[1] | NA | NA | NA |
| Formula 2414-22 | | Initial | Clear and Colorless Gel | 112.2 | 96.1 | 109.4 |
| | 5° C. | 1 | Conforms | 111.4 | 94.9 | 106.1 |
| | | 2 | Conforms | NA | NA | NA |
| | | 3 | Conforms[1] | NA | NA | NA |
| | 25° C. | 1 | Conforms | 96.5 | 89.5 | 100.0 |
| | | 2 | Conforms | NA | NA | NA |
| | | 3 | Conforms[1] | NA | NA | NA |
| Formula 2414-23 | | Initial | Clear and Colorless Gel | 87.8 | 94.7 | 101.6 |
| | 5° C. | 1 | Conforms | 88.3 | 92.9 | 97.0 |
| | | 2 | Conforms | NA | NA | NA |
| | | 3 | Conforms[1] | NA | NA | NA |
| | 25° C. | 1 | Conforms | 74.4 | 84.4 | 88.4 |
| | | 2 | Conforms | NA | NA | NA |
| | | 3 | Conforms[1] | NA | NA | NA |
| Formula 2414-26 | | Initial | Clear and Colorless Gel | 83.0 | 95.5 | 105.9 |
| | 5° C. | 1 | Conforms | 78.5 | 91.0 | 98.5 |
| | | 2 | Conforms | NA | NA | NA |
| | | 3 | Conforms[1] | NA | NA | NA |
| | 25° C. | 1 | Conforms | 77.4 | 93.3 | 100.7 |
| | | 2 | Conforms | NA | NA | NA |
| | | 3 | Conforms[1] | NA | NA | NA |

[1]Particles at the bottom of vial;
NA = data not available

In one embodiment, a batch of the drug product may be prepared by following the steps of the manufacturing process flow chart and using the composition of Table 9.

Example 3 Treatment of Diabetic Foot Ulcer

A Phase II, randomized, prospective, double blind, parallel group, multi-center study was conducted to assess the safety and efficacy of ACT1 peptide in the treatment of diabetic foot ulcer.

Subjects in Group A received 10 µM of the ACT peptide formulation (i.e., Granexin™ Gel) in addition to standard-of-care treatment (SoC) compared to SoC alone in Group B. The total study duration for efficacy assessments was 12 weeks with additional 12 weeks follow up for safety evaluations. The study procedures were divided into three phases: Screening Procedures (Study Days: −7 and 0), Treatment Procedures (Study Day 0 through Study Week 12), and Follow-up Procedures (Study Months 4 through 6).

Subjects enrolled in the study may have had multiple ulcers but only one ulcer was considered as the target ulcer which was within the range of 4-1250 mm² and was separated from other ulcers by at least 20 mm. According to the randomization schedule, subjects had their ulcer site treated with either Granexin™ Gel and SoC or SoC alone. Each subject in Group A was treated with up to 14 applications of Granexin™ Gel over the initial 12 weeks of the study period. Other than the application of Granexin™ Gel, management of the wound sites was equivalent in both the groups. Each subject was assessed weekly for the first 12 weeks of treatment. Statistical analysis of subject data up to 12 weeks was done for efficacy and safety analyses. Wound photographs were used to assess wound closure for both control and test sites. Safety was determined by Treatment Emergent Adverse Events (TEAEs).

Inclusion Criteria:
A subject was enrolled in this study if he/she met the following criteria:
1. Male or female aged 18 years and older
2a. Female subjects were post-menopausal or surgically sterilized, or
2b. Female of child-bearing potential must have had a negative pregnancy test at Screening, and agreed to use hormonal contraceptive or intra-uterine device or diaphragm with spermicide or condom with spermicide or abstinence throughout the study
3. Diabetes mellitus (type I or II) with an HbA1c<10.0%
4. Diagnosis of neuropathic foot ulcer
5. Cutaneous, full thickness (University of Texas grade A1), below ankle surface ulcer between 0.5 cm² and 40 cm² post debridement
6. A viable, granulating wound as per Investigator's discretion
7. Ulcer present for at least 4 weeks prior to Screening
8. An Ankle Brachial Pressure Index (ABPI) between 0.70 and 1.3 measured at Screening
9. Signed informed consent form Exclusion Criteria:
1. A subject was not eligible for this study if he/she met any of the following criteria:
2. Decrease or increase in the ulcer size by 30% or more during 7 day screening period
3. Cannot tolerate the off-loading method or comply with SoC
4. An ulcer which showed signs of severe clinical infection, defined as pus oozing from the ulcer site
5. The ulcer to be treated required operative debridement
6. An ulcer positive for β-hemolytic streptococcus upon culture
7. Requirement for total contact casts 8. The ulcer had more than 50% slough, significant necrotic tissue, bone, tendon, or capsule exposure
9. Highly exuding wounds (wounds that require a daily dressing change)ABPI<0.7 or >1.3 or ankle systolic pressure <70 mm H
10. gHad systemic infections
11. Met one of the following (only 1 out of 3 tests was required):
   a. Doppler waveform analysis on the dorsalis pedis and posterior tibial arteries a monophasic or biphasic flow (with loss of reverse flow) in either foot artery, or
   b. A toe: brachial index <0.7 or >1.3, or
   c. Transcutaneous oxygen pressure <40 mm Hg
12. Presence of an active systemic or local cancer or tumor of any kind (with the exception of non-melanoma skin cancer)
13. Congestive Heart Failure New York Heart Association class II-IV or coronary heart disease with ST segment elevation myocardial infarction or coronary artery bypass graft or percutaneous transluminal coronary angioplasty within the last 6 months
14. Active osteomyelitis of the study foot
15. Active connective tissue disease
16. Acute Charcot's neuro-arthropathy as determined by clinical and/or radiographic examination
17. Active treatment with systemic corticosteroids
18. Previous or current radiation therapy to the distal lower extremity or likelihood to receive this therapy during study participation
19. Pregnant or nursing subjects
20. Uncontrolled anemia (Hb<10 g/dL in females and <12 g/dL in males)
21. Estimated glomerular filtration rate <25 mL/min
22. Poor nutritional status defined as an albumin <25 g/L
23. Significant peripheral edema as per Investigator's discretion
24. Known prior inability or unavailability to complete required study visits during study participation
25. A psychiatric condition (e.g. suicidal ideation) or chronic alcohol or drug abuse problem, determined from the subject's medical history, which, in the opinion of the Investigator, may pose a threat to subject compliance
26. Use of a platelet-derived growth factor within 28 days prior to Screening
27. Use of any investigational drug or therapy within 28 days prior to Screening
28. Any other factor which may have, in the opinion of the Investigator, compromised participation and follow-up in this study Granexin™ Gel (100 µM ACT1 peptide, in the formulation described in Table 1 of this application) was applied topically on the wound on Day 0, Day 3, Week 1, 2, 3, 4, 5, 6, 7, 8, 9, 10, 11, and 12.

Total duration of the study was 12 months, including 6 months enrollment period. Individual subject participation for the period of interim analysis was approximately 12 weeks.

Efficacy:
Efficacy was evaluated by assessment of the following parameters between study Day 0 to Week 12:
  Wound photographs*
  Wound tracings**
  Wound closure assessment*
  Wound characteristics (clinical assessment)**
  Wound treatment response**

Safety:
The safety was evaluated by assessing the following parameters:
  TEAEs (each visit from Day 0 up to Week 12)*
  Vitals (Day −7 and Week 12 or Last Subject Last Visit [LSLV])**
  Laboratory assessments (Day −7 and Week 12 or LSLV)**
  * These evaluations were considered for the interim analysis
  ** These evaluations were not considered for the interim analysis Sample Size Calculations The sample size was calculated with reference to the primary endpoint (comparing the reduction in wound size as measured by the mean percentage decrease from Baseline to the last visit). Assuming a 25% difference in favor of subjects treated with Granexin™ Gel, power of 80%, significance level of 95% (two-sided) and Standard Deviation (SD) of 40%, 40 subjects were calculated to be required in each treatment group. Adjusting for 15% dropout rate, 92 subjects were required to be enrolled in the study.

All statistical tests were carried out as two-sided on 5% level of significance unless otherwise stated. Summary tables and descriptive statistics were done for demographics, efficacy, and safety variables. To adjust the main efficacy analyses for measured covariates at Baseline, Analysis of Co-Variance (ANCOVA) and survival analysis were performed. The descriptive statistics for continuous variables were presented with number (N) of non-missing observations, mean, SD, median, minimum and maximum or range. For categorical data, descriptive statistics were presented with number of exposed subjects and number (N) with percentage of observations in the various categories of the endpoint, where percentage was based on the exposed subjects.

Primary efficacy analysis was performed on Intent-to-Treat (ITT) and Per Protocol (PP) populations. Primary efficacy data was calculated using sample number (n), mean, SD, median, minimum, maximum, and 95% Confidence Interval (CI).

ANCOVA with repeated measures was performed for comparison of mean percent reduction of wound area from Baseline compared to Week 12 between the two treatment groups. Mean percent reduction of wound area from Baseline to Week 12 was considered as response variable adjusted for the strata, wound duration, viable tissue, exudate level, and the Body Mass Index (BMI) as covariates and treatment group, treatment by visit interaction, and visit as factor included in ANCOVA model.

The mean percent wound closure at 4 weeks compared to Baseline was analyzed as described in the primary efficacy analysis. Subject assessment of intensity of pain at Week 12 was analyzed by the Wilcoxon Mann-Whitney U test.

For time-to-event endpoints, the distribution for each treatment group was estimated by the Kaplan-Meier method and compared by the log-rank test. The median time along with 90% confidence limits was presented for each treatment group. Simultaneous confidence bounds for the Kaplan-Meier curve were computed for both the treatment groups. Further, Cox proportional hazard regression model analysis was conducted to compare the event-time distribution function between the treatment groups. The incidence of 100% study wound closure was a time-to-event analysis computed using Kaplan-Meier methods where all scheduled visits from Day 0 though Week 12 were included in the analysis. This was the primary analysis of the secondary efficacy endpoint. Summary statistics, including the median for incidence of 100% study wound closure was presented. The statistical significance of the difference in the incidence of 100% wound closure was evaluated using the log-rank test. Cox's proportional hazard regression analysis was performed to evaluate the individual and joint effects of several covariates on the incidence of 100% wound closure.

Incidence of 100% wound closure (closed or not closed) by or on Week 12 was analyzed overall and by center. Statistical significance in frequency between treatment groups were assessed by Fisher's Exact test (two-tailed) to determine the overall wound healing frequencies. This was followed by the Cochran-Mantel-Haenszel test which compared the 2 treatment groups with respect to the incidence of 100% wound closure after adjusting for pooled center. The Breslow-Day test was used in conjunction with the Cochran-Mantel-Haenszel test to determine the statistical significance of a treatment by-pooled-center interaction Results Mean Percent Wound Closure from Baseline to Week 12

The primary efficacy endpoint of the study was to evaluate mean percent wound closure from Baseline to Week 12. The non-parametric Wilcoxon Mann-Whitney U test was used to analyze mean percent reduction of wound area from Baseline to Week 12 in both the treatment groups since the data did not follow a normal distribution, as confirmed by a Shapiro-Wilk p-value of <0.0001 and a non-linear Q-Q plot. The addition of the ranks of both groups obtained after sorting the data of wound size reduction in ascending order in the PP population showed that the actual sum of scores (1036.00) was higher in Group A subjects than the expected sum of scores i.e. sum of scores when there is no difference in 2 groups, under the null hypothesis (899.00) and in Group B, the actual sum of scores (617.00) was found to be lower than the expected sum of the scores under the null hypothesis (754.00). Therefore, in the PP population, subjects treated with Granexin™ Gel plus SoC (Group A) had a higher percent wound closure from Baseline to Week 12 compared to subjects treated with SoC alone (Group B), which was statistically significantly (p-value=0.0069).

Mean Percent Wound Closure from Baseline to Week 4

Similarly non-parametric analysis for secondary endpoint showed that in the PP population, the mean percent reduction of wound area from Baseline to Week 4 was statistically significantly higher in Group A as compared to Group B (p-value=0.0128).

Subject Self Assessment of Change in Intensity of Pain from Baseline to Week 12

The intensity of pain experienced by the subjects was recorded on a Visual Analogue Scale of 1 to 10 where 1 indicated "no pain" and 10 indicated "extreme pain". The intensity of pain as assessed by the subjects of the PP population at treatment Week 12 of the study showed using the Wilcoxon Mann-Whitney U test that there was no statistically significant difference in subject self assessment of intensity of pain at Week 12 between the 2 treatment groups (Group A, 0.4±1.22; Group B, 0.3±0.81; p-value=0.9683).

Time-to-Wound Closure Analysis

The time taken for complete wound closure in the PP population was statistically significantly lower in subjects in Group A as compared to subjects in Group B (p-value=0.0057). Of the 32 subjects in Group A, 81.3% subjects had complete (100%) wound closure and 18.8% subjects who did not, were censored. The median duration of 100% wound closure in Group A was 6 weeks. Of the 28 subjects in Group B, 53.6% subjects had complete wound closure and 46.4% subjects not having 100% wound closure, were censored and the median duration of time to complete 100% wound closure was 14.64 weeks.

The time taken to achieve 50% wound closure by Week 12 in the PP population was not statistically significantly lower in subjects in Group A as compared to the time taken by subjects in Group B (p-value=0.2084). The analysis of time taken for complete 50% wound closure by Week 12 showed that of the 32 subjects in Group A, 93.8% subjects completed 50% wound closure and 6.3% subjects did not complete 50% wound closure and were censored. In comparison to that, out of 28 subjects in Group B, 89.3% subjects had 50% wound closure and 10.7% subjects without at least 50% wound closure during the study period were censored. The median duration of 50% wound closure was 2 weeks in Group A and 4.07 weeks in Group B.

Cox Proportional Hazard Regression Analysis for time to 100% wound closure in the PP population showed that though treatment was not a statistically significant factor affecting the wound closure (p-value=0.0856), the subjects in Group A treated with Granexin™ Gel plus SoC would have wound closure 2.339 times more than the subjects in Group B treated with SoC only. Similarly, baseline wound depth and BMI were not statistically significant factors (baseline wound depth: p-value=0.4554, BM: p-value=0.4435) but would affect wound closure by 1.715 times and 1.050 times, respectively. All other parameters, including wound size, wound duration, and use of dressings did not have a statistically significant effect on the rate of wound closure for both the treatments.

Incidence of 100% Wound Closure by or on Week 12

The categorical analysis of incidence of 100% and 50% wound closure by or on Week 12 in the PP population was done using the Cochran-Mantel-Haenszel analysis with Breslow-Day test and the Chi-square test. The Chi-square test performed by combining the data from all the study centers showed that there were statistically significantly higher number of responders in Group A than in Group B (100% wound closure: p-value=0.0104; 50% wound closure: p-value=0.0063). Therefore it can be concluded that the frequency of 100% and 50% epithelialization occurred at a higher frequency in wounds of subjects treated with Granexin™ Gel than subjects treated with SoC only.

Safety:

Overall, 21 subjects reported 26 AEs of which 18 (69.2%) AEs were mild in intensity. A total of 4 moderate and 4 severe AEs were reported in this study. In Group A, death and foot fracture were the severe AEs and myocardial infarction and inadequate control of diabetes mellitus were severe AEs reported in Group B. None of the AEs reported in this study were considered probably or possibly related to Granexin™ Gel or the SoC treatment. Of the 26 events, 18 (69.2%) recovered and 3 (11.5%) events recovered with sequelae. No action was taken against 22 AEs. None of the subjects withdrew due to an AE. Five subjects reported 5 Serious Adverse Events (SAEs). In Group A, 1 death was reported due to an unknown cause and 1 death in Group B occurred due to myocardial infarction. None of the SAEs, including the deaths, were related to Granexin™ Gel.

This phase II study was a double blind, randomized, prospective, parallel group, multi-center study conducted at 8 centers in India to evaluate the efficacy and safety of Granexin™ Gel in the treatment of DFU. The total duration of the study was 12 months, including 6 months enrollment period and 6 months for study procedures (3 months each for efficacy and safety analyses). Hence, the study duration for an individual subject was approximately 6 months, including 18 visits. For interim analysis, data up to 12 weeks (Visit 15) was considered. A total of 92 subjects were randomized in the study to receive Granexin™ Gel plus SoC or only SoC in the treatment of DFU. Of these subjects, 76 (82.6%) completed the study treatment visits up to Visit 15 and are now in the follow-up stage of the study.

The primary efficacy endpoint of the study was to evaluate mean percent wound reduction from Baseline to Week 12. The non-parametric Wilcoxon Mann-Whitney U test was used to analyze mean percent reduction of wound area from Baseline to Week 12. In the PP population, subjects treated with Granexin™ Gel plus SoC (Group A) showed statistically significantly higher percent wound closure from Baseline to Week 12 compared to subjects treated with SoC alone (Group B) (p-value=0.0069), suggesting that at Week 12 wounds treated with Granexin™ Gel plus SoC healed better than the wounds treated with SoC alone.

The secondary endpoints of the study were to assess mean percent wound closure at Week 4, subject assessment of pain, and time to complete wound closure. At Week 4, Group A subjects in the PP population showed statistically significantly higher percent reduction of wound area from Baseline compared to Group B subjects in the PP population. There was no statistically significant difference in intensity of pain as assessed by the subject from Baseline to Week 12 between the 2 treatment groups. Hence, Granexin™ Gel did not affect the intensity of pain experienced by the subjects as recorded on a Visual Analogue Scale of 1 to 10.

Complete wound closure was defined as 100% epithelialization of the wound and the absence of drainage from the wound. In the PP population, subjects in Group A took significantly less time to achieve 100% wound closure than those in Group B. However, the time taken for 50% wound closure was not significantly lower in Group A as compared to Group B. The categorical analysis of incidence of 100% and 50% wound closure at Week 12 was conducted and the subjects who had 100% wound closure were considered as responders. The number of responders in Group A was significantly higher than in Group B, indicating that the wounds treated with Granexin™ Gel plus SoC have higher incidences of 100% and 50% epithelialization than wounds treated with SoC alone.

Cox Proportional Hazard Regression Model was used to compare the event-time distribution function between the treatment groups. Although treatment was not a significant factor affecting time to 100% wound closure, in the PP population Group A subjects demonstrated 2.3 times higher wound closure than Group B subjects. In addition, baseline wound depth and BMI were not significant factors but affected wound closure by 1.715 times and 1.050 times, respectively. All other parameters, including wound size, wound duration, and use of dressings did not have a statistically significant difference in affecting wound closure for both the treatments. Cox Proportional Hazard Regression Analysis for time to 50% wound closure showed that none of the covariates (treatment group, wound size, wound duration, baseline wound depth, and BMI) were significantly associated with time to 50% wound closure. However, Group A subjects had wound closure 1.186 times more than Group B subjects.

In terms of safety, out of 92 subjects, 21 (22.8%) subjects reported 26 AEs. There was no significant difference in the number of subjects with at least 1 AE between the 2 treatment groups (Group A, 11; Group B, 10; p-value=0.8038). A total of 4 AEs were of severe intensity. None of the AEs were related to the Granexin™ Gel or SoC. None of the subjects withdrew due to an AE. A total 5 (5.4%) subjects reported 5 SAEs where 2 SAEs were observed in Group A subjects and 3 SAEs were in Group B subjects. In Group A, 1 death was reported due to an unknown cause and 1 death in Group B occurred due to myocardial infarction. None of the SAEs were related to Granexin™ Gel or SoC.

In conclusion, Granexin™ Gel along with SoC has shown to accelerate wound healing in subjects with DFU, making it an efficacious, safe, and well tolerated therapeutic option for the treatment of DFU.

The description of 18 visits along with premature study discontinuation and unscheduled visits is summarized below:

Visit 1: Screening (Day −7)

The Screening Visit was held a maximum of 7 days prior to the Baseline Visit. The following procedures were performed at the Screening Visit:

Screening Procedures: informed consent, medical history, physical examination including neuro-vascular examination, vitals, ulcer identification and history, assessment of wound infection, X-rays, Electrocardiogram (ECG), and serum pregnancy test Inclusion and exclusion criteria checked Laboratory tests Immunology tests Photography of the ulcer Wound debridement Wound tracing Wound bed preparation Recorded the use of concomitant medication Recorded the presence of concomitant illness(es)

Visit 2: Baseline (Day 0)

The Baseline Visit was held a maximum of 7 days after Screening. If ulcers healed by >30% within 7 days of the start of the study at Day 0, then the subject was not eligible for participation in the study. The following procedures were performed at Baseline:

Inclusion and exclusion criteria checked to confirm that no change had occurred since Screening Randomization Photography of the ulcer Wound tracing Clinical assessment Compliance checked Wound closure assessment Wound bed preparation Treatment with Granexin™ Gel (if applicable)

Dressing changed

Pain assessment

Recorded changes in concomitant medication

Recorded Adverse Events (AEs), if any

Visit 3-14: Treatment Visits (Day 3 through Week 11)

On Treatment Visits were conducted at Day 3 followed by Week 1, 2, 3, 4, 5, 6, 7, 8, 9, 10, and 11 after Baseline Visit 1 day. The following procedures were performed at these visits:

Photography of the ulcer

Wound tracing

Clinical assessment

Compliance checked

Wound closure assessment

Wound bed preparation

Treatment with Granexin™ Gel (if applicable)

Dressing changed

Pain assessment

Recorded changes in concomitant medication
Recorded AEs, if any
Visit 15: End of Treatment Visit (Week 12)
The End of Treatment Visit was conducted at Visit 15 (Week 12±1 day). The following procedures were performed at this visit:
Laboratory tests
Immunology tests
Photography of the ulcer
Wound tracing
Clinical assessment
Compliance checked
Wound closure assessment
Wound bed preparation
Treatment with Granexin™ Gel (if applicable)
Dressing changed
Pain assessment
Recorded changes in concomitant medication
Additional end of treatment visit evaluations (assessment of ulcer response to treatment, comparison of current treatment to previous treatment, incidence of ulcer recurrence within the 12-week treatment period, and vital signs)
Recorded AEs, if any
Visit 16-18: Follow-up Visits, including End of Study Visit (Month 4 through 6)
The Follow-up visits would be conducted at Month 4±3 days, Month 5±3 days, and Month 6±3 days (End of Study [EOS] visit) The following procedures would be performed at these visits:
Photography of the ulcer
Pain assessment
Recorded changes in concomitant medication
Follow-up procedures (evaluation of ulcer recurrence, care of unhealed ulcers, assessment of healed wounds, and subject assessment of pain)
Recorded AEs, if any
EOS procedures (only at Visit 18)

Granexin™ Gel is a topical hydrogel that contains the active ingredient ACT1 peptide (100 μM). Granexin™ Gel has greater than 90% water, which provides a barrier to infection or external elements while maintaining a moist environment for the wound. In Group A, the ulcer was cleansed with sterile saline and if any bleeding existed, it was stopped before applying the Granexin™ Gel on Days 0 and 3, and Weeks 1, 2, 3, 4, 5, 6, 7, 8, 9, 10, 11, and 12. The Granexin™ Gel was dispensed directly from its 5 ml glass vial(s) to completely cover the wound bed. With a clean sterile cotton swab, sterile tongue depressor, or similar application aid, the Granexin™ Gel was evenly spread over the wound surface. The treatment site was then dressed according to the following regimen:
Used adequate off-loading other than TCC as per the Investigator's judgment
Applied a non-adherent dressing over the ulcer and Granexin™ Gel which extended 0.5 inch beyond the ulcer perimeter and inflamed skin margins
Applied a non-occlusive dressing such as fine mesh gauze which was either folded or rolled as a bolster
Standard of Care (Control) Treatment
In the control group, the ulcer was cleansed with sterile saline and if any bleeding existed, it was stopped before dressing. The ulcer was dressed according to the following regimen:
Used adequate off-loading other than TCC as per the Investigator's judgment
Applied a non-adherent dressing such as the 4 layer dressing over the ulcer with either soframycin, Lyseal ointment or hydroheal AM gel which extended 0.5 inch beyond the ulcer perimeter and inflamed skin margins
Applied a non-occlusive dressing such as pressure bandage or fine mesh gauze which was either folded or rolled as a bolster Granexin™ Gel is a topical gel with the active drug substance ACT1 peptide developed at FirstString Research for the management of wounds. ACT1 is a synthetic peptide (25 amino acid) designed to mimic the Carboxy (C)-terminus of the ubiquitous transmembrane gap junction protein Connexin 43 (Cx43), with high binding specificity to zona occludens, a cytoplasmic tight junction protein. While the mechanism of action of ACT1 has not been completely elucidated, the peptide is soluble and engineered to directly translocate within cells. ACT1 peptide interacts with a known binding partner of Cx43—the Postsynaptic Density 95/Discs Large/Zonula Occludens (PDZ)-2 domain of Zonula Occludens-1 (ZO-1). The binding of the peptide to specific Cx43 C-terminus interaction domains such as PDZ-2 on ZO-1 serves to competitively inhibit its association with the Cx43 C-terminus. Connexins are gap junction proteins where as ZO-1 is a tight junction associated protein. The binding of the 25 amino acid ACT1 peptide to the PDZ-2 domain of ZO-1 serves to stabilize gap junctions as well as tight junctions. This junctional stability has been associated with faster healing and reduced scarring. In addition, the low molecular weight (25 amino acid) peptide is expected to reduce the risk of an immunogenic response.

Granexin™ Gel is also designed to provide a localized protective barrier against microbial colonization and a moist environment to promote natural autolytic debridement of necrotic tissue surrounding the wound. The lot number of Granexin™ Gel used in this study was DP 1493.

Subjects were randomized 1:1 to either Group A (Granexin™ Gel plus SoC) or Group B (SoC only). Interactive Web Response System (IWRS) was used for randomization of the eligible subjects to the treatment group. The randomization was further stratified by wound size (<10 cm$^2$ and >10 cm$^2$) to avoid bias of undue number of subjects with small or large wounds going into one arm of the study. The subject ID, initials and study Day 0 date were written on the randomization code sheet and filed with the subject's CRF. Randomization lists were prepared centrally by the MNI data management center using a validated computer program (Statistical Analysis Software [SAS] 9.1.3).

Two studies, including a preclinical and clinical study tested the efficacy and safety of 100 μM concentration of ACT1 formulated in Granexin™ Gel. In the preclinical study, the efficacy of Granexin™ Gel in wound healing was assessed on 5 mm diameter full thickness excisional wounds in adult mice and pigs. Wounds treated with 10 μM of ACT1 peptide closed faster, appeared less swollen and inflamed, and healed with a smoother and less discolored appearance as compared to the wounds applied with the vehicle control [18]. Subsequently, a phase I, double blind, single-center, controlled study was conducted to evaluate the safety and tolerability of 20, 50, 100, and 20 μM concentrations of ACT1 formulated in Granexin™ Gel versus placebo in 48 healthy subjects following punch biopsy. The results showed the Granexin™ Gel (ACT1) at each concentration to be safe and well tolerated with no evidence of localized or systemic AEs or Serious Adverse Events (SAEs). Both preclinical and clinical studies concluded 100 μM concentration of the ACT1 peptide to be optimum in safety and effectiveness.

Hence, the dose of 100 μM ACT1 of Granexin™ Gel was selected in the treatment of DFU in this study.

For each subject, Granexin™ Gel (100 μM ACT1) was applied at Days 0 and 3, and Weeks 1, 2, 3, 4, 5, 6, 7, 8, 9, 10, 11, and 12

Efficacy and Safety Variables: The primary efficacy variable was mean percent wound closure from Baseline to Week 12

Secondary Efficacy Variables

Mean percent wound closure at 4 weeks

Subject self-assessment of intensity of pain (till Week 12)

Time to 50% wound closure

Time to complete wound closure with 100% epithelialization of the wound

Safety Variable: The safety variable was incidence of treatment related Adverse Events (AEs) (till Week 12).

An AE was defined as "any untoward medical occurrence in a subject or clinical investigation subject administered a pharmaceutical product that did not necessarily have a causal relationship with this treatment" (ICH E6:1.2). An AE, therefore, was any unfavorable and unintended sign, symptom, or disease temporally associated with the use of a medicinal product, whether or not considered related to the medicinal product.

A clinically significant abnormal laboratory finding was also regarded as an AE and it was the responsibility of the Investigator to review the laboratory test results and determine whether an abnormal laboratory value was of clinical significance. In general, clinically significant laboratory values which suggested disease progression and/or required active management were considered as AEs.

Worsening of a pre-existing medical condition (e.g. diabetes, migraine, headaches, and gout) was considered as an AE if there was either an increase in severity, frequency, duration of the condition, or an association with significantly worse outcomes. Pre-planned procedures and pre-existing conditions that did not worsen were not considered AEs.

A Serious Adverse Event (SAE) was defined as an AE that:

Was fatal

Was life threatening (places the subject at immediate risk of death)

Required in-subject hospitalization or prolongation of existing hospitalization

Resulted in persistent or significant disability/incapacity

Was a congenital anomaly/birth defect

Met other significant medical hazard

An AE necessitating hospitalization met the regulatory definition for "serious" if the in-subject hospital admission included a minimum of an overnight stay in a health care facility. Any AE that did not meet one of the definitions of serious (e.g. an AE requiring an emergency room visit, out-subject surgery, or requiring urgent investigation) was considered by the Investigator to meet the "other significant medical hazard" criterion for classification as an SAE.

If the above interventions were performed as SoC and not associated with an AE, the health issue for which the intervention was performed was not considered as an SAE. If there was a complication as a result of the procedure and the complication met at least 1 seriousness criterion, then that complication was reported as an SAE.

Study Subjects: A total of 98 subjects with DFU were screened. Of these, 6 were screen failures. The remaining 92 subjects were randomized in the study. Of these subjects, 76 (82.6%) completed the study treatment visits up to Visit 15 and are now in follow-up. The remaining 16 subjects did not complete the study treatment visits up to Visit 15 (Table 9).

TABLE 9

Disposition of Subjects

| Category | Treatment Group | | Overall (N = 92) |
|---|---|---|---|
| | Group A (N = 46) | Group B (N = 46) | |
| | Population, n (%) [1] | | |
| Screened | | | 98 |
| Randomized | 46 (100.0) | 46 (100.0) | 92 (100.0) |
| Intent-to-treat | 46 (100.0) | 45 (97.8) | 91 (98.9) |
| Per-Protocol | 32 (69.6) | 28 (60.9) | 60 (65.2) |
| Total number of subjects completed the study (Visit 15) | 37 (80.4) | 39 (84.8) | 76 (82.6) |
| Total number of subjects not completed the study (Visit 15) | 9 (19.6) | 7 (15.2) | 16 (17.4) |

Note:

[1] Percentage was calculated taking respective column header group count as denominator.

The following were the reasons, which led to the exclusion of 32 subjects from the PP population: Consent withdrawal (13 subjects); Lost to follow up (2 subjects); Death (2 subjects); Drop outs (1 subject); Protocol deviation(s); Decrease or increase in the ulcer size by 30% or more during 7 day screening period (14 subjects)

ITT Population: All subjects randomized to any treatment group, received at least one dose of study medication or reference treatment and performed study assessments within and/or outside the time window period specified in the protocol. The assessments performed outside time window period were re-assigned to the closest nominal time point of actual sample collection PP Analysis Population: All subjects who completed study assessments within the protocol defined window period for the assigned randomized time point and also completed all study assessments until Week 12. This included subjects who came for all the visits within or outside the window period, including subjects whose wounds had healed before Week 12. Subjects who had a major protocol deviation were excluded from the PP population. This included subjects who had an increase or decrease of more than 30% in wound size during the screening period of 7 days (per exclusion criteria no. 1 in the protocol)

Safety Population: All subjects who were randomized in the study to either of the treatment groups were used for the safety analysis The ITT population included 91 subjects; the PP population included 60 subjects; and the safety population included 92 subjects.

Primary Efficacy Endpoint: Mean Percent Wound Closure from Baseline to Week 12

Parametric Analysis: Table 10 summarizes the parametric analysis of the mean percent reduction of wound area from Baseline to Week 12 in the ITT population. Of 91 subjects in the ITT population, non-missing observations for change from Baseline to Week 12 for percent reduction of wound area were available for 63 subjects. The mean percent±SD reduction of wound area from Baseline to Week 12 was higher in Group A than Group B (Group A: 72.12%±128.52; Group B: 57.09%±80.88) but was not statistically significant (p-value=0.6567) as per parametric analysis.

TABLE 10

Mean Percent Reduction of Wound Area from Baseline to
Week 12 (Parametric analysis) ITT Population (N = 91)

|  | Treatment Group | |
| --- | --- | --- |
| Statistics | Group A (N = 46) | Group B (N = 45) |
| Total number of subjects evaluated | N = 63[1] | |
| Percent reduction of wound area from Baseline to Week 12 | | |
| n | 34 | 29 |
| Mean | 72.121 | 57.086 |
| SD | 128.5222 | 80.8795 |
| Median | 100.000 | 100.000 |
| Range (Min.:Max.) | (−648.91:100.00) | (−271.50:100.00) |
| LS Mean Estimate | 55.490 | 44.032 |
| Difference Estimate [2] | 11.4575 | |
| SE [3] | 25.6968 | |
| 95% CI (L.:U.) | (−39.53:62.44) | |
| p-value [3], [5] | 0.6567 | |

[1] "Total no. of subjects evaluated" represents subjects having non-missing observations for change from Baseline to Week 12 for percent reduction of wound area

[2] Difference estimate for Granexin ™ Gel plus SoC indicated (Granexin ™ Gel plus SoC) − SoC).

[3] SE of Granexin ™ Gel plus Standard of Care indicated Standard Error of Differences (Granexin ™ Gel plus SoC) − SoC).

[4] p-value for Granexin ™ Gel plus SoC indicated significance of treatment differences (Granexin ™ Gel plus SoC) − (SoC).

[5] ANCOVA mixed model with repeated measures was used to compare average percent reduction in wound area with treatment, visit and treatment*visit as factors and strata, wound duration, viable tissue, exudate level and the BMI as covariates using PROC Mixed procedure of SAS software.

The parametric analysis of the mean percent reduction of wound area from Baseline to Week 12 in the PP population is summarized in Table 11. Of the 60 subjects in the PP population, non-missing observations for change from Baseline to Week 12 for reduction of wound area were available for 57 subjects. The mean percent±SD reduction of wound area from Baseline to Week 12 was statistically significantly higher in Group A than in Group B (Group A: 93.58%±17.67; Group B: 52.14%±84.14; p-value=0.0202).

TABLE 11

Mean Percent Reduction of Wound Area from Baseline to
Week 12 (Parametric analysis) PP Population (N = 60)

|  | Treatment Group | |
| --- | --- | --- |
| Statistics | Group A (N = 32) | Group B (N = 28) |
| Total number of subjects evaluated | N = 57[1] | |
| Percent reduction of wound area from Baseline to Week 12 | | |
| n | 31 | 26 |
| Mean | 93.582 | 52.135 |
| SD | 17.6708 | 84.1427 |
| Median | 100.000 | 100.000 |
| Range (Min.:Max.) | (27.61:100.00) | (−271.50:100.00) |
| LS Mean Estimate | 69.038 | 30.178 |
| Difference Estimate [2] | 38.8605 | |
| SE [3] | 16.4998 | |
| 95% CI (L.:U.) | (6.18:71.54) | |
| p-value [4], [5] | 0.0202 | |

Note:

[1] "Total no. of subjects evaluated" represents subjects having non-missing observations for change from Baseline to Week 12 for percent reduction of wound area

[2] Difference estimate for Granexin ™ Gel plus SoC indicated (Granexin ™ Gel plus SoC) − SoC).

[3] SE of Granexin ™ Gel plus Standard of Care indicated Standard Error of Differences (Granexin ™ Gel plus SoC) − SoC).

[4] p-value for Granexin ™ Gel plus SoC indicated significance of treatment differences (Granexin ™ Gel plus SoC) − (SoC).

[5] ANCOVA mixed model with repeated measures was used to compare average percent reduction in wound area with treatment, visit and treatment*visit as factors and strata, wound duration, viable tissue, exudate level and the body mass index as covariates using PROC Mixed procedure of SAS software.

General Note:

Group A indicates Granexin ™ Gel plus SoC and Group B indicates SoC only

SD: Standard Deviation,

Min: Minimum,

Max: Maximum,

CI: Confidence Interval,

L: Lower Limit,

U: Upper Limit

Missing data was accounted by using repeated measures analysis.

Mean percent reduction from Baseline = ((Baseline − week X)/Baseline)*100

To confirm the applicability of parametric statistical inference methodology in the wound reduction analysis, it was tested whether the data followed normal distribution. Using PROC UNIVARIATE of SAS® (version 9.1.3) Shapiro-Wilk W statistic was calculated. The Shapiro-Wilk p-value <0.0001 and this indicated that the data did not follow the normal distribution. Therefore, the hypothesis of normal distribution of the data in the sample was rejected and non-parametric analysis was also conducted.

Table 12 summarizes the non-parametric analysis for mean percent reduction of wound area from Baseline to Week 12 in the ITT population. The Wilcoxon Mann-Whitney U test is a non-parametric test which determines whether there is a difference in two samples of independent observations. The actual sum of scores (1215.00) obtained by adding the ranks of both groups after sorting the data of wound size reduction in ascending order, was found higher in Group A subjects than the expected sum of scores i.e. sum of scores when there is no difference in two groups, under the null hypothesis (1088.00) and in Group B, the actual sum of scores (801.00) was found lower than the expected sum of the scores under the null hypothesis (928.00). Subjects in Group A had statistically significantly higher percent reduction of wound area from Baseline to Week 12 than Group B subjects (p-value=0.0287).

TABLE 12

Mean Percent Reduction of Wound Area from Baseline to Week 12 (Non-parametric analysis) IIT Population (N = 91)

| Statistics | Treatment Group | |
|---|---|---|
| | Group A (N = 46) | Group B (N = 45) |
| Percent reduction of wound area from Baseline to Week 12 | | |
| Sum of Score | 1215.00 | 801.00 |
| Expected Sum of Scores under $H_o$ | 1088.00 | 928.00 |
| p-value [1] | 0.0287 | |

Note:
[1] p-value is evaluated by using non-parametric Wilcoxon Mann-Whitney U test between treatment group.
General Note:
Mean percent reduction from Baseline = ((Baseline − week X)/Baseline)*100
$H_o$: Null Hypothesis Table 13 summarizes the non-parametric analysis for mean percent reduction of wound area from Baseline to Week 12 in the PP population. The addition of the ranks of both groups obtained after sorting the data of wound size reduction in ascending order gave the actual sum of scores as 1036.00 which was found to be higher in Group A subjects than the expected sum of scores (899.00) i.e. sum of scores when there is no difference in the two groups, under the null hypothesis and in Group B the actual sum of scores (617.00) was found to be lower than the expected sum of the scores under the null hypothesis (754.00). Subjects in Group A had statistically significant higher percentage of reduction of wound area from Baseline to Week 12 than Group B subjects (p-value=0.0069).

TABLE 13

Mean Percent Reduction of Wound Area from Baseline to Week 12 (Non-parametric analysis) PP Population (N = 60)

| Statistics | Treatment Group | |
|---|---|---|
| | Group A (N = 32) | Group B (N = 28) |
| Percent reduction of wound area from Baseline to Week 12 | | |
| Sum of Score | 1036.00 | 617.00 |
| Expected Sum of Scores under $H_o$ | 899.00 | 754.00 |
| p-value [1] | 0.0069 | |

[1] p-value is evaluated by using non-parametric Wilcoxon Mann-Whitney U test between treatment group.
General Note:
Mean percent Reduction from Baseline = ((Baseline − week X)/Baseline)*100
$H_o$: Null Hypothesis The parametric evaluation of mean percent wound closure from Baseline to Week 4 in the ITT population is summarized in Table 14. Of 91 subjects in the ITT population, non-missing observations from Baseline to Week 4 for percent reduction of wound area were available for 60 subjects. The mean percent±SD reduction of wound area from Baseline to Week 4 was 53.3000±126.23 in Group A subjects and 52.9200±42.60 in Group B subjects; but the reduction in Group A was not statistically significant compared to Group B (p-value=0.8234).

TABLE 14

Mean Percent Reduction of Wound Area from Baseline to Week 4 (Parametric analysis) ITT Population (N = 91)

| Statistics | Treatment Group | |
|---|---|---|
| | Group A (N = 46) | Group B (N = 45) |
| Total no. of subjects evaluated | N = 60[1] | |
| Percent reduction of wound area from Baseline to week 4 | | |
| N | 33 | 27 |
| Mean | 53.306 | 52.920 |
| SD | 126.2293 | 42.6001 |
| Median | 81.414 | 61.484 |
| Range (Min.:Max.) | (−626.65:100.00) | (−72.94:100.00) |
| LS Mean Estimate | 46.931 | 41.098 |
| Difference Estimate [2] | 5.8329 | |
| SE [3] | 26.0720 | |
| 95% CI (L.:U.) | (−45.87:57.54) | |
| p-value [4], [5] | 0.8234 | |

Note:
[1] "Total no. of subjects evaluated" represents subjects having non-missing observations for all the dependent and covariate variables
[2] Difference estimate for Granexin™ Gel plus SoC indicated (Granexin™ Gel plus SoC) − SoC).
[3] SE of Granexin™ Gel plus SoC indicated Standard Error of Differences (Granexin™ Gel plus SoC) − SoC).
[4] p-value for Granexin™ Gel plus SoC indicated significance of treatment differences (Granexin™ Gel plus SoC) − (SoC).
[5] ANCOVA mixed model with repeated measures was used to compare average percent reduction in wound area with treatment, visit and treatment*visit as factors and strata, wound duration, viable tissue, exudate level and the body mass index as covariates using PROC Mixed procedure of SAS software.

The parametric analysis of mean percent reduction of wound area from Baseline to Week 4 in the PP population is summarized in Table 15. Of the 60 subjects in the PP population, non-missing observations from Baseline to Week 4 were available for a total of 49 subjects. The mean percent±SD reduction of wound area from Baseline to Week 4 was 73.490%±35.52 in Group A subjects and 47.43%±43.61 in Group B subjects; but the reduction was not statistically significantly higher in Group A subjects than Group B (p-value=0.0871).

TABLE 15

Mean Percent Reduction of Wound Area from Baseline to Week 4 (Parametric analysis) PP Population (N = 60)

| Statistics | Treatment Group | |
|---|---|---|
| | Group A (N = 32) | Group B (N = 28) |
| Total no. of subjects evaluated | N = 49[1] | |
| Percent reduction of wound area from Baseline to week 4 | | |
| N | 26 | 23 |
| Mean | 73.487 | 47.430 |
| SD | 35.5187 | 43.6110 |
| Median | 88.167 | 56.931 |
| Range (Min.:Max.) | (−40.60:100.00) | (−72.94:100.00) |
| LS Mean Estimate | 53.184 | 24.019 |
| Difference Estimate [2] | 29.1649 | |
| SE [3] | 16.9134 | |
| 95% CI (L.:U.) | (−4.31:62.64) | |
| p-value [4], [5] | 0.0871 | |

Note:
[1] "Total no. of subjects evaluated" represents subjects having non-missing observations for all the dependent and covariate variables
[2] Difference estimate for Granexin™ Gel plus SoC indicated (Granexin™ Gel plus SoC) − SoC).
[3] SE of Granexin™ Gel plus SoC indicated Standard Error of Differences (Granexin™ Gel plus SoC) − SoC).
[4] p-value for Granexin™ Gel plus SoC indicated significance of treatment differences (Granexin™ Gel plus SoC) − (SoC).
[5] ANCOVA mixed model with repeated measures was used to compare average percent reduction in wound area with treatment, visit and treatment*visit as factors and strata, wound duration, viable tissue, exudate level and the body mass index as covariates using PROC Mixed procedure of SAS software.

Table 16 summarizes the non-parametric analysis for mean percent reduction of wound area from Baseline to Week 4 in the ITT population. In Group A, the expected sum of score under the null hypothesis i.e. sum of scores when there is no difference in two groups was 1006.50 and the actual sum of score was 1148.00 obtained by adding the ranks of both groups after sorting data of wound size reduction in ascending order, and for Group B, it was 823.50 and 682.00 for expected and actual, respectively. Group A subjects had a statistically significantly higher percent reduction of wound area than Group B subjects (p-value=0.0341).

TABLE 16

Mean Percent Reduction of Wound Area from Baseline to Week 4 (Non-parametric analysis) ITT Population (N = 91)

| Statistics | Treatment Group | |
|---|---|---|
| | Group A (N = 46) | Group B (N = 45) |
| Percent reduction of wound area from Baseline to Week 4 | | |
| Sum of Score | 1148.00 | 682.00 |
| Expected Sum of Score under Ho | 1006.50 | 823.50 |
| p-value [1] | 0.0341 | |

Note:
[1] p-value was evaluated by using non-parametric Wilcoxon Mann-Whitney U test between treatment group.
General Note:
Mean percent reduction from Baseline = ((baseline − week X)/baseline)*100
H$_o$: Null hypothesis The non-parametric analysis for mean percent reduction of wound area from Baseline to Week 4 in the PP population is summarized in Table 17 The expected sum of scores, which is the sum of scores when there is no difference in two groups, under the null hypothesis was 650.00 and the actual sum of scores, obtained by adding the ranks of both groups after sorting data of wound size reduction in ascending order, was higher with 773.00 for subjects treated with Granexin™ Gel plus SoC and in subjects treated with SoC only, the expected sum of score was 575.00 and the actual score was lower with 452.00. The percent reduction of wound area in Group A was statistically significantly higher than Group B subjects (p-value=0.0128).

TABLE 17

Mean Percent Reduction of Wound Area from Baseline to Week 4 (Non-parametric analysis) PP Population (N = 60)

| Statistics | Treatment Group | |
|---|---|---|
| | Group A (N = 32) | Group B (N = 28) |
| Percent reduction of wound area from Baseline to week 4 | | |
| Sum of Score | 773.00 | 452.00 |
| Expected under H$_o$ | 650.00 | 575.00 |
| p-value [1] | 0.0128 | |

Note:
[1] p-value was evaluated by using non-parametric Wilcoxon Mann-Whitney U test between treatment group.
General Note:
Mean percent Reduction from Baseline = ((Baseline − week X)/Baseline)*100
H$_o$: Null Hypothesis The intensity of pain experienced by the subjects was recorded on a Visual Analogue Scale of 1 to 10 where 1 indicated "no pain" and 10 indicated "extreme pain". The summary of subject self assessment of intensity of pain at all visits from Baseline to Week 12 for the ITT population have been given in FIG. 2.

Table 18 summarizes the intensity of pain as assessed by the subject at treatment Week 12 of the study. There was no statistically significant difference in the mean intensity of pain from Baseline to Week 12 between the 2 treatment groups (Group A, 0.5±1.46; Group B, 0.3±0.93; p-value=0.8484).

TABLE 18

Analysis of Subject Self Assessment of Intensity of Pain at Week 12 ITT Population (N = 91)

| Statistics | Treatment Group | |
|---|---|---|
| | Group A (N = 46) | Group B (N = 45) |
| Intensity of pain at Week 12 | | |
| N | 36 | 38 |
| Mean | 0.5 | 0.3 |
| SD | 1.46 | 0.93 |
| Median | 0.0 | 0.0 |
| Range (Min.:Max.) | (0:6) | (0:4) |
| Missing | 1 | 0 |
| p-value [1] | 0.8484 | |

Note:
[1] p-value was evaluated by using non-parametric Wilcoxon Mann-Whitney U test between treatment group.

Table 19 summarizes the intensity of pain as assessed by the subject at treatment Week 12 of the study for the PP population. There was no statistically significant difference in the mean intensity of pain at Week 12 between the 2 treatment groups (Group A, 0.4±1.22; Group B, 0.3±0.81; p-value=0.9683). The summary of subject self assessment of intensity of pain at all visits from Baseline to Week 12 for the PP population is given in FIG. 3.

TABLE 19

Analysis of Subject Self Assessment of Intensity of Pain at Week 12 PP Population (N = 60)

| Statistics | Treatment Group | |
|---|---|---|
| | Group A (N = 32) | Group B (N = 28) |
| Intensity of pain at Week 12 | | |
| n | 30 | 27 |
| Mean | 0.4 | 0.3 |
| SD | 1.22 | 0.81 |
| Median | 0.0 | 0.0 |
| Range (Min.:Max.) | (0:4) | (0:4) |
| Missing | 1 | 0 |
| p-value [1] | 0.9683 | |

Note:
[1] p-value was evaluated by using non-parametric Wilcoxon Mann-Whitney U test between treatment group.

The time taken for 100% wound closure for the ITT population is summarized in FIG. 4. Complete wound closure was defined as 100% epithelialization of the wound and the absence of drainage from the wound. One subject in Group A and 2 subjects in Group B had the visit date missing and were not included in the analysis (FIG. 4). Seventeen (37.0%) subjects in Group A and 25 (55.6%) subjects in Group B were censored. Of these, 2 (4.8%) subjects in Group B were lost-to-follow-up, 1 (2.4%) subject in Group A dropped out, 9 (21.4%) subjects (Group A: 7; Group B: 2) were withdrawn, and 31 (73.8%) subjects (Group A: 10; Group B: 21) did not have complete wound closure during the study period. One patient withdrew from the study but had complete wound closure and was therefore considered in the ITT population, but excluded from the PP population.

In Group A, 28 (60.9%) subjects and 18 (40.0%) subjects in Group B had 100% wound closure. The median duration of 100% wound closure in Group A was 6 weeks (90% CI was 5 to 11 weeks) and 11 weeks (90% CI: 9 to 18.29 weeks) in Group B. In Group B, for 1 subject the assessments were performed outside the window period; the assessment was reassigned to the closest nominal time point which was Visit 15 at 12 weeks. Statistically significantly less time was taken by subjects in Group A to achieve 100% wound closure than Group B subjects (p-value=0.0306).

TABLE 20

Summary of Time to Complete (100%) Wound Closure by Week 12 ITT Population (N = 91)

| | Treatment Group | |
|---|---|---|
| Statistics[1] | Group A (N = 46) | Group B (N = 45) |
| Number (%) of subjects with complete (100%) wound closure | 28 (60.9%) | 18 (40.0%) |
| Number (%) of censored subjects | 17 (37.0%) | 25 (55.6%) |
| Median duration (weeks) of complete wound closure (90% CI)[2] | 6.00 (5.00; 11.00) | 11.00 (9.00; 18.29) |
| p-value[3] | 0.0306 | |

Note:
[1]Percentage was calculated taking count of corresponding treatment groups as denominator.
[2]The median duration of complete wound closure was estimated by Kaplan-Meier method and also 90% confidence interval is calculated for the median duration of 100% wound closure.
[3]p-value is calculated using Log-rank test for treatment groups using Proc Lifetest procedure of SAS software
General Note:
Time to first complete wound closure where complete wound closure is defined as 100% epithelialization of the wound and the absence of drainage from the wound.
Censoring: Subjects without occurrence of complete wound closure during study period, drop outs and lost-to-follow up subjects is censored at the time of last follow-up visit.
The data of 1 subject in Group A and 2 subjects in Group B were considered as missing. They had missing data after Screening or had missing visit date.

The time taken to complete (100%) wound closure in the PP population is summarized in Table 21 and FIG. 5 displays the Kaplan-Meier plot for time to 100% wound closure. Of the 32 subjects in Group A, 26 (81.3%) subjects had complete (100%) wound closure and 6 (18.8%) subjects were censored. Subjects who dropped out or were lost to follow-up were already excluded from the PP population and subjects who did not have complete wound closure during the study period were censored. The duration of wound closure was in the range of 4 weeks to 10.86 weeks and the median duration was 6 weeks. Of the 28 subjects in Group B, 15 (53.6%) subjects had complete wound closure and 13 (46.4%) subjects were censored. The duration of wound closure was in the range of 9 weeks to 18.29 weeks. The median duration of time to complete wound closure along with 90% CI was 14.64 weeks. The time taken for complete wound closure was lower in Group A as compared to Group B which was statistically significant (p-value=0.0057).

TABLE 21

Summary of Time to Complete (100%) Wound Closure by Week 12 PP Population (N = 60)

| | Treatment Group | |
|---|---|---|
| Statistics[1] | Group A (N = 32) | Group B (N = 28) |
| Number (%) of subjects with complete (100%) wound closure | 26 (81.3%) | 15 (53.6%) |
| Number (%) of censored subjects | 6 (18.8%) | 13 (46.4%) |
| Median duration (weeks) of complete wound closure (90% CI)[2] | 6.00 (4.00; 10.86) | 14.64 (9.00; 18.29) |
| p-value[3] | 0.0057 | |

Note:
[1]Percentage was calculated taking count of corresponding treatment groups as denominator
[2]The median duration of complete wound closure was estimated by Kaplan-Meier method and also 90% confidence interval was calculated for the median duration of 100% wound closure.
[3]p-value was calculated using Log-rank test for treatment groups using Proc Lifetestt procedure of SAS software The time taken to complete 50% wound closure by Week 12 in the ITT population is summarized in Table 22 and FIG. 6 displays the Kaplan-Meier plot for time to 50% wound closure in the ITT population. One subject in Group A and 2 subjects in Group B had the visit date missing and were not included in the analysis (FIG. 6). In Group A, 9(19.60) subjects and 11 (24.4%) subjects in Group B were censored. Overall, of the 20 censored subjects, 2(10.0%) subjects were lost-to-follow-up, 1 (5.00%) subject dropped out, 9(45.00%) subjects were withdrawn, and 8(40.00%) subjects did not have 50% wound closure during the study period.

Thirty six (78.3%) subjects in Group A and 32 (71.1%) subjects in Group B had 50% wound closure. The median duration of 50% wound closure was 2 weeks (900% CI was 2 to 3.14 weeks) in Group A and 3.29 weeks (90% CI was 3 to 4.14 weeks) in Group B. The time taken for 50% wound closure was not statistically significantly lower in Group A than Group B (p-value=0.5433).

TABLE 22

Summary of Time to Complete 50% Wound Closure by Week 12 ITT Population (N = 91)

| Statistics [1] | Treatment Group | |
| --- | --- | --- |
| | Group A (N = 46) | Group B (N = 45) |
| Number (%) of subjects with 50% wound closure | 36 (78.3%) | 32 (71.1%) |
| Number (%) of censored subjects | 9 (19.6%) | 11 (24.4%) |
| Median duration (weeks) of complete wound closure (90% CI) [2] | 2.00 (2.00; 3.14) | 3.29 (3.00; 4.14) |
| p-value [3] | 0.5433 | |

Note:

[1] Percentage was calculated taking count of corresponding treatment groups as denominator

[2] The median duration of complete wound closure was estimated by Kaplan-Meier method and also 90% confidence interval is calculated for the median duration of 50% wound closure.

[3] p-value was calculated using Log-rank test for treatment groups using Proc Lifetestt procedure of SAS software The time taken to complete 50% wound closure in the PP population is summarized in Table 23 and FIG. 7 displays the Kaplan-Meier plot for time to 50% wound closure in the PP population. Of the 32 subjects in Group A, 30 (93.8) subjects completed 50% wound closure and 2(6.30%) subjects were censored. In Group A, the duration of wound closure was in the range of 2 weeks to 3.14 weeks and the median duration was 2 weeks. Of the 28 subjects in Group B, 25 (89.30%) subjects had 50% wound closure and 3(10.70%) subjects who did not have at least 50% wound closure during the study period were censored. The duration of wound closure was in the range of 3 weeks to 5 weeks. The median duration of time to complete 50% wound closure was 4.07 weeks. The time taken for complete wound closure was not statistically significantly lower in subjects in Group A as compared to the time taken by subjects in Group B (p-value=0.2084).

TABLE 23

Summary of Time to Complete (50%) Wound Closure by Week 12 PP Population (N = 60)

| Statistics[1] | Treatment Group | |
| --- | --- | --- |
| | Group A (N = 32) | Group B (N = 28) |
| Number (%) of subjects with 50% wound closure | 30 (93.8%) | 25 (89.3%) |
| Number (%) of censored subjects | 2 (6.3%) | 3 (10.7%) |
| Median duration (weeks) of complete wound closure (90% CI)[2] | 2.00 (2.00; 3.14) | 4.07 (3.00; 5.00) |
| p-value[3] | 0.2084 | |

Note:

[1] Percentage was calculated taking count of corresponding treatment groups as denominator

[2] The median duration of complete wound closure is estimated by Kaplan-Meier method and also 90% confidence interval is calculated for the median duration of 100% wound closure.

[3] p-value is calculated using Log-rank test for treatment groups using Proc Lifetestt procedure of SAS software Additional to the Kaplan-Meier Model, Cox Proportional Hazard Regression Model was used to compare the event-time distribution function between the two treatment groups. This analysis was conducted to evaluate if one or more covariates were associated with the time to complete 100% or 50% wound closure. Table 24 summarizes the Cox Proportional Hazard Regression Analysis of time to complete wound closure in the ITT population. The effect of covariates estimated by the proportional hazard model is reported as hazard ratios. Though treatment was not a significant factor affecting wound closure (p-value=0.2903), the subjects treated with Granexin™ Gel plus SoC would have wound closure 1.568 times more than the subjects treated with SoC only. All other parameters, including wound size, wound duration, baseline wound depth, and use of dressings did not affect wound closure in both the treatment groups.

TABLE 24

Analysis of Time to Complete (100%) Wound Closure ITT Population (N = 91)

| Statistics [1] | Hazard Ratio [1] | 95% CI for Hazard Ratio | | p-value |
| --- | --- | --- | --- | --- |
| | | Lower | Upper | |
| Treatment group | 1.568 | 0.681 | 3.607 | 0.2903 |
| Wound size | 0.999 | 0.997 | 1.000 | 0.1265 |
| Wound duration | 0.995 | 0.976 | 1.013 | 0.5754 |
| Baseline wound depth | 0.782 | 0.239 | 2.558 | 0.6839 |
| BMI | 0.966 | 0.861 | 1.084 | 0.5592 |
| Use of dressings | — | — | — | — |

Note:

[1] Cox Proportional Hazard ratio with 95% confidence interval and p-value was calculated using PROC PHREG procedure.

Cox Proportional Hazard Regression Analysis for time to 100% closure in the PP population (Table 25) shows that though treatment was not a significant factor affecting wound closure (p-value=0.0856), the subjects treated with Granexin™ Gel plus SoC would have wound closure 2.339 times more than the subjects treated with SoC only. Similarly, baseline wound depth and BMI were not significant factors (baseline wound depth: p-value=0.4554, BMI: p-value=0.4435) but would affect wound closure by 1.715 times and 1.050 times, respectively. All other parameters, including wound size, wound duration, and use of dressings did not affect wound closure in both the treatment groups.

TABLE 25

Analysis of Time to Complete (100%) Wound Closure (Cox's Proportional Hazards Regression Analysis) PP Population (N = 60)

| Statistics[1] | Hazard Ratio[1] | 95% CI for Hazard Ratio Lower | 95% CI for Hazard Ratio Upper | p-value |
|---|---|---|---|---|
| Treatment group | 2.339 | 0.888 | 6.161 | 0.0856 |
| Wound size | 0.999 | 0.997 | 1.000 | 0.1703 |
| Wound duration | 0.992 | 0.974 | 1.011 | 0.4177 |
| Baseline wound depth | 1.715 | 0.416 | 7.071 | 0.4554 |
| BMI | 1.050 | 0.927 | 1.190 | 0.4435 |
| Use of dressings | — | — | — | — |

Note:
[1]Cox Proportional Hazard ratio with 95% confidence interval and p-value was calculated using PROC PHREG procedure.

None of the covariates such as treatment group, wound size, wound duration, baseline wound depth, and BMI were significantly associated with time to 50% wound closure. However, in the PP population, subjects treated with Granexin™ Gel plus SoC would have wound closure 1.186 times more than subjects in Group B.

FIG. 8 and FIG. 9 display the average wound closure in the ITT and PP populations in the study, respectively.

Safety evaluation: Brief Summary of Adverse Events

Of 92 subjects, 71 (77.2%) subjects did not report any AEs and 21 (22.8%) subjects reported 26 AEs. Out of 26 AEs, 18 (69.2%) were mild and 2 (15.4%) events in each treatment group were moderate and severe, respectively. A total of 21 (80.8%) AEs were not related and 5 (19.2%) AEs were unlikely related to the study drug or treatment. None of the AEs were related to the study drug. Of the 26 events, 18 (69.2%) recovered and 3(11.5%) events recovered with sequelae. No action was taken against 22 AEs. None of the subjects withdrew due to an AE.

A total of 5 subjects, of which 2 (4.3%) subjects were in Group A and 3 (6.5%) subjects in Group B, reported 5 SAEs. One subject in Group A died due to an unknown cause and 1 subject in Group B died due to myocardial infarction (Table 26).

TABLE 26

Overview of Adverse Events-Safety Population (N = 92)

| Statistics | Group A (N = 46) | Group B (N = 46) | Overall (N = 92) |
|---|---|---|---|
| Total number of AEs reported | 13 | 13 | 26 |
| Subjects reporting Any AEs [1] | 11 (23.9%) | 10 (21.7%) | 21 (22.8%) |
| Subjects reporting 1 AE | 9 (19.6%) | 7 (15.2) | 16 (17.4%) |
| Subjects reporting >1AE | 2 (4.3%) | 3 (6.5%) | 5 (5.4%) |
| Subjects reporting No AEs [1] | 35 (76.1%) | 36 (78.3%) | 71 (77.2%) |
| Number of AEs with severity of: [2] | | | |
| Mild | 9 (69.2%) | 9 (69.2%) | 18 (69.2%) |
| Moderate | 2 (15.4%) | 2 (15.4%) | 4 (15.4%) |
| Severe | 2 (15.4%)) | 2 (15.4%) | 4 (15.4%) |
| Number of AEs with relationship of: [2] | | | |
| Not Related | 10 (76.9%) | 11 (84.6%) | 21 (80.8%) |
| Unlikely | 3 (23.1%) | 2 (15.4%) | 5 (19.2%) |
| Possible | 0 (0.0%) | 0 (0.0%) | 0 (0.0%) |
| Probable | 0 (0.0%) | 0 (0.0%) | 0 (0.0%) |
| Definite | 0 (0.0%) | 0 (0.0%) | 0 (0.0%) |
| Number of AEs by outcome:[2] | | | |
| Recovered | 7 (53.8%) | 11 (84.6%) | 18 (69.2%) |
| Recovered with sequelae | 2 (15.4%) | 1 (7.7%) | 3 (11.5%) |
| Ongoing when subject completed the study | 3 (23.1%) | 0 (0.0%) | 3 (11.5%) |
| Death | 1 (7.7%) | 1 (7.7%) | 2 (7.7%) |
| Unknown | 0 | 0 | 0 |
| Number of AEs by action taken:[2] | | | |
| None | 11 (84.6%) | 11 (84.6%) | 22 (84.6%) |
| Discontinued study drug | 2 (15.4%) | 2 (15.4%) | 4 (15.4%) |
| Subjects reporting AEs leading to withdrawal [1] | 0 | 0 | 0 |
| Subjects Reporting SAEs [1] | 2 (4.3%) | 3 (6.5%) | 5 (5.4%) |
| Subject reporting death | 1 (2.2%) | 1 (2.2%) | 2 (2.2%) |

Note:
[1] Percentage was calculated by taking respective column header group count as denominator.
[2] Percentage was calculated by taking count of 'Total Number of AEs Reported' in corresponding treatment group as denominator.

The AEs by MedDRA system organ class and preferred term are summarized in Table 27. There was no statistically significant difference in the number of subjects with at least 1 AE between the 2 treatment groups (p-value=0.8038). In Group A, more than 5% study population reported wound complication (Group A: 5 [10.9%] subjects) and headache (Group A: 4 [8.7%] subjects) as AEs in this study.

TABLE 27

Summary of Adverse Events by MedDRA System Organ Class and Preferred Term Safety Population (N = 92)

| System Organ Class/Preferred Term | Group A (N = 46) | Group B (N = 46) | Overall (N = 92) | p-value [2] |
|---|---|---|---|---|
| Total number of subjects with at least one AEs | 11 (23.9%) | 10 (21.7%) | 21 (22.8%) | 0.8038 |
| Total number of AEs reported | 13 | 13 | 26 | |
| Cardiac disorders | 0 | 1 (2.2%) | 1 (1.1%) | |
| Myocardial infarction[3] | 0 [0] | 1 (2.2%) [1] | 1 (1.1%) [1] | |
| Gastrointestinal disorders | 0 | 1(2.2%) | 1 (1.1%) | |
| Toothache | 0 [0] | 1 (2.2%) [1] | 1 (1.1%) [1] | |
| General disorders and administration site conditions | 1 (2.2 %) | 0 | 1 (1.1%) | |

TABLE 27-continued

Summary of Adverse Events by MedDRA System Organ Class and Preferred Term Safety Population (N = 92)

| System Organ Class/Preferred Term | Group A (N = 46) | Group B (N = 46) | Overall (N = 92) | p-value [2] |
|---|---|---|---|---|
| Death | 1 (2.2%) [1] | 0 [0] | 1 (1.1%) [1] | |
| Infections and infestations | 0 | 2 (4.3%) | 2 (2.2%) | |
| Cellulitis | 0 [0] | 1 (2.2%) [1] | 1 (1.1%) [1] | |
| Respiratory tract infection | 0 [0] | 1 (2.2%) | 1 (1.1%) [1] | |
| Injury, poisoning and procedural complications | 6 (13.0%) | 2 (4.3%) | 8 (8.7%) | |
| Wound complication | 5 (10.9%) [6] | 2 (4.3%) [3] | 7 (7.6%) [9] | |
| Foot fracture | 1 (2.2%) [1] | 0 [0] | 1 (1.1%) [1] | |
| Metabolism and nutrition disorders | 0 | 1 (2.2%) | 1 (1.1) | |
| Diabetes mellitus inadequate control | 0 [0] | 1 (2.2%) [1] | 1 (1.1%) [1] | |
| Musculoskeletal and connective tissue disorders | 0 | (6.5%) | 3 (3.3 %) | |
| Back pain | 0 [0] | 1 (2.2%) [1] | 1 (1.1%) [1] | |
| Pain in extremity | 0 [0] | 2 (4.3%) [2] | 2 (2.2%) [2] | |
| Nervous system disorders | 4 (8.7%) | 1 (2.2%) | 5 (5.4%) | |
| Headache | 4 (8.7%) [4] | 1 (2.2%) [1] | 5 (5.4%) [5] | |
| Respiratory, thoracic and mediastinal disorders | 1 (2.2%) | 0 | 1 (1.1%) | |
| Pneumonitis | 1 (2.2%) [1] | 0 [0] | 1 (1.1%) [1] | |
| Skin and subcutaneous tissue disorders | 0 | 1 (2.2) | 1 (1.1%) | |
| Blister | 0 [0] | 1 (2.2%) [1] | 1 (1.1%) [1] | |

Note:
[1] Percentage was calculated by taking respective column header group count as denominatior.
[2] p-value was calculated by comparing two treatment group using Chi-square test.
[3] Myocardial infarction led to death of the subject Out of 26 AEs, 2 events each in both the treatment groups were considered severe AEs. In both Group A and B, 9(69.2%) AEs each were mild, 2 (15.4%) AEs each were moderate and 2 (15.4%) AEs each were severe. The AEs with severe intensity were death and foot fracture in Group A and myocardial infarction and inadequate control of diabetes mellitus in Group B. None of the severe AEs were related to the study drug or study treatment Overall, 10 (76.9%) AEs in Group A and 11 (84.6%) AEs in Group B were not related, 3 (23.1%) AEs in Group A and 2 (15.4%) AEs in Group B were unlikely related. None of the AEs were related to Granexin™ Gel or study treatment.

Two AEs of death (Subject 903) and foot fracture (Subject 504) in Group A led to study drug discontinuation. In Group B, two events of cellulitis (Subject 524) and wound complication (Subject 806 with increase in size of ulcer) led to discontinuation of study treatment.

Three events recovered with sequelae (Group A, foot fracture [Subject 504] and wound complication [Subject 508]; Group B, right foot cellulitis [Subject 524]). One subject in each treatment group reported death (Group A, unknown cause [Subject 903]; Group B, myocardial infarction [Subject 827]).

Table 28 summarizes SAEs by MedDRA system organ class and preferred term. Five (5.4%) subjects (Group A: 2 subjects; Group B: 3 subjects) reported SAEs where foot fracture (Subject 504) and death due to unknown cause (Subject 903) were reported by Group A subjects; and myocardial infarction (Subject 827), diabetes mellitus inadequate control (Subject 201), and cellulitis (Subject 524) were reported by Group B subjects.

TABLE 28

Summary of Serious Adverse Events by MedDRA System Organ Class and Preferred Term Safety Population (N = 92)

| System Organ Class/ Preferred Term | Group A (N = 46) | Group B (N = 46) | Overall (N = 92) |
|---|---|---|---|
| Total number of subjects with at least one SAE | 2 (4.3) | 3 (6.5) | 5 (5.4) |
| Total number of SAEs | 2 | 3 | 5 |
| Cardiac disorders | 0 (0.0) | 1 (2.2) | 1 (1.1) |
| Myocardial infarction[2] | 0 (0.0) [0] | 1 (2.2) [1] | 1 (1.1) [1] |
| General disorders and administration site conditions | 1 (2.2) | 0 (0.0) | 1 (1.1) |
| Death | 1 (2.2) [1] | 0 (0.0) [0] | 1 (1.1) [1] |
| Infections and infestations | 0 (0.0) | 1 (2.2) | 1 (1.1) |
| Cellulitis | 0 (0.0) [0] | 1 (2.2) [1] | 1 (1.1) [1] |
| Injury, poisoning and procedural complications | 1 (2.2) | 0 (0.0) | 1 (1.1) |
| Foot fracture | 1 (2.2) [1] | 0 (0.0) [0] | 1 (1.1) [1] |
| Metabolism and nutrition disorders | 0 (0.0) | 1 (2.2) | 1 (1.1) |
| Diabetes mellitus inadequate control | 0 (0.0) [0] | 1 (2.2) [1] | 1 (1.1) [1] |

Note:
[1] Percentage was calculated by taking respective column header group count as denominator.
[2] Myocardial infarction led to death of the subject.

TABLE 29

SAEs by Severity, Outcome, and Action Taken

| Subject ID | Severity | Relationship to Study Drug/Study Treatment | Action Taken | Outcome |
|---|---|---|---|---|
| 903 | Severe | Not related | None | Fatal |
| 827 | Severe | Not related | None | Fatal |
| 201 | Severe | Not related | None | Recovered |
| 504 | Severe | Not related | Discontinued Study drug | Recovered with sequelae |
| 524 | Moderate | Not related | Discontinued Study drug | Recovered with sequelae |

Safety Conclusions: Overall, 21 subjects reported 26 AEs of which majority were mild in intensity. A total of 4 moderate and 4 severe AEs were reported in this study. In Group A, death and foot fracture were the severe AEs and myocardial infarction and inadequate control of diabetes mellitus were severe AEs reported in Group B. All the severe AEs were not related to study treatment. None of the AEs reported were related to Granexin™ Gel or study treatment. Of the 26 events, 18 (69.2%) recovered and 3(11.5%) events recovered with sequelae. No action was taken against 22 AEs. Study drug or treatment was discontinued in a 2 subjects each in Group A and Group B. None of the subjects withdrew due to an AE. Five subjects reported 5 SAEs. None of the SAEs, including 1 fatal event in Group A, were related to Granexin™ Gel.

Discussion and overall conclusions: This was a double blind, randomized, prospective, parallel group, multi-center Phase II study conducted at 8 centers in India to evaluate the efficacy and safety of Granexin™ Gel in the treatment of DFU. The total duration of the study was 12 months, including 6 months enrollment period and 6 months for study procedures (3 months each for efficacy and safety analyses). Hence, the study duration for an individual subject was approximately 6 months, including 18 visits. For interim analysis, data up to 12 weeks (Visit 15) was considered. A total of 98 subjects with DFU were screened for this study and 6 were found to be screen failures. The remaining 92 subjects were randomized in the study to receive Granexin™ Gel plus SoC or only SoC in the treatment of DFU. Of these subjects, 76 (82.6%) completed the study treatment visits up to Visit 15 and are now in the follow-up stage of the study.

The primary efficacy endpoint of the study was to evaluate mean percent wound closure from Baseline to Week 12. The non-parametric Wilcoxon Mann-Whitney U test was used to analyze mean percent reduction of wound area from Baseline to Week 12 in both the treatment groups since the data did not follow a normal distribution, as confirmed by a Shapiro-Wilk p-value <0.0001 and a non-linear Q-Q plot. In the PP population, subjects treated with Granexin™ Gel plus SoC (Group A) showed statistically significantly higher percent wound closure from Baseline to Week 12 compared to subjects treated with SoC alone (Group B) (p value=0.0069), suggesting that at Week 12 wounds treated with Granexin™ Gel plus SoC healed better than the wounds treated with SoC alone.

The secondary endpoints of the study were to assess mean percent wound closure at Week 4, subject assessment of pain, and time to complete wound closure. At Week 4 in the PP population, Group A subjects showed statistically significantly higher percent reduction of wound area from Baseline compared to Group B subjects (p-value=0.0128; Wilcoxon Mann-Whitney U test). There was no statistically significant difference in intensity of pain as assessed by the subject from Baseline to Week 12 between the 2 treatment groups (p-value=0.8484; Wilcoxon Mann-Whitney U test), hence Granexin™ Gel did not affect the intensity of pain experienced by the subjects as recorded on a Visual Analogue Scale of 1 to 10.

Complete wound closure was defined as 100% epithelialization of the wound and the absence of drainage from the wound. Group A subjects in the PP population took significantly less time to achieve 100% wound closure than Group B subjects in the PP population (median duration: Group A, 6 weeks; Group B, 14.64 weeks; p-value=0.0057; log-rank test). However, in the PP population the time taken for 50% wound closure was not significantly lower in Group A as compared to Group B (median duration: Group A, 2 weeks; Group B, 4.07 weeks; p-value=0.2084; log-rank test). The categorical analysis of incidence of 100% and 50% wound closure at Week 12 was conducted and the subjects who had 100% wound closure were considered as responders. The number of responders in Group A in the PP population was significantly higher than in Group B (100% wound closure: p-value=0.0104; 50% wound closure: p-value=0.0063; Chi-square analysis), indicating that the wounds treated with Granexin™ Gel plus SoC have a higher frequency of 100% and 50% epithelialization than wounds treated with SoC alone.

Cox Proportional Hazard Regression Model was used to compare the event-time distribution function between the treatment groups. This analysis was conducted to evaluate if one or more covariates were associated with the time to complete 100% or 50% wound closure. Cox Proportional Hazard Regression Analysis for time to 100% wound closure showed that in the PP population though treatment was not a significant factor affecting wound closure. Group A subjects demonstrated 2.3 times higher wound closure than Group B subjects. In addition, baseline wound depth and BMI were not significant factors but affected wound closure by 1.715 times and 1.050 times, respectively. All other parameters, including wound size, wound duration, and use of dressings did not have a statistically significant difference in affecting wound closure for both the treatments. Cox Proportional Hazard Regression Analysis for time to 50% wound closure showed that none of the covariates (treatment group, wound size, wound duration, baseline wound depth, and BMI) were significantly associated with time to 50% wound closure. However, Group A subjects had 1.186 times more wound closure than Group B subjects.

The safety variable was to evaluate the incidence of treatment related AEs. Out of 92 subjects, 21 (22.8%) subjects reported 26 AEs. There was no significant difference in the number of subjects with at least 1 AE between the 2 treatment groups (Group A, 11; Group B, 10; p-value=0.8038). A total of 4 AEs were of severe intensity. None of the AEs were related to the Granexin™ Gel. None of the subjects withdrew due to an AE. A total of 5 (5.4%) subjects reported 5 SAEs of which 2 were Group A subjects and 3 were Group B subjects, none of the SAEs was related to Granexin™ Gel or study treatment. In Group A, 1 death was reported due to an unknown cause and 1 death in Group B occurred due to myocardial infarction.

In conclusion, Granexin™ Gel along with SoC has shown to accelerate wound healing in subjects with DFU, making it an efficacious, safe, and well tolerated therapeutic option for the treatment of DFU.

Example 4. Treatment of Venous Leg Ulcers

A Phase II, Randomized, Prospective, Double Blind, Parallel Group, Multi-Center Study to Determine the Safety and Efficacy of Granexin™ Gel in the Treatment of Venous Leg Ul This was a double blind, multi-center, phase II study to evaluate the efficacy and safety of Granexin™ Gel in the treatment of Venous Leg Ulcer (VLU). Total duration of the study was 11 months. The enrollment period of the study was 5 months and 6 months for study procedures. Study duration for individual subjects was 6 months and each subject was to attend a total of 18 visits during the study. Subjects were randomized to 1 of 2 treatment groups: Group A: Granexin™ Gel plus Standard Of Care (SoC) in treatment of VLU Group B: SoC in treatment of VLU Subjects in Group A received Granexin™ Gel (10 μM ACT1 peptide) plus SoC compared to SoC alone in Group B. The total study duration for efficacy assessments was 12 weeks with additional 12 weeks follow up for safety evaluations. The study procedures were divided into 3 phases: Screening Phase (Day −7 through Day 0), Treatment Phase (Day 0 through Week 12), and Follow-up Phase (Month 4 through Month 6).

Subjects enrolled in the study may have had multiple ulcers but only one ulcer was considered as the target ulcer. According to the randomization schedule, subjects had their ulcer site treated with either Granexin™ Gel and SoC or SoC alone. Each subject in Group A was treated up to 14 applications of Granexin™ Gel over the initial 12 weeks of the study period. Other than the application of Granexin™ Gel for Group A subjects, management of the wound sites was similar in both groups.

Each subject was assessed weekly for the first 12 weeks, followed by monthly assessments for the next 3 months. Wound photographs were used to assess wound closure in all subjects. Safety was determined by Treatment Emergent Adverse Events (TEAEs).

The primary end point of the study is:
 The mean percent wound closure from Baseline to 12 weeks
The secondary end points are:
Mean percent wound closure at 4 weeks
Time to 50% wound closure
Time to complete wound closure where complete wound closure will be defined as 100% epithelialization of the wound and the absence of drainage from the wound
Subject self-assessment of intensity of pain
Incidence of treatment related adverse events (AE)
Inclusion Criteria:
A subject was enrolled in this study if he/she met the following criteria:
2. Male or female aged 18 years and older
2a. Female subjects were post-menopausal or surgically sterilized, or
2b. Female of child-bearing potential must have had a negative pregnancy test at Screening, and agreed to use hormonal contraceptive or intra-uterine device or diaphragm with spermicide or condom with spermicide or abstinence throughout the study
3. Subjects with ulcers of venous origin, as clinically determined by the Investigator by a positive venous reflux test (venous refilling <20 seconds) using Doppler Ultrasound for at least 4 weeks prior to screening day, which have not adequately responded to conventional ulcer therapy
4. Ulcers that extend through the epidermis but not through muscle, tendon, or bone (Stage II or III ulcers as defined by the International Association of Enterostomal Therapists)
5. Surface ulcer between 0.5 cm$^2$ and 40 cm$^2$ post debridement
6. Signed informed consent form
Exclusion Criteria:
A subject was not eligible for this study if he/she met any of the following criteria:
 1. Decrease or increase in the ulcer size by 30% or more during 7 day screening period
 2. Cannot tolerate or comply with compression therapy
 3. An ulcer which showed signs of severe clinical infection, defined as pus oozing from ulcer site
 4. The ulcer to be treated required operative debridement
 5. An ulcer positive for β-hemolytic *Streptococcus* upon culture
 6. The ulcer had more than 50% slough, significant necrotic tissue, osteomyelitis, bone, tendon, or capsule exposure or avascular ulcer beds
 7. Highly exuding wounds (wounds that required a daily dressing change) df
 8. Ankle Brachial Pressure Index (ABPI)<0.65
 9. With active systemic infections
 10. With clinically significant medical conditions as determined by the Investigator which would impair wound healing including renal, hepatic, hematologic, neurologic, or immune disease.
Examples included but were not limited to:
 a. Renal insufficiency as an estimated glomerular filtration rate which was <30 mL/min/1.7 m$^2$
 b. Abnormal blood biochemistry defined as 3 times that of the upper limit of the normal range
 c. Hepatic insufficiency defined as total bilirubin >2 mg/dL or serum albumin <25 g/L
 d. HbA1c>9.0%
 e. Hemoglobin <10 g/dL
 f. Hematocrit <0.30
 g. Platelet count <100,000
 11. Presence of an active systemic or local cancer or tumor of any kind (with the exception of non-melanoma skin cancer)
 12. With active osteomyelitis of the study foot
 13. With severe rheumatoid arthritis (with more than 20 persistently inflamed joints, or below lower normal limit blood albumin level, or evidence of bone and cartilage damage on X-ray, or inflammation in tissues other than joints) and other collagen vascular diseases
 14. With active connective tissue disease
 15. Treatment with systemic corticosteroids (>15 mg/day), or current immunosuppressive agents
 16. Previous or current radiation therapy or likelihood to receive this therapy during study participation
 17. Pregnant or nursing subjects
 18. Known prior inability or unavailability to complete required study visits during study participation
 19. A psychiatric condition (e.g. suicidal ideation) or chronic alcohol or drug abuse problem, determined from the subject's medical history, which, in the opinion of the Investigator, may pose a threat to subject compliance
 20. Use of any investigational drug or therapy within the 28 days prior to Screening
 21. Any other factor which may have, in the opinion of the Investigator, compromised participation and follow-up in this study Granexin™ Gel (100 µM ACT1 peptide) was applied topically on the wound on Day 0 (Baseline visit), Day 3, Week 1, 2, 3, 4, 5, 6, 7, 8, 9, 10, 11, and 12. The duration of the study was 11 months which included 5 months enrollment period. Individual subject participation was approximately for the duration of 6 months.

The reference therapy used in this study was SoC for VLU. The ulcer was cleaned with sterile saline and bleeding was stopped before dressing. The ulcer was dressed according to the following regimen:
  Applied a non-adherent dressing over the ulcer which extended 0.5 inch beyond the ulcer perimeter and inflamed skin margins
  Applied a non-occlusive dressing such as fine mesh gauze which was either folded or rolled as a bolster
  Applied a self adherent high compression four layer elastic wrap (3M Elastic Adhesive Bandage) or a compression crepe bandage from metatarsals to tibial plateau so that therapeutic compression is applied to the ulcer site This was a double blind, randomized, prospective, parallel group, multi-center Phase II study conducted at 10 centers in India to evaluate the efficacy and safety of Granexin™ Gel in the treatment of VLU. The total duration of the study was 11 months, including 5 months enrollment period and 6 months for study procedures. The study duration for individual subjects was 6 months which included 18 visits. A total of 101 subjects with VLU were screened for this study, 5 were found to be screen failures, and 4 subjects did not initiate participation in the study. A total of 92 subjects enrolled in the study had mean wound duration of 68.4 weeks at Screening and mean wound area of 353.64 mm$^2$ at Baseline. These subjects were randomized to receive Granexin™ Gel plus SoC or SoC alone for the treatment of VLU. Of these, 70 completed the study and 22 subjects did not complete the study due to not meeting exclusion criterion number 1, consent withdrawal, loss to follow-up, non-compliance, or SAE. Of 92 enrolled subjects, 15 subjects met exclusion criterion 1 but were considered in the Safety and ITT population. These subjects were excluded from the mITT and PP populations. A total of 83 (90.2%) subjects were males and 9 (9.8%) were females. The mean age of the study population was 49.8 years, mean weight was 70.47 kg, mean height was 168.35 cms, and mean BMI was 24.79 kg/m$^2$.

This was a phase II, prospective, randomized, double blind, parallel group, and multi-center study conducted in India in subjects with VLU. The total study duration was 11 months. The enrollment period was 5 months and 6 months for study procedures. Study duration for individual subjects was 6 months and each subject attended a total of 18 visits, including Screening (Visit 1), Baseline, (Visit 2), Treatment (Visit 3-15), and Follow-up (Visit 16-18) visits. The study procedures were divided into 3 phases: Screening Phase (Days −7 through Day 0), Treatment Phase (Day 0 through Week 12), and Follow-up Phase (Months 4 through Month 6). Subjects were randomized to 1 of the 2 treatment groups:
  Group A: Granexin™ Gel plus SoC
  Group B: SoC only Only one ulcer per subject was considered as the target ulcer which was the largest ulcer. Each subject in the Granexin™ Gel treatment group was treated with up to 14 applications of Granexin™ Gel over the initial 12 weeks of the study period. Other than the application of Granexin™ Gel, management of ulcer was similar in both the groups.

The primary efficacy endpoint of the study was to evaluate mean percent wound closure from Baseline (Visit 2) to Week 12 (Visit 15). The non-parametric Wilcoxon Mann-Whitney U test was used to analyze mean percent reduction of wound area from Baseline to Week 12 in both the treatment groups since the data did not follow a normal distribution, as confirmed by a Shapiro-Wilk p-value <0.0001 and a non-linear Q-Q plot. Subjects treated with Granexin™ Gel plus SoC showed statistically significantly higher percent wound closure from Baseline to Week 12 compared to subjects treated with SoC alone (ITT p-value=0.0238; mITT p-value=0.0105; PP p-value=0.0073), suggesting that at Week 12, wounds treated with Granexin™ Gel plus SoC reduced in size when compared to wounds treated with SoC alone.

Mean percent wound closure at Week 4, time to complete (100% and 50%) wound closure, incidence of complete wound closure, and subject self assessment of pain were also analyzed. At Week 4, a higher percentage reduction of wound area was observed in Granexin™ Gel plus SoC group than in the SoC group and this was statistically significant (ITT p-value=0.0006; mITT p-value=0.0001; PP p-value <0.0001 Wilcoxon Mann-Whitney U test).

Subjects treated with Granexin™ Gel plus SoC achieved 100% wound closure in median duration of 6 weeks in ITT, mITT, and PP population which was significantly faster compared to the SoC group in which the median duration was 12.14 weeks in the ITT population and not achieved in both mITT and PP population during the 12 weeks of efficacy assessments (ITT p-value=0.0006; mITT p-value=0.0001; PP p-value <0.0001; log-rank test).

Subjects treated with Granexin™ Gel plus SoC achieved 50% wound closure in 2.86 weeks in ITT, mITT and PP population while subjects treated with SoC alone achieved it in 6.86 weeks in ITT population and 8 weeks in both mITT and PP population (ITT p-value=0.0002, mITT p-value <0.0001, PP p-value <0.0001). The categorical analysis of incidence of 100% and 50% wound closure at Week 12 was conducted and the subjects who had 100% and 50% wound closure were considered as responders. Overall in the ITT, mITT, and PP populations, 56.5%, 63.4%, and 74.3% of the subjects in Granexin™ Gel plus SoC group, respectively, responded to treatment with 100% wound closure as compared to 30.3% of the subjects in the SoC group. The number of responders were significantly higher in Granexin™ Gel plus SoC group than in the SoC group (ITT: p-value=0.0061; mITT p-value=0.0040; PP: p-value=0.0003; Chi-square analysis). Similarly, in the PP population, 80.0% of the subjects in Granexin™ Gel plus SoC group responded to treatment and achieved 50% wound closure as compared to 51.5% of the subjects in the SoC group. The number of responders with 50% wound closure were significantly higher in Granexin™ Gel plus SoC group than in the SoC group (p-value=0.0131; Chi-square analysis), indicating that the wounds treated with Granexin™ Gel plus SoC have higher incidences of 100% and 50% wound closure (epithelialization) than wounds treated with SoC alone.

Cox Proportional Hazard Regression Model analysis was conducted to evaluate if one or more covariates such as treatment group, wound duration, baseline wound depth, and BMI etc. were associated with the time to complete 100% or 50% wound closure. It showed that treatment group was a significant factor affecting wound closure and Granexin™ Gel plus SoC group subjects had ITT: 2.281; mITT: 2.776; PP: 3.150 times more chances of 100% wound closure and ITT: 2.247; mITT: 2.501; PP: 2.61 times more chances of 50% wound closure than the SoC group subjects.

At every visit, self assessment of intensity of pain score was completed by each subject and the scores were given in comparison to the last visit. Therefore significant change in the pain scores was not observed and there was no statistically significant difference in intensity of pain as assessed by the subject at Week 12 between the 2 treatment groups.

The findings from the present study demonstrated a good safety profile with Granexin™ Gel. Overall, 28 subjects reported 40 AEs of which 24 AEs were reported by subjects in Granexin™ Gel plus SoC group; 16 AEs were reported in the SOC group. The only 2 SAEs reported, were in the SoC group. One SAE was infarction which resulted in death, and the other SAE was Deep Vein Thrombosis. Of the 40 AEs, 35 (87.5%) recovered. None of the AEs were related to Granexin™ Gel. None of the subjects were withdrawn from the study due to an AE.

No clinically significant abnormalities in the laboratory parameters were observed in either of the treatment groups. The vital signs and ECG were normal and comparable between both the treatment groups. Anti-ACT1 peptide antibodies were not detected in the serum samples collected at Screening or at Week 12.

In conclusion, Granexin™ Gel along with SoC has shown to accelerate wound healing in subjects with VLU, making it an efficacious, safe, and well tolerated therapeutic option in the treatment of VLU.

Description of Study Visits: The description of 18 visits along with premature study discontinuation and unscheduled visits is summarized below:

Visit 1: Screening Visit (Day −7): The Screening visit was held a maximum of 7 days prior to the Baseline visit.

Visit 2: Baseline Visit (Day 0) The Baseline visit was conducted within 7 days of the Screening visit. If wound size increased or decreased by 30% on the day of randomization from Screening (exclusion criterion number 1), then the subject was considered ineligible for participation in the study. The following procedures were performed at the Baseline visit:

Visit 3-14: Treatment Visits (Day 3 through Week 11) The treatment visits were conducted at Day 3 and at Week 1, 2, 3, 4, 5, 6, 7, 8, 9, 10, and 11 after Baseline visit 1 day. The following procedures were performed at these treatment visits:

Visit 15: End of Treatment Visit (Week 12)

Visit 16-18: Follow-up Visits including End of Study Visit (Month 4 through 6): The Follow-up visits were conducted at Month 4±3 days, Month 5±3 days, and Month 6±3 days (End of Study [EOS] visit). The following procedures were performed at this visit:

Standard of Care Treatment

The SoC was followed in both treatment groups. The ulcer was cleaned with sterile saline and bleeding was stopped before dressing. The ulcer was dressed according to the following regimen:

Applied a non-adherent dressing over the ulcer which extended 0.5 inch beyond the ulcer perimeter and inflamed skin margins Applied a non-occlusive dressing such as fine mesh gauze which was either folded or rolled as a bolster Applied a self adherent high compression four layer elastic wrap (3M Elastic Adhesive Bandage) or a compression crepe bandage from metatarsals to tibial plateau so that therapeutic compression is applied to the ulcer site In the Granexin™ Gel plus SoC group, the SoC as mentioned above was followed along with the application of Granexin™ Gel. The ulcer was cleaned with sterile saline and bleeding was stopped before applying the Granexin™ Gel on Days 0 and 3, and Weeks 1, 2, 3, 4, 5, 6, 7, 8, 9, 10, 11, and 12. The Granexin™ Gel was dispensed directly from its 5 ml glass vial(s) to completely cover the wound bed. With a clean sterile cotton swab, sterile tongue depressor, or a similar application aid, the Granexin™ Gel was evenly spread over the wound surface.

Granexin™ Gel is a topical gel with the active drug substance Alpha-Connexin C-terminal peptide 1 (ACT1) peptide developed at FirstString Research for the management of wounds. ACT1 is a synthetic peptide (25 amino acid) designed to mimic the Carboxy (C)-terminus of the ubiquitous transmembrane gap junction protein Connexin 43 (Cx43), with high binding specificity to zona occludens, a cytoplasmic tight junction protein. While the mechanism of action of ACT1 has not been completely elucidated, the peptide is soluble and engineered to directly translocate within cells. ACT1 peptide interacts with a known binding partner of Cx43—the Postsynaptic Density 95/Discs Large/Zonula Occludens (PDZ)-2 domain of Zonula Occludens-1 (ZO-1). The binding of the peptide to specific Cx43 C-terminus interaction domains such as PDZ-2 on ZO-1 serves to competitively inhibit its association with the Cx43 C-terminus. Connexins are gap junction proteins where as ZO-1 is a tight junction associated protein. The binding of the 25 amino acid ACT1 peptide to the PDZ-2 domain of ZO-1 serves to stabilize gap junctions as well as tight junctions [12]. This junctional stability has been associated with faster healing and reduced scarring. In addition, the low molecular weight of 25 amino acid peptide is expected to reduce the risk of an immunogenic response.

Granexin™ Gel is also designed to provide a localized protective barrier against microbial colonization and a moist environment to promote natural autolytic debridement of necrotic tissue surrounding the wound. The lot number of Granexin™ Gel used in this study was DP 1493.

Central block randomization (Block size of 2) list was prepared by MNI independent Biostatistician using a validated computer program (Statistical Analysis Software [SAS] 9.1.3). Subjects were randomized 1:1 to either Group A (Granexin™ Gel plus SoC) or Group B (SoC only). Randomization was further stratified by wound size (<10 $cm^2$ and >10 $cm^2$) to avoid bias of undue number of subjects with small or large wounds going into one arm of the study.

Interactive web response system (IWRS) was used for treatment group assignment of the eligible subjects. Being the double-blinded study, an unblinded coordinator designated by the Investigator received the assigned treatment through IWRS.

Two studies, including a preclinical and clinical study tested the efficacy and safety of 100 μM concentration of ACT1 formulated in Granexin™ Gel. In the preclinical study, the efficacy of Granexin™ Gel in wound healing was assessed on 5 mm diameter full thickness excisional wounds in adult mice and pigs. Wounds treated with 10 μM of ACT1 peptide closed faster, appeared less swollen, inflamed and healed with a smoother and less discolored appearance as compared to the wounds applied with the vehicle control. Subsequently, a Phase I, double blind, single-center, controlled study was conducted to evaluate the safety and tolerability of 20, 50, 100, and 200 μM concentrations of ACT1 formulated in Granexin™ Gel versus placebo in 48 healthy subjects following punch biopsy. The results showed Granexin™ Gel (ACT1) at each concentration to be safe and well tolerated with no evidence of localized or systemic AEs or Serious Adverse Events (SAEs). Based on preclinical studies and Phase I clinical trial, Granexin™ Gel with 100 μM concentration of the ACT1 peptide was chosen for Phase II evaluation in the treatment of VLUs.

For each subject, Granexin™ Gel (100 μM ACT1 peptide) was applied at Days 0 and 3, and Weeks 1, 2, 3, 4, 5, 6, 7, 8, 9, 10, 11, and 12.

A total of 101 subjects with VLU were screened. Of these, 5 (4.9%) were screen failures and 4 (4.04%) subjects fulfilled the inclusion/exclusion criteria but did not come for the Baseline visit. The remaining 92 (91.1%) subjects were enrolled and randomized in the study. A total of 15(16.3%) subjects met exclusion criteria number 1 or did not have adequate evaluable wound photographic data post randomization and were excluded from the mITT and PP population.

A total of 70(76.10%) subjects completed the study and the remaining 22 (23.90%) subjects did not complete the study of which 14 (63.6%) withdrew their consent, 4(18.2%) showed protocol non-compliance, 3 (13.6%) were lost to follow up, and 1 (4.5) subject (Subject 1115; SoC group) reported death due to Myocardial infarction (Table 30.

TABLE 30

Disposition of Subjects

| Category | Granexin ™ Gel plus SoC (N = 46) | SoC (N = 46) | Overall (N = 92) |
|---|---|---|---|
| Population, n (%) [1] | | | |
| Screened | | | 101 |
| Randomized | 46 (100.0%) | 46 (100.0%) | 92 (100.0%) |
| Intent-to-treat | 46 (100.0%) | 46 (100.0%) | 92 (100.0%) |
| Modified Intent-to-treat | 41 (89.1%) | 36 (78.3%) | 77 (83.7%) |
| Per-Protocol | 35 (76.1%) | 33 (71.7%) | 68 (73.9%) |
| Safety | 46 (100.0%) | 46 (100.0%) | 92 (100.0%) |
| Total number of subjects completed the study | 34 (73.9%) | 36 (78.3%) | 70 (76.1%) |
| Total number of subjects not completed the study | 12 (26.1%) | 10 (21.7%) | 22 (23.9%) |
| Reason for discontinuation | | | |
| Consent Withdrawn | 10 (83.3%) | 4 (40.0%) | 14 (63.6%) |
| Death | 0 (0.0%) | 1 (10.0%) | 1 (4.5%) |
| Lost to follow up | 2 (16.7%) | 1 (10.0%) | 3 (13.6%) |
| Protocol non-compliance | 0 (0.0%) | 4 (40.0%) | 4 (18.2%) |

Note:
[1] Percentage was calculated taking respective column header group count as denominator.

The following data sets were analyzed:
ITT Population: The ITT population included all subjects randomized to any treatment group, received at least one dose of study medication or reference treatment, and performed study assessments within and/or outside the time window specified in the protocol.
mITT Population: The mITT population excluded all subjects that met exclusion criterion 1 or did not have adequate evaluable wound photographic data post randomization
PP Analysis Population: The PP analysis population was redefined to include subjects who did not have any major protocol violation.
Safety Population: The safety population included all subjects who were randomized to either of the treatment groups in the study.
The ITT population included 92 subjects; the mITT population included 77 subjects, PP population included 68 subjects; and the safety population included 92 subjects.
Modified Intent-to-Treat Population: The following subjects were excluded from the mITT population:

Granexin™ Gel plus SoC group: Subject 304, Subject 501, Subject 503, Subject 505, and Subject 906
SoC group: Subject 103, Subject 104, Subject 1004, Subject 1006, Subject 1008, Subject 1017, Subject 1022, Subject 1026, Subject 1027, and Subject 1031

Per Protocol Population: The following subjects were excluded from the PP population:

Meeting exclusion criterion—Decrease or increase in the ulcer size by 30% or more during 7 day screening period or did not have adequate evaluable wound photographic data post randomization (15 subjects)
Granexin™ Gel plus SoC group: Subject 304, Subject 501, Subject 503, Subject 505, and Subject 906
SoC group: Subject 103, Subject 104, Subject 1004, Subject 1006, Subject 1008, Subject 1017, Subject 1022, Subject 1026, Subject 1027, and Subject 1031
Wound photograph data not available (9 subjects)
Granexin™ Gel plus SoC group: Subject 303, Subject 904, Subject 908, Subject 914, Subject 917, and subject 1102
SoC group: Subject 502, Subject 1109, and Subject 1116

Demographics and Baseline Characteristics

Of 92 enrolled subjects, 83 (90.2%) were males and 9 (9.8%) were females. The mean SD age was 49.8±12.71 years, weight was 70.47±14.89 kg, height 168.35±7.19 cm, and BMI was 24.79±4.55 kg/m², respectively. Ten (10.9%) subjects had a smoking habit with the mean SD number of cigarettes smoked per day as 8.8±7.33.

TABLE 31

Summary of Subject Demographics at Screening

| Statistics/Category, n (%)[1] | Granexin ™ Gel plus SoC (N = 46) | SoC (N = 46) | Overall (N = 92) |
|---|---|---|---|
| Age (years)[2] | | | |
| n | 46 | 46 | 92 |
| Mean | 48.2 | 51.5 | 49.8 |
| SD | 12.47 | 12.87 | 12.71 |
| Median | 48.0 | 53.0 | 51.0 |
| Range (Min.:Max.) | (18:71) | (22:79) | (18:79) |
| Gender | | | |
| Male | 44 (95.7) | 39 (84.8) | 83 (90.2%) |
| Female | 2 (4.3) | 7 (15.2) | 9 (9.8%) |
| Weight (kg)[3] | | | |
| n | 46 | 46 | 92 |
| Mean | 72.15 | 68.79 | 70.47 |
| SD | 15.014 | 14.739 | 14.891 |
| Median | 69.40 | 67.60 | 69.00 |
| Range (Min.:Max.) | (48.0:118.0) | (40.6:110.0) | (40.6:118.0) |
| Height (cm)[4] | | | |
| n | 46 | 46 | 92 |
| Mean | 169.38 | 167.32 | 168.35 |
| SD | 5.918 | 8.223 | 7.199 |
| Median | 171.00 | 168.00 | 169.85 |
| Range (Min.:Max.) | (156.0:180.0) | (148.0:186.2) | (148.0:186.2) |
| Body Mass Index (kg/m²)[5] | | | |
| n | 46 | 46 | 92 |
| Mean | 25.114 | 24.478 | 24.796 |
| SD | 4.7553 | 4.3794 | 4.5572 |
| Median | 23.930 | 23.807 | 23.807 |
| Range (Min.:Max.) | (16.04:38.97) | (16.06:34.94) | (16.04:38.97) |

TABLE 31-continued

Summary of Subject Demographics at Screening

| Statistics/Category, n (%)[1] | Granexin ™ Gel plus SoC (N = 46) | SoC (N = 46) | Overall (N = 92) |
|---|---|---|---|
| Smoking Habits | | | |
| Yes | 4 (8.7) | 6 (13.0) | 10 (10.9%) |
| No | 42 (91.3) | 40 (87.0%) | 82 (89.1%) |
| If yes, | | | |
| Current | 3 (6.5) | 5 (10.9) | 8 (8.7%) |
| Past | 1 (2.2) | 1 (2.2) | 2 (2.2%) |
| Duration of Smoking (months) | | | |
| n | 4 | 6 | 10 |
| Mean | 300.0 | 345.7 | 327.4 |
| SD | 48.99 | 53.52 | 54.29 |
| Median | 300.0 | 330.0 | 300.0 |
| Range (Min.:Max.) | (240:360) | (300:420) | (240:420) |
| Missing | 0 | 0 | 0 |
| No. of Cigarettes Smoked per day | | | |
| n | 3 | 5 | 8 |
| Mean | 8.8 | 8.8 | 8.8 |
| SD | 9.67 | 6.87 | 7.33 |
| Median | 3.5 | 6.0 | 6.0 |
| Range (Min.:Max.) | (3:20) | (2:20) | (2:20) |
| Missing | 1 | 1 | 2 |

Note: [1]Percentages are calculated taking respective column header group count as denominator.
[2]Calculated age as: Age = [(Informed consent signed Date (Screening) - Date of Birth+1)/365.25].
[3]Calculated Weight as: lbs/2.2 = kilograms. [4]Calculated Height as: (Height (cms) = Height in inches * 2.538).
[5]Calculated BMI as :{Weight (kg)/(Height (m))$^2$}.

Ulcer Identification History

Thirty (32.60%) subjects reported wound location on medial side of leg followed by 20 (21.7%) subjects each reporting on anterior side of leg and lateral side of leg. The overall mean±SD duration of wound history was 68.4±149.65 weeks and mean wound area was 353.64±367.196 mm$^2$, respectively (Table 32).

TABLE 32

Summary of Ulcer Identification History

| Statistics/Category, n (%)[1] | Granexin ™ Gel plus SoC (n = 46) | SoC (n = 46) | Overall (N = 92) |
|---|---|---|---|
| Wound Location | | | |
| Anteromedial | 0(0.0) | 1(2.2) | 1(1.1) |
| Anterior side of leg | 11(23.9) | 9(19.6) | 20(21.7) |
| Lateral Malleolus | 2(4.3) | 6(13.0) | 8(8.7) |
| Lateral Side of leg | 12(26.1) | 8(17.4) | 20(21.7) |
| Medial Malleolus | 3(6.5) | 5(10.9) | 8(8.7) |
| Medial side of leg | 17(37.0) | 13(28.3) | 30(32.6) |
| Posterior side of leg | 1(2.2) | 4(8.7) | 5(5.4) |
| Duration of Wound History (weeks) | | | |
| n | 46 | 46 | 92 |
| Mean | 62.7 | 74.0 | 68.4 |
| SD | 119.46 | 175.92 | 149.65 |
| Median | 16.0 | 16.0 | 16.0 |
| Range (Min.:Max.) | (4:511) | (4:788) | (4:788) |
| Wound Area (mm$^2$) (Length*Width) | | | |
| n | 41 | 43 | 84 |
| Mean | 347.47 | 359.51 | 353.64 |
| SD | 369.266 | 369.484 | 367.196 |
| Median | 236.43 | 233.43 | 234.93 |
| Range (Min.:Max.) | (19.0:1804.9) | (0.0:1576.8) | (0.0:1804.9) |

Note:
[1]Percentages are calculated taking respective column header group count as denominator.

Primary Efficacy Endpoint: Mean Percent Wound Closure from Baseline to Week 12

Table 33 summarizes the parametric analysis of the mean percent reduction of wound area (in mm$^2$) from Baseline to Week 12 in the ITT population. Of the 92 subjects in the ITT population, non-missing observations from Baseline to Week 12 for percent reduction of wound area were available for 62 subjects. The mean percent±SD reduction of wound area from Baseline to Week 12 was not statistically significantly higher in Granexin™ Gel plus SoC group than SoC group (Granexin™ Gel plus SoC group: 79.280%±50.37; SoC group: 36.2800±179.78; p-value=0.0741) as per parametric analysis. Similar results were obtained after sensitivity analysis (p-value=0.0921). The model factors such as treatment, visit, treatment*visit, and ankle circumference were significantly related to the mean percent reduction in wound area from Baseline to Week 12 for the ITT population (Treatment: p-value=0.0062; Visit: p-value <0.0001; Treatment*Visit p-value=0.0139; Ankle Circumference: p-value=0.0200).

FIG. 10 displays the longitudinal response profile of the mean percent reduction of wound area at all visits by treatment group of the ITT population.

TABLE 33

Mean Percent Reduction of Wound Area (mm$^2$) from Baseline to Week 12 (Parametric analysis) ITT Population (N = 92)

| Statistics | Granexin ™ Gel plus SoC (N = 46) | SoC (N = 46) |
|---|---|---|
| Total number of subjects evaluated | N = 62[1] | |
| Percent reduction of wound area from Baseline to Week 12 (mm$^2$) | | |
| n | 34 | 28 |
| Mean | 79.279 | 36.282 |
| SD | 50.3695 | 179.7788 |
| Median | 100.000 | 93.320 |
| Range (Min.:Max.) | (−68.85:100.00) | (−849.50:100.00) |
| LS Mean Estimate | 73.2182 | 53.0164 |
| Difference Estimate[2] | 20.2018 | |
| SE[3] | 11.2336 | |

TABLE 33-continued

Mean Percent Reduction of Wound Area (mm$^2$) from Baseline to Week 12 (Parametric analysis) ITT Population (N = 92)

| Statistics | Treatment Group | |
|---|---|---|
| | Granexin™ Gel plus SoC (N = 46) | SoC (N = 46) |
| 95% CI (L:U.) | (−1.99:42.39) | |
| p-value[4],[5] | 0.0741 | |
| Model factor[4][5] p-value | | |
| Treatment | 0.0062 | |
| Visit | <0.0001 | |
| Treatment*Visit | 0.0139 | |
| Exudate level | 0.1440 | |
| Viable tissue | 0.6703 | |
| Strata | 0.1532 | |
| Ankle circumference | 0.0200 | |
| Wound duration | 0.5371 | |
| BMI | 0.7303 | |

Note:
[1]"Total no. of subjects evaluated" represented subjects having non-missing observations for change from Baseline to Week 12 for percent reduction of wound area
[2]Difference estimate for Granexin™ Gel plus SoC indicated (GranexinTM Gel plus SoC) - SoC).
[3]SE of Granexin™ Gel plus SoC indicated Standard Error of Differences (Granexin™ Gel plus SoC)- SoC).
[4]p-value for Granexin™ Gel plus SoC indicated significance of treatment differences (Granexin™ Gel plus SoC) - (SoC).
[5]ANCOVA mixed model with repeated measures was used to compare average percent reduction in wound area with treatment,visit and treatment*visit as factors and strata, wound duration,viable tissue, exudate level and the BMI as covariates using PROC Mixed procedure of SAS software.

Table 34 summarizes the parametric analysis of the mean percent reduction of wound area (in mm$^2$) from Baseline to Week 12 in the mITT population. Of the 77 subjects in the mITT population, non-missing observations from Baseline to Week 12 for percent reduction of wound area were available for 59 subjects. The mean percent±SD reduction of wound area from Baseline to Week 12 was not statistically significantly higher in Granexin™ Gel plus SoC group than SoC group (Granexin™ Gel plus SoC group: 78.960%±51.11; SoC group: 31.380%±185.89; p-value=0.0643) as per parametric analysis. Similar results were obtained after sensitivity analysis (p-value=0.0785). The model factors such as treatment, visit, treatment*visit, and ankle circumference were significantly related to the mean percent reduction in wound area from Baseline to Week 12 for the mITT population (Treatment: p-value=0.0028; Visit: p-value <0.0001; Treatment*Visit p-value=0.0424; Ankle Circumference: p-value=0.0428).

FIG. 11 displays the longitudinal response profile of the mean percent reduction of wound area at all visits by treatment group of the mITT population.

TABLE 34

Mean Percent Reduction of Wound Area (mm$^2$) from Baseline to Week 12 (Parametric analysis) mITT Population (N = 77)

| Statistics | Treatment Group | |
|---|---|---|
| | Granexin™ Gel plus SoC (N = 41) | SoC (N = 36) |
| Total number of subjects evaluated | N = 59[1] | |
| Percent reduction of wound area from Baseline to Week 12 (mm$^2$) | | |
| n | 33 | 26 |
| Mean | 78.957 | 31.380 |
| SD | 51.1148 | 185.8931 |
| Median | 100.000 | 87.352 |

TABLE 34-continued

Mean Percent Reduction of Wound Area (mm$^2$) from Baseline to Week 12 (Parametric analysis) mITT Population (N = 77)

| Statistics | Treatment Group | |
|---|---|---|
| | Granexin™ Gel plus SoC (N = 41) | SoC (N = 36) |
| Range (Min.:Max.) | (−68.85:100.00) | (−849.50:100.00) |
| LS Mean Estimate | 73.275 | 51.921 |
| Difference Estimate[2] | 21.3543 | |
| SE[3] | 11.4565 | |
| 95% CI (L:U.) | (−1.28:43.99) | |
| p-value[4], [5] | 0.0643 | |
| Model factor[4] [5] p-value | | |
| Treatment | 0.0028 | |
| Visit | <.0001 | |
| Treatment*Visit | 0.0424 | |
| Exudate level | 0.1232 | |
| Viable tissue | 0.7318 | |
| Strata | 0.1592 | |
| Ankle circumference | 0.0428 | |
| Wound duration | 0.5846 | |
| BMI | 0.6308 | |

Note:
[1]"Total no. of subjects evaluated" represented subjects having non-missing observations for change from Baseline to Week 12 for percent reduction of wound area
[2]Difference estimate for Granexin™ Gel plus SoC indicated (Granexin™ Gel plus SoC) - SoC).
[3]SE of Granexin™ Gel plus SoC indicated Standard Error of Differences (Granexin™ Gel plus SoC)- SoC).
[4]p-value Granexin™ Gel plus SoC indicated significance of treatment differences (Granexin™ Gel plus SoC) - (SoC).
[5]ANCOVA mixed model with repeated measures was used to compare average percent reduction in wound area with treatment, visit and treatment*visit as factors and strata, wound duration,viable tissue, exudate level and the BMI as covariates using PROC Mixed procedure of SAS software.

The parametric analysis of the mean percent reduction of wound area (in mm$^2$) from Baseline to Week 12 in the PP population is summarized in Table 35 Of the 68 subjects in the PP population, non-missing observations for percent reduction of wound area from Baseline to Week 12 were available for 58 subjects. The mean percent±SD reduction of wound area from Baseline to Week 12 was not statistically significantly higher in Granexin™ Gel plus SoC group than in SoC group (Granexin™ Gel plus SoC group: 78.960%±51.11; SoC group: 28.630%±189.18) (p-value=0.0722) as per parametric analysis. Similarly, on applying LOCF approach for imputation of missing values, results obtained after sensitivity analysis, were not statistically significant (p-value=0.1151. The model factors such as treatment, visit, treatment*visit, and ankle circumference were significantly related to the mean percent reduction in wound area from Baseline to Week 12 for the PP population (Treatment: p-value=0.0025; Visit: p-value <0.0001; Treatment*visit p-value=0.0228; and Ankle Circumference p-value=0.0350). FIG. 12 displays the longitudinal response profile of the mean percentage reduction of wound area at all visits by treatment group of the PP population.

TABLE 35

Mean Percent Reduction of Wound Area (mm$^2$) from Baseline to Week 12 (Parametric analysis) PP Population (N = 68)

| Statistics | Treatment Group | |
|---|---|---|
| | Granexin™ Gel plus SoC (N = 35) | SoC (N = 33) |
| Total no. of subjects evaluated | N = 58[1] | |
| Percent reduction of wound area from Baseline to Week 12 | | |
| n | 33 | 25 |
| Mean | 78.957 | 28.635 |

TABLE 35-continued

Mean Percent Reduction of Wound Area (mm$^2$) from Baseline to Week 12 (Parametric analysis) PP Population (N = 68)

| Statistics | Treatment Group | |
|---|---|---|
| | Granexin ™ Gel plus SoC (N = 35) | SoC (N = 33) |
| SD | 51.1148 | 189.1879 |
| Median | 100.000 | 85.225 |
| Range (Min.:Max.) | (−68.85:100.00) | (−849.50:100.00) |
| LS mean estimate | 74.5294 | 53.5060 |
| Difference estimate[2] | 21.0234 | |
| SE[3] | 11.6048 | |
| 95% CI (L.:U.) | (−1.92:43.97) | |
| p-value[4],[5] | 0.0722 | |
| Model factor[3][4] p-value | | |
| Treatment | 0.0025 | |
| Visit | <0.0001 | |
| Treatment*Visit | 0.0228 | |
| Exudate level | 0.1306 | |
| Viable tissue | 0.7206 | |
| Strata | 0.2849 | |
| Ankle circumference | 0.0350 | |
| Wound duration | 0.5391 | |
| Body mass index | 0.5793 | |

Note:
[1]"Total no. of subjects evaluated" represented subjects having non-missing observations for dependent variable
[2]Difference estimate for Granexin ™ Gel plus SoC indicated (Granexin ™ Gel plus SoC) − SoC).
[3]SE of Granexin ™ Gel plus Standard of Care indicated Standard Error of Differences (Granexin ™ Gel plus SoC) − SoC).
[4]p-value for Granexin ™ Gel plus SoC indicated significance of treatment differences (Granexin ™ Gel plus SoC) − (SoC).
[5]ANCOVA mixed model with repeated measures was used to compare average percentage reduction in wound area with treatment,visit and treatment*visit as factors and strata, wound duration, viable tissue, exudate level and the body mass index as covariates using PROC Mixed procedure of SAS software.

To confirm the applicability of parametric statistical inference methodology in the wound reduction analysis, the data was tested to determine if it followed normal distribution. Using PROC UNIVARIATE of SAS® (version 9.1.3) Shapiro-Wilk W statistic was calculated. The p-value (<0.0001) indicated that the data did not follow a normal distribution. This was further confirmed by the Q-Q plot for both the ITT and PP populations in which the observations were not in a straight line and did not show a normal distribution. Therefore, the hypothesis of normal distribution of the data in the sample was rejected and non-parametric analysis was conducted.

Table 36 summarizes the non-parametric analysis for mean percent reduction of wound area from Baseline to Week 12 in the ITT population. The Wilcoxon Mann-Whitney U test is a non-parametric test which determines whether there is a difference in two samples of independent observations. In Granexin™ Gel plus SoC group, the actual sum of scores (1210.00) was found higher than the expected sum of scores under the null hypothesis (1071.00). In SoC group, the actual sum of scores (743.00) was found lower than the expected sum of the scores under the null hypothesis (882.00). The actual sum of scores was calculated by adding the ranks of both groups after sorting data of wound size reduction in ascending order and the expected sum of scores was calculated as the sum of scores when there is no difference between the 2 groups. Subjects in Granexin™ Gel plus SoC group had statistically significantly higher percent reduction of wound area from Baseline to Week 12 than in SoC group (p-value=0.0238).

TABLE 36

Mean Percent Reduction of Wound Area (mm$^2$) from Baseline to Week 12 (Non-parametric analysis) ITT Population (N = 92)

| Statistics | Treatment Group | |
|---|---|---|
| | Granexin ™ Gel plus SoC (N = 46) | SoC (N = 46) |
| Percent reduction of wound area from Baseline to Week 12 | | |
| Sum of score | 1210.00 | 743.00 |
| Expected under H$_o$ | 1071.00 | 882.00 |
| p-value[1] | 0.0238 | |

Note:
[1]p-value is evaluated by using non-parametric Wilcoxon Mann-Whitney U test between treatment group.
General Note:
Mean percentage reduction from Baseline = ((Baseline − week X)/Baseline) * 100
H$_o$: Null Hypothesis
If wound was healed and all further visits were missing then 100% reduction had been carried forward to missing visits.

Table 37 summarizes the non-parametric analysis for mean percent reduction of wound area from Baseline to Week 12 in the mITT population. The Wilcoxon Mann-Whitney U test is a non-parametric test which determines whether there is a difference in two samples of independent observations. In Granexin™ Gel plus SoC group, the actual sum of scores (1136.00) was found higher than the expected sum of scores under the null hypothesis (990.00). In SoC group, the actual sum of scores (634.00) was found lower than the expected sum of the scores under the null hypothesis (780.00). The actual sum of scores was calculated by adding the ranks of both groups after sorting data of wound size reduction in ascending order and the expected sum of scores was calculated as the sum of scores when there is no difference between the 2 groups. Subjects in Granexin™ Gel plus SoC group had statistically significantly higher percent reduction of wound area from Baseline to Week 12 than in SoC group (p-value=0.0105).

TABLE 37

Mean Percent Reduction of Wound Area (mm$^2$) from Baseline to Week 12 (Non-parametric analysis) mITT Population (N = 77)

| Statistics | Treatment Group | |
|---|---|---|
| | Granexin ™ Gel plus SoC (N = 41) | SoC (N = 36) |
| Percent reduction of wound area from Baseline to Week 12 | | |
| Sum of score | 1136.00 | 634.00 |
| Expected under H$_o$ | 990.00 | 780.00 |
| p-value[1] | 0.0105 | |

Note:
[1]p-value is evaluated by using non-parametric Wilcoxon Mann-Whitney U test between treatment group.
General Note:
Mean percentage reduction from Baseline = ((Baseline − week X)/Baseline)* 100
H$_o$: Null Hypothesis
If wound was healed and all further visits were missing then 100% reduction had been carried forward to missing visits.

Table 38 summarizes the non-parametric analysis for mean percent reduction of wound area from Baseline to Week 12 in the PP population. In Granexin™ Gel plus SoC group, the actual sum of scores (1123.00) was found higher than the expected sum of scores under the null hypothesis (973.50) and in SoC group, the actual sum of scores (588.00) was found lower than the expected sum of the scores under the null hypothesis (737.50). Subjects in Granexin™ Gel plus SoC group had statistically significantly higher percent reduction of wound area from Baseline to Week 12 than subjects in SoC group (p-value=0.0073).

TABLE 38

Mean Percent Reduction of Wound Area (mm²) from Baseline to Week 12 (Non-parametric analysis) PP Population (N = 68)

| Statistics | Treatment Group | |
|---|---|---|
| | Granexin ™ Gel plus SoC group (N = 35) | SoC group (N = 33) |
| Percent reduction of wound area from Baseline to Week 12 | | |
| Sum of score | 1123.00 | 588.00 |
| Expected under H$_o$ | 973.50 | 737.50 |
| p-value[1] | 0.0073 | |

Note:
[1]p-value was evaluated by using non-parametric Wilcoxon Mann-Whitney U test between treatment group.

Secondary Analysis: Mean Percentage Reduction of Wound Area from Baseline to Week 4

The parametric evaluation of mean percent wound closure from Baseline to Week 4 in the ITT population is summarized in Table 39. Of 92 subjects in the ITT population, non-missing observations for percent reduction of wound area from Baseline to Week 4 were available for a total of 56 subjects. The mean percent±SD reduction of wound area from Baseline to Week 4 was statistically significantly higher in Granexin™ Gel plus SoC group (76.99±29.74) than in SoC group (39.080±42.80) (p-value=0.0040). The model factors such as treatment, visit, and ankle circumference were significantly related to the mean percent reduction of wound area from Baseline to Week 4 in the ITT population (treatment p-value=0.0062; Visit p-value <0.0001; treatment*visit p-value=0.0139; and Ankle Circumference p-value=0.0200).

TABLE 39

Mean Percent Reduction of Wound Area (mm²) from Baseline to Week 4 (Parametric analysis) ITT Population (N = 92)

| Statistics | Treatment Group | |
|---|---|---|
| | Granexin ™ Gel plus SoC (N = 46) | SoC (N = 46) |
| Total no. of subjects evaluated | N = 56[1] | |
| Percent reduction of wound area from Baseline to Week 4 | | |
| n | 30 | 26 |
| Mean | 76.996 | 39.080 |
| SD | 29.7470 | 42.8061 |
| Median | 97.369 | 41.872 |
| Range (Min:Max.) | (0.40:100.00) | (−35.54:100.00) |
| LS mean estimate | 60.2593 | 27.0027 |
| Difference estimate [2] | 33.2566 | |
| SE[3] | 11.3883 | |
| 95% CI (L.:U.) | (10.76:55.75) | |
| p-value [4], [5] | 0.0040 | |
| Model Factor [3] [4] p-value | | |
| Treatment | 0.0062 | |
| Visit | <0.0001 | |
| Treatment*Visit | 0.0139 | |
| Exudate level | 0.1440 | |
| Viable tissue | 0.6703 | |
| Strata | 0.1532 | |
| Ankle Circumference | 0.0200 | |

TABLE 39-continued

Mean Percent Reduction of Wound Area (mm²) from Baseline to Week 4 (Parametric analysis) ITT Population (N = 92)

| Statistics | Treatment Group | |
|---|---|---|
| | Granexin ™ Gel plus SoC (N = 46) | SoC (N = 46) |
| Wound duration | 0.5371 | |
| Body mass index | 0.7303 | |

Note:
[1]"Total no. of subjects evaluated" represented subjects having non-missing observations for dependent variable
[2]Difference estimate for Granexin ™ Gel plus SoC indicated (Granexin ™ Gel plus SoC) − SoC).
[3]SE of Granexin ™ Gel plus SoC indicated Standard Error of Differences (Granexin ™ Gel plus SoC) − SoC).
[4]p-value for Granexin ™ Gel plus SoC indicated significance of treatment differences (Granexin ™ Gel plus SoC) − (SoC).
[5]ANCOVA mixed model with repeated measures was used to compare average percentage reduction in wound area with treatment, visit and treatment*visit as factors and strata, wound duration, viable tissue, exudate level and the body mass index as covariates using PROC Mixed procedure of SAS software.

The parametric evaluation of mean percent wound closure from Baseline to Week 4 in the mITT population is summarized in Table 40. Of 77 subjects in the mITT population, non-missing observations for percent reduction of wound area from Baseline to Week 4 were available for a total of 54 subjects. The mean percent SD reduction of wound area from Baseline to Week 4 was statistically significantly higher in Granexin™ Gel plus SoC group (76.99±29.74) than in SoC group (34.00±40.52) (p-value=0.0022). The model factors such as treatment, visit, and ankle circumference were significantly related to the mean percent reduction of wound area from Baseline to Week 4 in the mITT population (treatment p-value=0.0028; Visit p-value <0.0001; treatment*visit p-value=0.0424; and Ankle Circumference p-value=0.0428).

TABLE 40

Mean Percent Reduction of Wound Area (mm²) from Baseline to Week 4 (Parametric analysis) mITT Population (N = 77)

| Statistics | Treatment Group | |
|---|---|---|
| | Granexin ™ Gel plus SoC (N = 41) | SoC (N = 36) |
| Total no. of subjects evaluated | N = 54[1] | |
| Percent reduction of wound area from Baseline to Week 4 | | |
| n | 30 | 24 |
| Mean | 76.996 | 34.003 |
| SD | 29.7470 | 40.5227 |
| Median | 97.369 | 38.217 |
| Range (Min.:Max.) | (0.40:100.00) | (−35.54:100.00) |
| LS mean estimate | 60.394 | 24.421 |
| Difference estimate [2] | 35.9729 | |
| SE[3] | 11.5191 | |
| 95% CI (L.:U.) | (13.21:58.73) | |
| p-value [4], [5] | 0.0022 | |
| Model Factor [3] [4] p-value | | |
| Treatment | 0.0028 | |
| Visit | <0.0001 | |
| Treatment*Visit | 0.0424 | |
| Exudate level | 0.1232 | |

TABLE 40-continued

Mean Percent Reduction of Wound Area (mm$^2$) from Baseline to Week 4 (Parametric analysis) mITT Population (N = 77)

| | Treatment Group | |
|---|---|---|
| Statistics | Granexin™ Gel plus SoC (N = 41) | SoC (N = 36) |
| Viable tissue | 0.7318 | |
| Strata | 0.1592 | |
| Ankle Circumference | 0.0428 | |
| Wound duration | 0.5846 | |
| Body mass index | 0.6308 | |

Note:
[1]"Total no. of subjects evaluated" represented subjects having non-missing obervations for dependent variable
[2]Difference estimate for Granexin™ Gel plus SoC inidcated (Granexin™ Gel plus SoC) – SoC).
[3]SE of Granexin™ Gel plus SoC inidcated Standard Error of Differences (Granexin™ Gel plus SoC) – SoC).
[4]p-value for Granexin™ Gel plus SoC indicated significance of treatment differences (Granexin™ Gel plus SoC) – (SoC)
[5]ANCOVA mixed model with repeated measures was used to compare average percentage reduction in wound area with treatment,visit and treatment*visit as factors and strata, wound duration, viable tissue, exudate level and the body mass index as covariates using PROC Mixed procedure of SAS software.

The parametric analysis of mean percentage reduction of wound area from Baseline to Week 4 in the PP population is summarized in Table 41. Of 68 subjects in the PP population, non-missing observations for change from Baseline to Week 4 for percent reduction of wound area were available for a total of 53 subjects. The mean percent SD reduction of wound area (mm$^2$) from Baseline to Week 4 was statistically significantly higher in Granexin™ Gel plus SoC group subjects (76.99±29.74) than in SoC group subjects (31.13±38.86) (p-value=0.0012). The model factors such as treatment, visit, treatment*visit, and ankle circumference were significantly related to the mean percent reduction of wound area from Baseline to Week 4 in the PP population (treatment p-value=0.0025; Visit p-value <0.0001; treatment*visit p-value=0.0228; and Ankle Circumference p-value=0.0350).

TABLE 41

Mean Percent Reduction of Wound Area (mm$^2$) from Baseline to Week 4 (Parametric analysis) PP Population (N = 68)

| | Treatment Group | |
|---|---|---|
| Statistics | Granexin™ Gel plus SoC (N = 35) | SoC (N = 33) |
| Total no. of subjects evaluated | N = 53[1] | |
| Percent reduction of wound area from Baseline to Week 4 | | |
| n | 30 | 23 |
| Mean | 76.996 | 31.134 |
| SD | 29.7470 | 38.8605 |
| Median | 97.369 | 34.902 |
| Range (Min.:Max.) | (0.40:100.00) | (−35.54:100.00) |
| LS Mean Estimate | 62.3396 | 23.8304 |
| Difference Estimate [2] | 38.5092 | |
| SE [3] | 11.6027 | |
| 95% CI (L.:U.) | (15.56:61.46) | |
| p-value [4], [5] | 0.0012 | |
| Model Factor[3] [4] p-value | | |
| Treatment | 0.0025 | |
| Visit | <0.0001 | |
| Treatment* Visit | 0.0228 | |
| Exudate level | 0.1306 | |
| Viable tissue | 0.7206 | |
| Strata | 0.2849 | |

TABLE 41-continued

Mean Percent Reduction of Wound Area (mm$^2$) from Baseline to Week 4 (Parametric analysis) PP Population (N = 68)

| | Treatment Group | |
|---|---|---|
| Statistics | Granexin™ Gel plus SoC (N = 35) | SoC (N = 33) |
| Ankle circumference | 0.0350 | |
| Wound duration | 0.5391 | |
| Body mass index | 0.5793 | |

Note:
[1]"Total no. of subjects evaluated" represented subjects having non-missing observations for dependent variable
[2]Difference estimate for Granexin™ Gel plus SoC indicated (Granexin™ Gel plus SoC) – SoC).
[3]SE of Granexin™ Gel plus SoC indicated Standard Error of Differences (Granexin™ Gel plus SoC) – SoC).
[4]p-value for Granexin™ Gel plus SoC indicated significance of treatment differences (Granexin™ Gel plus SoC) – (SoC).
[5]ANCOVA mixed model with repeated measures was used to compare average percentage reduction in wound area with treatment, visit and treatment*visit as factors and strata, wound duration, viable tissue, exudate level and the body mass index as covariates using PROC Mixed procedure of SAS software.

Table 42 summarizes the non-parametric analysis for mean percent reduction of wound area from Baseline to Week 4 in the ITT population. In Granexin™ Gel plus SoC group, the actual sum of scores (1060.00) was found higher than the expected sum of scores under the null hypothesis (855.00). In SoC group, the actual sum of scores (536.00) was found lower than the expected sum of the scores under the null hypothesis (741.00). Granexin™ Gel plus SoC group subjects had statistically significantly higher percent reduction of wound area than SoC group subjects from Baseline to Week 4 (p-value=0.0006).

TABLE 42

Mean Percent Reduction of Wound Area (mm$^2$) from Baseline to Week 4 (Non-parametric analysis) ITT Population (N = 92)

| | Treatment Group | |
|---|---|---|
| Statistics | Granexin™ Gel plus SoC (N = 46) | SoC (N = 46) |
| Percent reduction of wound area from Baseline to Week 4 | | |
| Sum of score | 1060.00 | 536.00 |
| Expected under H$_o$ | 855.00 | 741.00 |
| p-value[1] | 0.0006 | |

Note:
[1]p-value is evaluated by using non-parametric Wilcoxon Mann-Whitney U test between treatment group.

Table 43 summarizes the non-parametric analysis for mean percent reduction of wound area from Baseline to Week 4 in the mITT population. In Granexin™ Gel plus SoC group, the actual sum of scores (1046.00) was found higher than the expected sum of scores under the null hypothesis (825.00). In SoC group, the actual sum of scores (439.00) was found lower than the expected sum of the scores under the null hypothesis (660.00). Granexin™ Gel plus SoC group subjects had statistically significantly higher percent reduction of wound area than SoC group subjects from Baseline to Week 4 (p-value=0.0001).

TABLE 43

Mean Percent Reduction of Wound Area (mm$^2$) from Baseline to Week 4 (Non-parametric analysis) mITT Population (N = 77)

| | Treatment Group | |
|---|---|---|
| Statistics | Granexin ™ Gel plus SoC (N = 41) | SoC (N = 36) |
| Percent reduction of wound area from Baseline to Week 4 | | |
| Sum of score | 1046.00 | 439.00 |
| Expected under H$_o$ | 825.00 | 660.00 |
| p-value[1] | 0.0001 | |

Note:
[1] p-value is evaluated by using non-parametric Wilcoxon Mann-Whitney U test between treatment group.

The non parametric analysis for mean percent reduction of wound area from Baseline to Week 4 in the PP population is summarized in Table 44. In Granexin™ Gel plus SoC group, the actual sum of scores (1039.00) was found higher than the expected sum of scores under the null hypothesis (810.00). In SoC group, the actual sum of scores (392.00) was found lower than the expected sum of the scores under the null hypothesis (621.00). Granexin™ Gel plus SoC group subjects had statistically significantly higher percent reduction of wound area than SoC group subjects from Baseline to Week 4 (p-value <0.0001).

TABLE 44

Mean Percent Reduction of Wound Area (mm$^2$) from Baseline to Week 4 (Non-parametric analysis) PP Population (N = 68)

| | Treatment Group | |
|---|---|---|
| Statistics | Granexin ™ Gel plus SoC (N = 35) | SoC (N = 33) |
| Percent reduction of wound area from Baseline to Week 4 | | |
| Sum of score | 1039.00 | 392.00 |
| Expected under H$_o$ | 810.00 | 621.00 |
| p-value[1] | <0.0001 | |

Note:
[1] p-value is evaluated by using non-parametric Wilcoxon Mann-Whitney U test between treatment group.

Time to 100% Wound Closure: Time taken for first complete (100%) wound closure for the ITT population is summarized in Table 45 and FIG. 13 Complete wound closure was defined as 100% epithelialization of the wound and absence of any drainage from the wound. Out of 92 subjects, 28 [60.9%] subjects in the Granexin™ Gel plus SoC group and 15 (32.6%) subjects in the SoC group had 100% wound closure by Week 12. The median duration of 100% wound closure was 6 weeks (90% CI: 4 to 8 weeks) in Granexin™ Gel plus SoC group and 12.14 weeks (900% CI: 10.14 to not achieved) in SoC group. Subjects in Granexin™ Gel plus SoC group took statistically significantly less time to achieve 100% wound closure than SoC group subjects (p-value=0.0006). Five subjects (Granexin™ Gel plus SoC group: 4; SoC group: 1) having missing value after Screening or having missing visit date were not included in the analysis. The remaining 44 subjects (Granexin™ Gel plus SoC group: 14 [30.4%]; SoC group: 30 [65.20%]) were censored due to reasons such as subjects not having complete wound closure, lack of photographic evaluation data, withdrawal of consent, loss to follow-up, discontinued due to protocol non compliance, or death.

TABLE 45

Summary of Time to First Complete (100%) Wound Closure by Week 12 ITT Population (N = 92)

| | Treatment Group | |
|---|---|---|
| Statistics[1] | Granexin ™ Gel plus SoC (N = 46) | SoC (N = 46) |
| Number (%) of subjects with complete (100%) wound closure | 28(60.9%) | 15(32.6%) |
| Number (%) of censored subjects | 14(30.4%) | 30(65.2%) |
| Median duration (weeks) of complete wound closure(90% CI)[2] | 6.00(4.00; 8.00) | 12.14(10.14; NA) |
| p-value[3] | 0.0006 | |

Note:
[1] Percentage was calculated taking count of corresponding treatment groups as denominator.
[2] The median duration of complete wound closure was estimated by Kaplan-Meier method and also 90% CI was calculated for the median duration of 100% wound closure.
[3] p-value was calculated using log-rank test for treatment groups using Proc Lifetest procedure of SAS software.

Time taken for first complete (100%) wound closure for the mITT population is summarized in Table 46 and FIG. 14 Complete wound closure was defined as 100% epithelialization of the wound and absence of any drainage from the wound. Out of 77 subjects, 28 (68.3%) subjects in the Granexin™ Gel plus SoC group and 15 (36.1%) subjects in the SoC group had 100% wound closure by Week 12. The median duration of 100% wound closure was 6 weeks (90% CI: 4 to 7 weeks) in Granexin™ Gel plus SoC group and not achieved (90% CI: 12 to not achieved) in SoC group. Subjects in Granexin™ Gel plus SoC group took statistically significantly less time to achieve 100% wound closure than SoC group subjects (p-value <0.0001). Five subjects (Granexin™ Gel plus SoC group: 4; SoC group: 1) having missing value after Screening or having missing visit date were not included in the analysis. The remaining 34 subjects (Granexin™ Gel plus SoC group: 11 (26.8%); SoC group: 23 (63.9%) were censored due to reasons such as subjects not having complete wound closure, lack of photographic evaluation data, withdrawal of consent, loss to follow-up, discontinued due to protocol non compliance, or death.

TABLE 46

Summary of Time to First Complete (100%) Wound Closure by Week 12 mITT Population (N = 77)

| | Treatment Group | |
|---|---|---|
| Statistics[1] | Granexin ™ Gel plus SoC (N = 41) | SoC (N = 36) |
| Number (%) of subjects with complete (100%) wound closure | 28(68.3 %) | 13(36.1 %) |
| Number (%) of censored subjects | 11(26.8%) | 23(63.9%) |
| Median duration (weeks) of complete wound closure(90% CI)[2] | 6.00(4.00; 7.00) | NA(12.00; NA)[3] |
| p-value[4] | <0.0001 | |

Note:
[1] Percentage was calculated taking count of corresponding treatment groups as denominator.
[2] The median duration of complete wound closure was estimated by Kaplan-Meier method and also 90 % CI was calculated for the median duration of 100 % wound closure.
[3] NA: Not achieved
[4] p-value was calculated using log-rank test for treatment groups using Proc Lifetest procedure of SAS software.

Time taken for 100% wound closure in the PP population is summarized in Table 47 and FIG. 15. Out of 68 subjects, 40(Granexin™ Gel plus SoC group: 28 [80.0%]; SoC group: 12 [36.4%]) had 100% wound closure by Week 12. The median duration of 100% wound closure was 6 weeks (90% CI was 4 to 7 weeks) in Granexin™ Gel plus SoC group and median duration was not achieved (90% CI: 12.00 to NA) in 12 weeks of treatment evaluation in SoC group. Subjects in Granexin™ Gel plus SoC group took statistically significantly less time to achieve 100% wound closure than SoC group subjects (p-value <0.0001). A total of 28 subjects (Granexin™ Gel plus SoC group: 7 [20.0%]; SoC: 21(63.6%]) were censored due to reasons such as subjects not having complete wound 100% closure, lack of photographic evaluation data, withdrawal of consent, loss to follow-up, discontinued due to protocol non compliance, or death.

TABLE 47

Summary of Time to First Complete (100%) Wound Closure by Week 12 PP Population (N = 68)

| Statistics[1] | Treatment Group | |
| --- | --- | --- |
| | Granexin ™ Gel plus SoC (N = 35) | SoC (N = 33) |
| Number (%) of subjects with complete (100%) wound closure | 28(80.0%) | 12(36.4%) |
| Number (%) of censored subjects | 7(20.0%) | 21(63.6%) |
| Median duration (weeks) of complete wound closure(90% CI)[2] | 6.00(4.00; 7.00) | NA(12.00; NA) |
| p-value[3] | <0.0001 | |

Note:
[1]Percentage was calculated taking count of corresponding treatment groups as denominator.
[2]The median duration of complete wound closure was estimated by Kaplan-Meier method and also 90% CI was calculated for the median duration of 100% wound closure.
[3]p-value was calculated using Log-rank test for treatment groups using Proc Lifetest procedure of SAS software.

Time taken to achieve 50% wound closure in the ITT population is summarized in Table 48 and FIG. 16. Out of 92 subjects, 61(Granexin™ Gel plus SoC group: 34 [73.9%]; SoC group: 25 [54.3%]) had 50% wound closure by Week 12. The median duration of 50% wound closure was 2.86 weeks (90% CI was 2.14 to 3 weeks) in Granexin™ Gel plus SoC group and 6.86 weeks (90% CI: 5.00 to 9.14) in SoC group. Subjects in Granexin™ Gel plus SoC group took statistically significantly less time to achieve 50% wound closure than SoC group subjects (p-value=0.0002). Five (5.5%) subjects having missing values after Screening or having missing visit dates were not included in the analysis. A total of 28 subjects (Granexin™ Gel plus SoC group: 8 [17.40]; SoC group: 20 [43.5%]) were censored due to reasons such as subjects not having complete 50% wound closure, lack of photographic evaluation data, withdrawal of consent, loss to follow-up, discontinued due to protocol non compliance, or death.

TABLE 48

Summary of Time to First Complete 50% Wound Closure by Week 12 ITT Population (N = 92)

| Statistics[1] | Treatment Group | |
| --- | --- | --- |
| | Granexin ™ Gel plus SoC (n = 46) | SoC (n = 46) |
| Number (%) of subjects with complete (50%) wound closure | 34(73.9%) | 25(54.3%) |
| Number (%) of censored subjects | 8(17.4%) | 20(43.5%) |
| Median duration (weeks) of complete wound closure (90% CI)[2] | 2.86(2.14; 3.00) | 6.86(5.00; 9.14) |
| p-value[3] | 0.0002 | |

Note:
[1]Percentage was calculated taking count of corresponding treatment groups as denominator.
[2]The median duration of complete wound closure was estimated by Kaplan-Meier method and also 90% confidence interval was calculated for the median duration of 50% wound closure.
[3]p-value was calculated using Log-rank test for treatment groups using Proc Lifetest procedure of SAS software Time taken to achieve 50% wound closure in the mITT population is summarized in Table 49 and FIG. 17. Out of 77 subjects, 59 (Granexin™ Gel plus SoC group: 33 [80.5%]; SoC group: 23 [63.9%]) had 50% wound closure by Week 12. The median duration of 50% wound closure was 2.86 weeks (90% CI was 2.14 to 3 weeks) in Granexin™ Gel plus SoC group and 8 weeks (90% CI: 5.14 to 9.86) in SoC group. Subjects in Granexin™ Gel plus SoC group took statistically significantly less time to achieve 50% wound closure than SoC group subjects (p-value <0.0001). Five (5.5%) subjects having missing values after Screening or having missing visit dates were not included in the analysis. A total of 19 subjects (Granexin™ Gel plus SoC group: 6 [14.6%]; SoC group: 13 [36.1%]) were censored due to reasons such as subjects not having complete 50% wound closure, lack of photographic evaluation data, withdrawal of consent, loss to follow-up, discontinued due to protocol non compliance, or death.

TABLE 49

Summary of Time to First Complete 50% Wound Closure by Week 12 mITT Population (N = 77)

| Statistics[1] | Treatment Group | |
| --- | --- | --- |
| | Granexin ™ Gel plus SoC (n = 41) | SoC (n = 36) |
| Number (%) of subjects with complete (50%) wound closure | 33(80.5%) | 23(63.9%) |
| Number (%) of censored subjects | 6(14.6%) | 13(36.1%) |
| Median duration (weeks) of complete wound closure (90% CI)[2] | 2.86(2.00; 3.00) | 8.00(5.14; 9.86) |
| p-value[3] | <0.0001 | |

Note:
[1]Percentage was calculated taking count of corresponding treatment groups as denominator.
[2]The median duration of complete wound closure was estimated by Kaplan-Meier method and also 90% confidence interval was calculated for the median duration of 50% wound closure.
[3]p-value was calculated using Log-rank test for treatment groups using Proc Lifetest procedure of SAS software.

The time taken to achieve 50% wound closure in the PP population is summarized in Table 50 and FIG. 18. Out of 68 subjects, 54 (Granexin™ Gel plus SoC group: 32 [91.40%]; SoC group: 22 [66.70%]) had 50% wound closure by Week 12. The median duration of 50% wound closure was 2.86 weeks (90% CI was 2 to 3 weeks) in Granexin™ Gel plus SoC group and 8 weeks (90% CI: 5.14 to 9.86) in SoC group. Subjects in Granexin™ Gel plus SoC group took statistically significantly less time to achieve 50% wound closure than SoC group subjects (p-value <0.0001). A total of 14 subjects (Granexin™ Gel plus SoC group: 3 [8.6%]; SoC: 11 [33.3%]) were censored as they did not complete 50% wound closure during the study period, or due to lack of photographic evaluation data, withdrawal of consent, loss to follow-up, discontinued due to protocol non compliance, or death.

TABLE 50

Summary of Time to First Complete (50%) Wound Closure by Week 12 PP Population (N = 68)

| Statistics[1] | Treatment Group | |
|---|---|---|
| | Granexin ™ Gel plus SoC (N = 35) | SoC (N = 33) |
| Number (%) of subjects with complete (50%) wound closure | 32(91.4%) | 22(66.7%) |
| Number (%) of censored subjects | 3(8.6%) | 11(33.3%) |
| Median duration (weeks) of complete wound closure (90% CI)[2] | 2.86(2.00; 3.00) | 8.00(5.14; 9.86) |
| p-value[3] | <0.0001 | |

Note:
[1]Percentage was calculated taking count of corresponding treatment groups as denominator.
[2]The median duration of complete wound closure was estimated by Kaplan-Meier method and also 90% CI was calculated for the median duration of 50% wound closure.
[3]p-value was calculated using Log-rank test for treatment groups using Proc Lifetest procedure of SAS software.

Additional to the Kaplan-Meier Model, Cox Proportional Hazards Regression Model was also used to compare the event-time distribution function between the two treatment groups. This analysis was conducted to evaluate if one or more covariates were associated with the time to 100% or 50% wound closure. Table 51 below summarizes the Cox Proportional Hazards Regression Analysis of time to complete wound closure in the ITT population. The effect of covariates estimated by the proportional hazards model is reported as hazard ratios. As per the hazards ratio and p-value, covariates such as treatment group and wound size showed an association with time to completion of wound closure (treatment group p-value=0.0406; wound size p-value=0.0265) and the subjects treated with Granexin™ Gel plus SoC would have wound closure 2.281 times more than the subjects treated with SoC only.

TABLE 51

Analysis of Time to First Complete (100%) Wound Closure (Cox's Proportional Hazards Regression Analysis)ITT Population (N = 92)

| Statistics | Hazard Ratio[1] | 95% CI for Hazard Ratio | | p-value |
|---|---|---|---|---|
| | | Lower | Upper | |
| Treatment group | 2.281 | 1.036 | 5.021 | 0.0406 |
| Wound size | 0.998 | 0.997 | 1.000 | 0.0265 |
| Wound duration | 1.000 | 0.996 | 1.003 | 0.8431 |
| Baseline wound depth | 1.767 | 0.312 | 10.006 | 0.5197 |
| BMI | 1.003 | 0.922 | 1.092 | 0.9423 |

Note:
[1]Cox Proportional Hazard ratio with 95% CI and p-value was calculated using PROC PHREG procedure.

Table 52 below summarizes the Cox Proportional Hazards Regression Analysis of time to complete wound closure in the mITT population. The effect of covariates estimated by the proportional hazards model is reported as hazard ratios. As per the hazards ratio and p-value, covariate such as treatment group showed an association with time to completion of wound closure (p-value=0.0139) and the subjects treated with Granexin™ Gel plus SoC would have wound closure 2.776 times more than the subjects treated with SoC only. Wound size, wound duration, baseline wound depth, and BMI were not associated with time to wound closure.

TABLE 52

Analysis of Time to First Complete (100%) Wound Closure (Cox's Proportional Hazards Regression Analysis)mITT Population (N = 77)

| Statistics | Hazard Ratio[1] | 95% CI for Hazard Ratio | | p-value |
|---|---|---|---|---|
| | | Lower | Upper | |
| Treatment group | 2.776 | 1.230 | 6.265 | 0.0139 |
| Wound size | 0.998 | 0.997 | 1.000 | 0.0629 |
| Wound duration | 1.000 | 0.996 | 1.003 | 0.8838 |
| Baseline wound depth | 2.306 | 0.409 | 13.004 | 0.3439 |
| BMI | 1.021 | 0.937 | 1.113 | 0.6386 |

Note:
[1]Cox Proportional Hazard ratio with 95% CI and p-value was calculated using PROC PHREG procedure.

Cox Proportional Hazards Regression Analysis for time to 1000% wound closure in the PP population is summarised in Table 53 below. The effect of covariates estimated by the proportional hazards model is reported as hazard ratios. As per the hazards ratio and p-value, covariates such as treatment group showed an association with time to completion of wound closure (p-value=0.0077) and the subjects treated with Granexin™ Gel plus SoC would have wound closure 3.150 times more than the subjects treated with SoC only. Wound size, wound duration, baseline wound depth, and BMI were not associated with time to wound closure.

TABLE 53

Analysis of Time to First Complete (100%) Wound Closure (Cox's Proportional Hazards Regression Analysis) PP Population (N = 68)

| Statistics | Hazard Ratio[1] | 95% CI for Hazard Ratio | | p-value |
|---|---|---|---|---|
| | | Lower | Upper | |
| Treatment Group | 3.150 | 1.354 | 7.326 | 0.0077 |
| Wound size | 0.999 | 0.997 | 1.000 | 0.0714 |
| Wound duration | 1.000 | 0.997 | 1.003 | 0.9942 |
| Baseline wound depth | 2.027 | 0.333 | 12.352 | 0.4435 |
| BMI | 1.021 | 0.935 | 1.114 | 0.6449 |

Note:
[1]Cox Proportional Hazard ratio with 95% CI and p-value was calculated using PROC PHREG procedure.

Time to 50% wound closure in the ITT population is summarized in Table 54. As per the hazards ratio and p-value, covariates such as treatment group and wound size, showed an association with time to completion of wound closure (treatment group p-value=0.0143; wound size p-value=0.0162) and the subjects treated with Granexin™ Gel plus SoC would have wound closure 2.247 times more than the subjects treated with SoC only.

TABLE 54

Analysis of Time to First Complete (50%) Wound Closure (Cox's Proportional Hazards Regression Analysis) ITT Population (N = 92)

| Statistics | Hazard Ratio[1] | 95% CI for Hazard Ratio | | p-value |
|---|---|---|---|---|
| | | Lower | Upper | |
| Treatment Group | 2.247 | 1.176 | 4.294 | 0.0143 |
| Wound size | 0.999 | 0.997 | 1.000 | 0.0162 |

TABLE 54-continued

Analysis of Time to First Complete (50%) Wound Closure (Cox's Proportional Hazards Regression Analysis) ITT Population (N = 92)

| Statistics | Hazard Ratio[1] | 95% CI for Hazard Ratio | | p-value |
|---|---|---|---|---|
| | | Lower | Upper | |
| Wound duration | 1.000 | 0.997 | 1.002 | 0.7702 |
| Baseline wound depth | 0.680 | 0.182 | 2.537 | 0.5654 |
| BMI | 0.988 | 0.928 | 1.052 | 0.7046 |

Note:
[1]Cox Proportional Hazard ratio with 95% confidence interval and p-value was calculated using PROC PHREG procedure.

Time to 50% wound closure in the mITT population is summarized in Table 55. As per the hazards ratio and p-value, covariates such as treatment group and wound size, showed an association with time to completion of wound closure (treatment group p-value=0.0067; wound size p-value=0.0346) and the subjects treated with Granexin™ Gel plus SoC would have wound closure 2.501 times more than the subjects treated with SoC only.

TABLE 55

Analysis of Time to First Complete (50%) Wound Closure (Cox's Proportional Hazards Regression Analysis) mITT Population (N = 77)

| Statistics | Hazard Ratio[1] | 95% CI for Hazard Ratio | | p-value |
|---|---|---|---|---|
| | | Lower | Upper | |
| Treatment Group | 2.501 | 1.289 | 4.853 | 0.0067 |
| Wound size | 0.999 | 0.998 | 1.000 | 0.0346 |
| Wound duration | 1.000 | 0.997 | 1.002 | 0.8310 |
| Baseline wound depth | 0.805 | 0.217 | 2.991 | 0.7461 |
| BMI | 0.998 | 0.937 | 1.064 | 0.9585 |

Note:
[1]Cox Proportional Hazard ratio with 95% confidence interval and p-value was calculated using PROC PHREG procedure.

Time to 50% wound closure in the PP population is summarized in Table 56. As per the hazards ratio and p-value, covariates such as treatment group and wound size, showed an association with time to completion of 50% wound closure (treatment group p-value=0.0059; wound size p-value=0.0442) and the subjects treated with Granexin™ Gel plus SoC would have wound closure 2.611 times more than the subjects treated with SoC only.

TABLE 56

Analysis of Time to First Complete (50%) Wound Closure (Cox's Proportional Hazards Regression Analysis) PP Population (N = 68)

| Statistics | Hazard Ratio[1] | 95% CI for Hazard Ratio | | p-value |
|---|---|---|---|---|
| | | Lower | Upper | |
| Treatment Group | 2.611 | 1.319 | 5.169 | 0.0059 |
| Wound size | 0.999 | 0.998 | 1.000 | 0.0442 |
| Wound duration | 1.000 | 0.997 | 1.002 | 0.8788 |
| Baseline wound depth | 0.604 | 0.151 | 2.412 | 0.4755 |
| BMI | 0.998 | 0.935 | 1.064 | 0.9469 |

Note:
[1]Cox Proportional Hazard ratio with 95% confidence interval and p-value was calculated using PROC PHREG procedure.

Wound Recurrence

Overall in ITT, mITT, and PP population, wound recurrence was reported in 10 subjects (Granexin™ Gel plus SoC group: 5 subjects; SoC group: 5 subjects) for the entire duration of the study. Of these 10 subjects, wound recurrence was observed in 2 subjects in Granexin™ Gel plus SoC group (Subject 504, Subject 907) and 2 subjects in SoC group (Subject 1003; Subject 1103) after completion of treatment at 12 weeks. There was no statistically significant difference in wound recurrence between the 2 treatment groups (p-value >0.9999).

TABLE 57

Wound Recurrence in the Overall Population

| Recurrence, n (%)[1] | Treatment Group | | Overall (N = 92) |
|---|---|---|---|
| | Granexin™ Gel plus SoC (N = 46) | SoC (N = 46) | |
| At any visit | | | |
| Yes | 5 (10.9%) | 5 (10.9%) | 10 (10.9%) |
| No | 41 (89.1%) | 41 (89.1%) | 82 (89.1%) |
| p-value[2] | — | ≥0.9999 | — |
| After Week 12 | | | |
| Yes | 2 (4.3%) | 2 (4.3%) | 4 (4.3%) |
| No | 44 (95.7%) | 44 (95.7%) | 88 (95.7%) |
| p-value[2] | — | ≥0.9999 | — |

Note:
[1]Percentage was calculated by taking respective column header group count as denominator.
[2]p-value was calculated using the chi-square Test for comparison between two treatment groups.

Table 58 summarizes the time points of wound recurrence. Wound recurrence within 2 weeks was observed in 3 subjects (Subject 704, Subject 907, Subject 1002) in Granexin™ Gel plus SoC group and 2 subjects (Subject 208, Subject 902) in SoC group.

TABLE 58

Timepoints of Wound recurrence

| Subject Number | Treatment Group | Visit Wound Healed | Visit Wound recurred | Visit Wound Healed Again |
|---|---|---|---|---|
| 206 | Granexin™ Gel plus SOC | Visit 9 | Visit 13 | — |
| 504 | Granexin™ Gel plus SOC | Visit 8 | Visit 18 | — |
| 704 | Granexin™ Gel plus SOC | Visit 10 | Visit 11 | — |
| 907 | Granexin™ Gel plus SOC | Visit 15 | Visit 16 | Visit 17 |
| 1002 | Granexin™ Gel plus SOC | Visit 7 | Visit 8 | Visit 12 |
| 208 | SOC | Visit 10 | Visit 11 | Visit 16 |
| 902 | SOC | Visit 8 | Visit 9 | Visit 10 |
| 1003 | SOC | Visit 9 | Visit 16 | — |
| 1103 | SOC | Visit 10 | Visit 16 | Visit 17 |
| 1107 | SOC | Visit 11 | Visit 13 | — |

The intensity of pain experienced by the subjects was recorded on a Visual Analogue Scale of 1 to 10 where 1 indicated "no pain" and 10 indicated "extreme pain" at all visits. The summary of subject self assessment of intensity of pain at all visits from Baseline to Week 12 for the ITT population is presented in and Table 59.

Table 59 summarizes the analysis of subject self assessment of intensity of pain at Week 12 for the ITT population. The intensity of pain was not statistically significantly higher in subjects treated with Granexin™ Gel plus SoC as compared to those treated with SoC only (p-value=0.8393).

TABLE 59

Analysis of Subject Self Assessment of Intensity
of Pain at Week 12 ITT Population (N = 92)

| | Treatment Group | |
|---|---|---|
| Statistics | Granexin ™ Gel plus SoC group (N = 46) | SoC group (N = 46) |
| Intensity of pain at Week 12 | | |
| n | 39 | 38 |
| Mean | 0.46 | 0.34 |
| SD | 1.072 | 0.708 |
| Median | 0.00 | 0.00 |
| Range (Min:Max) | (0.0:5.0) | (0.0:3.0) |
| Missing | 0 | 1 |
| p-value[1] | 0.8393 | |

Note:
[1]p-value is evaluated by using non-parametric Wilcoxon Mann-Whitney U test between treatment group.

Table 60 summarizes the analysis of subject self assessment of intensity of pain at Week 12 for the mITT population. The intensity of pain was not statistically significantly higher in subjects treated with Granexin™ Gel plus SoC as compared to those treated with SoC only (p-value=0.1663).

TABLE 60

Analysis of Subject Self Assessment of Intensity
of Pain at Week 12 mITT Population (N = 77)

| | Treatment Group | |
|---|---|---|
| Statistics | Granexin ™ Gel plus SoC group (N = 41) | SoC group (N = 36) |
| Intensity of pain at Week 12 | | |
| n | 34 | 29 |
| Mean | 0.18 | 0.45 |
| SD | 0.387 | 0.783 |
| Median | 0.00 | 0.00 |
| Range (Min:Max) | (0.0:1.0) | (0.0:3.0) |
| Missing | 0 | 1 |
| p-value[1] | 0.1663 | |

| | Treatment Group | |
|---|---|---|
| Statistics | Granexin ™ Gel plus SoC group (N = 46) | SoC group (N = 46) |
| Intensity of pain at Week 12 | | |
| N | 34 | 27 |
| Mean | 0.18 | 0.48 |
| SD | 0.387 | 0.802 |
| Median | 0.00 | 0.00 |

| | Treatment Group | |
|---|---|---|
| Statistics | Granexin ™ Gel plus SoC group (N = 41) | SoC group (N = 46) |
| Range (Min:Max) | (0.0:1.0) | (0.0:3.0) |
| Missing | 0 | 1 |
| p-value[1] | 0.1195 | |

Note:
[1]p-value is evaluated by using non-parametric Wilcoxon Mann-Whitney U test between treatment group.

Wound Tracing were done for all subjects from Screening till Visit 15 or till the time the wound had healed. Qualitative Assessment of the wound site were done at the site at every visit for the presence of granulation, necrotic tissue, exudate levels, wound odor, and eschar as listed in the CRF.

The non-parametric Wilcoxon Mann-Whitney U test was used to analyze mean percent reduction of wound area from Baseline to Week 12 in both the treatment groups since the data did not follow a normal distribution, as confirmed by a Shapiro-Wilk p-value of <0.0001 and anon-linear Q-Q plot. The addition of ranks of both groups obtained after sorting the data of wound size reduction in ascending order showed that in Granexin™ Gel plus SoC subjects, the actual sum of scores was higher than the expected sum of scores (ITT: actual: 1210.00, expected: 1071.00; mITT: actual: 1136.00, expected: 990.00; PP: actual: 1123.00, expected: 973.50). In SoC group, the actual sum of scores was lower than the expected sum of the scores (ITT: actual: 743.00, expected: 882.00; mITT: actual: 634.00, expected: 780.00; PP: actual: 588.00; expected: 737.50). Therefore, subjects in Granexin™ Gel plus SoC group had a statistically significantly higher percent wound closure from Baseline to Week 12, as compared to subjects in SoC group (ITT p-value=0.0238; mITT p-value=0.0105; PP p-value=0.0073).

Non-parametric analysis for secondary endpoint showed that the mean percent reduction of wound area from Baseline to Week 4 in Granexin™ Gel plus SoC group was statistically significantly higher, as compared to subjects in SoC group (ITT p-value=0.0006; mITT p-value=0.0001; PP p-value <0.0001).

Time to complete (100%) wound closure by Week 12 was statistically significantly lesser in Granexin™ Gel plus SoC group, as compared to SoC group (ITT p-value=0.0006; mITT p-value <0.0001; PP p-value <0.0001). In Granexin™ Gel plus SoC group, 60.9% in the ITT population, 68.3% subjects in mITT population, and 80.0% subjects in the PP population had 100% wound closure by Week 12 as compared to 32.6% in the ITT population, 36.1% subjects in mITT population, and 36.4% in the PP population in the SoC group. The median duration of 100% wound closure was 6 weeks in ITT, mITT, and PP population in the Granexin™ Gel plus SoC group. In the SoC group, the median duration of time to complete wound closure was about 12.14 weeks in the ITT population and not achieved in the mITT and PP population.

The time taken to achieve 50% wound closure by Week 12 was statistically significantly lower in Granexin™ Gel plus SoC group as compared to SoC group subjects (ITT p-value=0.0002, mITT p-value <0.0001, PP p-value <0.0001). In Granexin™ Gel plus SoC group, 73.9% subjects in the ITT, 80.5% subjects in mITT population, and 91.4% subjects in the PP population had 50% wound closure and in SoC group, 54.3% subjects in ITT, 63.9% subjects in mITT population, and 66.7% in PP population had 50% wound closure. In ITT, mITT, and PP population, the median duration of 50% wound closure was 2.86 weeks in subjects treated with Granexin™ Gel plus SoC. Subjects treated with SoC alone had median duration of 6.86 weeks in the ITT population and 8 weeks in the both the mITT and PP population.

In Cox Proportional Hazard Regression Analysis for time to 100% wound closure covariates such as treatment group showed a significant association with time to completion of wound closure (ITT p-value=0.0406; mITT p-value=0.0139, PP p-value=0.0077) and the Granexin™ Gel plus SoC group subjects had ITT: 2.281; mITT p-value=2.776; PP: 3.150 times more chances of 100% wound closure than the SoC group subjects. Wound duration, wound size, baseline wound depth, and BMI were not significant factors affecting wound closure. Treatment group and wound size showed a significant association with time to completion of 50% wound closure (ITT: treatment group p-value=0.0143; wound size p-value=0.0162; mITT: treatment group p-value=0.0067; wound size p-value=0.0346; PP: treatment group p-value=0.0059; wound size p-value=0.0442) and the Granexin™ Gel plus SoC group subjects had ITT: 2.247; mITT: 2.501 times; PP: 2.61 times more chances of wound closure than the SoC group subjects. Wound duration, baseline wound depth, and BMI were not significant factors affecting 50% wound closure.

The categorical analysis of incidence of 100% wound closure at Week 12 was done using the Cochran-Mantel-Haenszel analysis with Breslow-Day test and the Chi-square test. The Chi-square test performed by combining the data from all the study centers showed that the number of responders with 100% wound closure in Granexin™ Gel plus SoC group (ITT: 56.5%; mITT: 63.4%; PP: 74.3%) was statistically significantly higher than in SoC group (ITT: 28.3%; mITT: 30.6%; PP: 30.3%) (ITT: p-value=0.0061; mITT p-value=0.0040; PP: p-value=0.0003).

The number of responders with 50% wound closure in Granexin™ Gel plus SoC group were 63% in ITT, 68.3% in mITT population as compared to 43.5% in ITT, 50% in mITT population in the SoC group which was not statistically significant (ITT p-value=0.0600; mITT p-value=0.1025). The number of responders with 50% wound closure in Granexin™ Gel plus SoC group in the PP population were 80% as compared to 51.5% in the SoC group which was statistically significantly higher (p-value=0.0131).

Hence, in the PP population, the frequency of 100% and 50% wound closure (epithelialization) was significantly higher in wounds treated with Granexin™ Gel plus SoC s than in SoC group subjects.

The intensity of pain experienced by the subjects was recorded on a Visual Analogue Scale of 1 to 10 where 1 indicated "no pain" and 10 indicated "extreme pain". There was no statistically significant difference in subject self assessment of intensity of pain at the end of treatment at Week 12 between the 2 treatment groups (ITT p-value=0.8393; mITT p-value=0.1663, PP p-value=0.1195, Wilcoxon Mann-Whitney U test).

Brief Summary of Adverse Events

Overall, 28 subjects reported 40 AEs of which 24 AEs were reported by subjects in Granexin™ Gel plus SoC group; 16 AEs were reported in the SoC group. Out of 24 AEs, 21 (87.50) in Granexin™ Gel plus SoC group and out of 16 AEs, 12 (75%) AEs in SoC group were mild. Three (12.5%) events in Granexin™ Gel plus SoC group and 3 (18.8) events in SoC group were moderate; and 1(6.3%) event in SoC group was severe. None of the AEs in either Granexin™ Gel plus SoC group or SoC group were related to the study drug or study treatment. Of the 40 events, 35 (87.5%) recovered and (2.5%) event recovered with sequelae, 3(7.5) AEs were ongoing when the subject completed the study. No action was taken against 39 (97.5%) AEs. None of the subjects withdrew due to AE and (1%) 1 subject in SoC group discontinued the study treatment due to death.

A total of 2 (2.2) reported in SoC group one of which was death due to MI and the other was Deep Vein Thrombosis. Both the SAEs were not related to the study treatment. No SAEs were reported in subjects in Granexin™ Gel plus SoC group (Table 61).

TABLE 61

Overview of Adverse Events-Safety Population (N = 92)

| | Treatment Group | | |
|---|---|---|---|
| Statistics | Granexin ™ Gel plus SoC (N = 46) | SoC (N = 46) | Overall (N = 92) |
| Total number of AEs reported | 24 | 16 | 40 |
| Subjects reporting any AEs[1] | 14 (30.4%) | 14 (30.4%) | 28 (30.4%) |
| Subjects reporting 1 AE | 8 (17.4%) | 12 (26.1%) | 20 (21.7%) |
| Subjects reporting > 1 AE | 6 (13.0%) | 2 (4.3%) | 8 (8.7%) |
| Subjects Reporting No AEs[1] | 32 (69.6%) | 32 (69.6%) | 64 (69.6%) |
| Number of AEs with severity of:[2] | | | |
| Mild | 21 (87.5%) | 12 (75.0%) | 33 (82.5%) |
| Moderate | 3 (12.5%) | 3 (18.8%) | 6 (15.0%) |
| Severe | 0 (0.0%) | 1 (6.3%) | 1 (2.5%) |
| Number of AEs with relationship of:[2] | | | |
| Not Related | 24 (100.0%) | 16 (100.0%) | 40 (100.0%) |
| Unlikely | 0 (0.0%) | 0 (0.0%) | 0 (0.0%) |
| Possible | 0 (0.0%) | 0 (0.0%) | 0 (0.0%) |
| Probable | 0 (0.0%) | 0 (0.0%) | 0 (0.0%) |
| Definite | 0 (0.0%) | 0 (0.0%) | 0 (0.0%) |
| Number of AEs by outcome:[2] | | | |
| Recovered | 22 (91.7%) | 13 (81.3%) | 35 (87.5%) |
| Recovered with sequelae | 0 (0.0%) | 1 (6.3%) | 1 (2.5%) |
| On-going when subject completed the study | 2 (8.3%) | 1 (6.3%) | 3 (7.5%) |
| Death | 0 (0.0%) | 1 (6.3%) | 1 (2.5%) |
| Unknown | 0 (0.0%) | 0 (0.0%) | 0 (0.0%) |
| Number of AEs by action taken:[2] | | | |
| None | 24 (100.0%) | 15 (93.8%) | 39 (97.5%) |
| Discontinued study drug | 0 (0.0%) | 1 (6.3%) | 1 (2.5%) |
| Subjects reporting AEs leading to withdrawal[1] | 0 (0.0%) | 0 (0.0%) | 0 (0.0%) |
| Subjects reporting SAEs[1] | 0 (0.0%) | 2 (4.3%) | 2 (2.2%) |
| Subjects reporting death | 0 (0.0%) | 1 (2.2%) | 1 (1.1%) |

Note:
[1]Percentage was calculated by taking respective column header group count as denominator.
[2]Percentage was calculated by taking count of 'Total Number of AEs Reported' in corresponding treatment group as denominator.

Display of Adverse Events

The AEs by MedDRA system organ class and preferred term are summarized in Table 62.

There was no statistically significant difference in the number of subjects with at least 1 AE between the treatment groups (p-value ≥0.9999). More than 50% safety population reported venous ulcer pain (10 [10.90%]) and wound complication (12 [13.0%] subjects).

TABLE 62

Summary of Adverse Events by MedDRA System Organ Class and Preferred Term Safety Population (N = 92)

| System Organ Class/Preferred Term | Treatment Group n (%)[1] | | | |
|---|---|---|---|---|
| | Granexin ™ Gel plus SoC (n = 46) | SoC (n = 46) | Overall (N = 92) | p-value[2] |
| Total number of subjects with at least one AE | 14 (30.4%) | 14 (30.4%) | 28 (30.4%) | ≥0.9999 |
| Total number of AEs reported | 24 | 16 | 40 | |
| Cardiac disorders | 0 (0.0%) | 1 (2.2%) | 1 (1.1%) | |
| Myocardial infarction[3] | 0 (0.0%)[0] | 1 (2.2%)[1] | 1 (1.1%)[1] | |
| General disorders and administration site conditions | 0 (0.0%) | 2 (4.3%) | 2 (2.2%) | |
| Pyrexia | 0 (0.0%)[0] | 2 (4.3%)[2] | 2 (2.2%)[2] | |
| Infections and infestations | 2 (4.3%) | 1 (2.2%) | 3 (3.3%) | |
| Wound infection | 2 (4.3%)[1] | 1 (2.2%)[2] | 3 (3.3%)[4] | |
| Injury, poisoning and procedural complications | 2 (4.3%) | 4 (8.7%) | 6 (6.5%) | |
| Blister | 1 (2.2%)[1] | 0 (0.0%)[0] | 1 (1.1%)[1] | |
| Wound complication | 7 (15.2%)[11] | 5 (10.9%)[5] | 12 (13.0%)[16] | |
| Respiratory, thoracic and mediastinal disorders | 2 (4.3%) | 0 (0.0%) | 2 (2.2%) | |
| Cough | 1 (2.2%)[1] | 0 (0.0%)[0] | 1 (1.1%)[1] | |
| Pneumonitis | 1 (2.2%)[1] | 0 (0.0%)[0] | 1 (1.1%)[1] | |
| Skin and subcutaneous tissue disorders | 7 (15.2%) | 4 (8.7%) | 11 (12.0%) | |
| Venous ulcer pain | 6 (13.0%)[6] | 4 (8.7%)[4] | 10 (10.9%)[10] | |
| Dermatitis allergic | 1 (2.2%)[1] | 0 (0.0%)[0] | 1 (1.1%)[1] | |
| Pruritus | 1 (2.2%)[1] | 0 (0.0%)[0] | 1 (1.1%)[1] | |
| Vascular disorders | 0 (0.0%) | 1 (2.2%) | 1 (1.1%) | |
| Bleeding varicose vein | 0 (0.0%)[0] | 1 (2.2%)[1] | 1 (1.1%)[1] | |
| Deep vein thrombosis | 0 (0.0%)[0] | 1 (2.2%)[1] | 1 (1.1%)[1] | |

Note:
[1]Percentage was calculated by taking respective column header group count as denominator.
[2]Percentage was calculated by comparing two treatment group using Chi-square test.
[3]Myocardial infarction led to death of the subject.

Of the 40 AEs reported in this study, one severe event of MI was reported by a subject in the SoC group None of the AEs (Granexin™ Gel plus SoC group: 24 [100%]; SoC group: 16 [100.0%] had any definite, probable, or possible relationship to Granexin™ Gel or the study treatment. One subject (Subject 1115) in SoC group was discontinued from the study treatment due to death. No other subjects were withdrawn or discontinued from the study due to an AE. Out of 40 AEs, 35 (87.5%) recovered, 1 (2.5%) AE (venous ulcer pain) in SoC group (Subject 102) recovered with sequelae, 3 (3.3%) AEs of wound complication (Granexin™ Gel plus SoC group: 2 subjects [Subject 702, 916]; SoC group: 1 subject [Subject 1113]) were on-going when the subjects completed the study, and 1 subject (Subject 1115, SoC group) died due to MI. One subject (Subject 1115, SoC group) died due to MI.

At Screening visit, of the 9 female subjects in the study, 2 were surgically sterilized and 4 were post menopausal. Pregnancy test was done for 3 (3.3%) subjects and doppler waveform analysis for all 92 subjects. The mean Doppler waveform reading for Granexin™ Gel plus SoC group subjects was 11.60 cm/s and 9.57 cm/s for SoC group subjects. X-ray was taken for 86 (93.5%) subjects where X-ray finding was normal for 81 (88.0%) and abnormal for 5 (5.4%) subjects, which was not clinically significant. None of the target wounds were infected with R hemolytic *Streptococcus* culture. The eGFR for males in Granexin™ Gel plus SoC group was 95.18 mL/min and 88.50 mL/min in SoC group subjects. However, the eGFR for female and ABPI were comparable between the treatment groups.

None of the subjects in the study had clinically significant hematological parameters at Screening visit or Week 12. Two subjects in Granexin™ Gel plus SoC group had clinically significant HbA1c at Screening visit but none of the subjects had clinically significant HbA1c at 12 weeks. None of the subjects had any clinically significant creatinine, uric acid, BUN, potassium, sodium, chloride, bicarbonate, albumin, AST, ALT, and total cholesterol at Screening visit or at Week 12.

Immunogenicity Testing: Using universal precautions recommended for biological samples, the blood samples were collected in yellow top gel vaccutainers. They were properly labeled with date and time of collection, site number, visit number, screening and randomization number, and the sample type. Using acceptable venipuncture technique 7 mL of whole blood was collected and allowed to stand for 15 min for the clot to form. Serum was separated by centrifuging the blood samples at 3500 rpm. Approximately 2 mL of the separated serum was pipetted out into two aliquots and refrigerated at 2-6° C. till shipped. These tubes were labeled with date and time of collection, site number, visit number, screening and randomization number, and the sample type. These samples were shipped to a central storage facility (Metropolis Laboratory, Mumbai) under appropriate temperature conditions with dry ice or frozen cold packs.

The samples were stored at −20° C. at Metropolis and shipped in batches to WuXi Laboratories at Philadelphia, Pa., under appropriate temperature conditions with serum sample shipment forms.

Anti-ACT1 antibodies were not detected in the serum in any of the subjects at Screening and Week 12.

The systolic and diastolic blood pressure, heart rate, respiratory rate, and body temperature were comparable between the treatment groups at Screening visit and at Week 12.

In the overall safety population, the ECG was normal in 81 (88.0%) subjects. Changes in ECG impression reported in the remaining subjects were not clinically significant at the Screening visit (End-of-Text Table 14.3.6)

Overall, 28 (30.4%) subjects reported 40 AEs of which 24 AEs were reported by subjects in Granexin™ Gel plus SoC group; 16 AEs were reported in the SoC group. Out of 24 AEs, 21 (87.5%) in Granexin™ Gel plus SoC group and out of 16 AEs, 12 (75%) AEs in SoC group were mild. Three (12.5%) events in Granexin™ Gel plus SoC group and 3 (18.8%) events in SoC group were moderate; and 1(6.3%) event in SoC group was severe. None of the AEs in either Granexin™ Gel plus SoC group or SoC group were related to the study drug or study treatment. Of the 40 events, 35 (87.5%) recovered and 1 (2.5%) event recovered with sequelae. None of the subjects withdrew due to an AE and 1(1.1%) subject in SoC group discontinued the study treatment due to death.

A total of 2 (2.2%) SAEs were reported in SoC group one of which was death due to Myocardial Infarction and the other was Deep Vein Thrombosis. Both the SAEs were not related to the study treatment. No SAEs were reported by subjects in Granexin™ Gel plus SoC group Overall, there was no significant difference in the number of subjects reporting AEs between the 2 treatment groups (Granexin™ Gel plus SoC group, 14; SoC group, 14; p-value >0.9999).

At Screening visit, no clinically significant abnormalities were observed in any of the treatment groups. The vital signs and ECG were normal and comparable between both the treatment groups. Anti-ACT1 peptide antibodies were not detected in any of the subjects in both Screening and EOS serum samples.

This was a double blind, randomized, prospective, parallel group, multi-center Phase II study conducted at 10 centers in India to evaluate the efficacy and safety of Granexin™ Gel in the treatment of VLU. The total duration of the study was 11 months, including 5 months enrollment period and 6 months for study procedures. The study duration for individual subjects was 6 months which included 18 visits. A total of 101 subjects with VLU were screened for this study, 5 were found to be screen failures, and 4 subjects did not initiate participation in the study. A total of 92 subjects enrolled in the study had mean wound duration of 68.4 weeks at Screening and mean wound area of 353.64 mm$^2$ at Baseline. These subjects were randomized to receive Granexin™ Gel plus SoC or SoC alone for the treatment of VLU. Of these, 70 completed the study and 22 subjects did not complete the study due to consent withdrawal, loss to follow-up, non-compliance, or SAE.

Of 92 enrolled subjects, 15 subjects met exclusion criterion number 1 or did not have adequate evaluable wound photographic data post randomization but were considered in the Safety and ITT population. These subjects were excluded from the mITT and PP populations. A total of 83 (90.2%) subjects were males and 9 (9.8%) were females. The mean age of the study population was 49.8 years, mean weight was 70.47 kg, mean height was 168.35 cms, and mean BMI was 24.79 kg/m$^2$.

The primary efficacy endpoint of the study was to evaluate mean percent wound closure from Baseline (Visit 2) to Week 12 (Visit 15). The non-parametric Wilcoxon Mann-Whitney U test was used to analyze mean percent reduction of wound area from Baseline to Week 12 in both the treatment groups since the data did not follow a normal distribution, as confirmed by a Shapiro-Wilk p-value <0.0001 and a non-linear Q-Q plot. Subjects treated with Granexin™ Gel plus SoC showed statistically significantly higher percent wound closure from Baseline to Week 12 compared to subjects treated with SoC alone (ITT p-value=0.0238; mITT p-value=0.0105; PP p-value=0.0073), suggesting that at Week 12, wounds treated with Granexin™ Gel plus SoC had a significant reduction in size as compared to wounds treated with SoC alone.

Mean percent wound closure at Week 4, time to complete (100% and 50%) wound closure, incidence of complete wound closure, and subject self assessment of pain were also analyzed. At Week 4, the wound area percent of reduction in Granexin™ Gel plus SoC group was statistically significantly higher than in SoC group (ITT p-value=0.0006; mITT p-value=0.0001; PP p-value <0.0001 Wilcoxon Mann-Whitney U test).

Subjects treated with Granexin™ Gel plus SoC achieved 100% wound closure in median duration of 6 weeks in ITT, mITT, and PP population which was significantly faster compared to the SoC group in which the median duration was 12.14 weeks in the ITT population and not achieved in both mITT and PP population during the 12 weeks of efficacy assessments (ITT p-value=0.0006; mITT p-value=0.0001; PP p-value <0.0001; log-rank test).

Subjects treated with Granexin™ Gel plus SoC achieved 50% wound closure in 2.86 weeks in both ITT and PP population while subjects treated with SoC alone achieved it in 6.86 weeks in ITT population and 8 weeks in both mITT and PP population, respectively (ITT p-value=0.0002, mITT p-value <0.0001, PP p-value <0.0001). The categorical analysis of incidence of 100% and 50% wound closure at Week 12 was conducted and the subjects who had 100% wound closure were considered as responders. Overall in the ITT, mITT, and PP populations, 56.5%, 63.4%, and 74.3% of the subjects in Granexin™ Gel plus SoC group, respectively, responded to treatment with 100% wound closure as compared to 30.3% of the subjects in the SoC group. The number of responders were significantly higher in Granexin™ Gel plus SoC group than in the SoC group (ITT: p-value=0.0061; mITT p-value=0.0040; PP: p-value=0.0003; Chi-square analysis). Similarly, in the PP population, 80.0% of the subjects in Granexin™ Gel plus SoC group responded to treatment and achieved 50% wound closure as compared to 51.5% of the subjects in the SoC group. The number of responders with 50% wound closure were significantly higher in Granexin™ Gel plus SoC group than in the SoC group (p-value=0.0131; Chi-square analysis), indicating that the wounds treated with Granexin™ Gel plus SoC have higher incidences of 100% and 50% wound closure (epithelialization) than wounds treated with SoC alone.

Cox Proportional Hazard Regression Model analysis was conducted to evaluate if one or more covariates such as treatment group, wound duration, baseline wound depth, and BMI etc. were associated with the time to complete 100% or 50% wound closure. It showed that treatment group was a significant factor affecting wound closure and Granexin™ Gel plus SoC group subjects had ITT: 2.281; mITT: 2.776; PP: 3.150 times more chances of 100% wound closure and ITT: 2.247; mITT: 2.501; PP: 2.61 times more chances of 50% wound closure than the SoC group subjects.

At every visit, self assessment of intensity of pain score was completed by each subject and the scores were given in comparison to the last visit. Therefore significant change in the pain scores was not observed and there was no statistically significant difference in intensity of pain as assessed by the subject at Week 12 between the 2 treatment groups.

The findings from the present study demonstrated a good safety profile with Granexin™ Gel. Overall, 28 subjects reported 40 AEs of which 24 AEs were reported by subjects in Granexin™ Gel plus SoC group; 16 AEs were reported in the SOC group. The only 2 SAEs reported, were in the SoC group. One SAE was Myocardial infarction which resulted in death, and the other SAE was Deep vein thrombosis. Of the 40 AEs, 35 (87.5%) recovered. None of the AEs were related to Granexin™ Gel. None of the subjects were withdrawn from the study due to an AE.

No clinically significant abnormalities in the laboratory parameters were observed in either of the treatment groups. The vital signs and ECG were normal and comparable between both the treatment groups. Anti-ACT1 peptide antibodies were not detected in the serum samples collected at Screening or at Week 12.

In conclusion, Granexin™ Gel along with SoC has shown to accelerate wound healing in subjects with VLU, making it an efficacious, safe, and well tolerated therapeutic option in the treatment of VLU.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited.

The publications discussed herein are provided solely for their disclosure prior to the filing date of the present application. Nothing herein is to be construed as an admission that the present invention is not entitled to antedate such publication by virtue of prior invention While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

TABLE 9

Wound Healing Gel Qualitative and Quantitative Composition

| Ingredients | Grade | Function | Concentration (% w/w) | Grams/kg Batch |
| --- | --- | --- | --- | --- |
| Peptide 328967 (ACT1) | — | Active | 0.0072; 0.018 0.036; 0.072 | 0.072; 0.18 0.36; 0.72 |
| Methylparaben | NF | Preservative | 0.17 | 1.7 |
| Propylparaben | NF | Preservative | 0.02 | 0.2 |
| Glycerin | USP | Solvent | 5 | 50 |
| Sodium Phosphate Monobasic | USP | Buffer Agent | 0.263 | 2.63 |
| Sodium Phosphate Dibasic | USP | Buffer Agent | 0.044 | 0.44 |
| Propylene Glycol | USP | Solvent | 3 | 30 |
| Edetate Disodium (EDTA) | USP | Chelating Agent | 0.05 | 0.5 |
| D-Mannitol | USP | Stabilizer | 0.05 | 0.5 |
| Hydroxyethylcellulose, 250HHX | NF | Gelling Agent | 1.25 | 12.5 |
| Purified Water, qsad | USP | Solvent | 1 | 1 kg |

The invention claimed is:

1. A composition for treating a chronic wound in a subject, consisting essentially of at least one alpha connexin polypeptide and a carrier, wherein the at least one alpha connexin polypeptide comprises the carboxy terminal-most 4 to 30 contiguous amino acids of an alpha connexin, or a conservative variant thereof, and wherein the carrier comprises hydroxyethylcellulose gel, wherein the hydroxyethylcellulose gel is present in the composition at a concentration of about 1.25% (w/w).

2. The composition of claim 1, wherein the alpha connexin polypeptide comprises the amino acid sequence of SEQ ID NO: 9.

3. The composition of claim 1, wherein the alpha connexin polypeptide comprises a cellular internalization transporter.

4. The composition of claim 3, wherein the cellular internalization transporter is an antennapedia sequence.

5. A method of treating a chronic wound in a subject, comprising administering to a subject in need thereof the composition of claim 1.

* * * * *